US008093455B2

(12) United States Patent
Finkers et al.

(10) Patent No.: US 8,093,455 B2
(45) Date of Patent: *Jan. 10, 2012

(54) TOMATO PLANTS HAVING HIGHER LEVELS OF RESISTANCE TO BOTRYTIS

(75) Inventors: Hendrikus Johannes Finkers, Wageningen (NL); Paulus Cornelis Maris, Benthuizen (NL); Willem Hendrik Lindhout, Wageningen (NL); Adriaan Willem van Heusden, Wageningen (NL)

(73) Assignee: Monsanto Invest N.V., Bergschenhoek (NL)

( * ) Notice: Subject to any disclaimer, the term of this patent is extended or adjusted under 35 U.S.C. 154(b) by 219 days.

This patent is subject to a terminal disclaimer.

(21) Appl. No.: 12/256,992

(22) Filed: Oct. 23, 2008

(65) Prior Publication Data

US 2009/0126037 A1 May 14, 2009

Related U.S. Application Data

(63) Continuation of application No. PCT/NL2007/050183, filed on Apr. 25, 2007.

(30) Foreign Application Priority Data

Apr. 25, 2006 (EP) .................................... 06075950

(51) Int. Cl.
*C12N 15/04* (2006.01)
*A01H 5/00* (2006.01)
*A01H 1/00* (2006.01)
*A01H 1/02* (2006.01)

(52) U.S. Cl. ........ 800/279; 800/298; 800/260; 800/265; 800/266; 800/267; 435/411; 435/468; 435/6.1

(58) Field of Classification Search ........................ None
See application file for complete search history.

(56) References Cited

FOREIGN PATENT DOCUMENTS

| EP | 1652930 A1 | 5/2006 |
|----|------------|--------|
| WO | 2002063020 A2 | 1/2002 |
| WO | 02085105 A2 | 10/2002 |
| WO | 2006046861 A2 | 5/2006 |

OTHER PUBLICATIONS

International Search Report relating to corresponding PCT/NL2007/050183 filed Apr. 25, 2007.
Churchill, et al., "Empiracal Threshold Values for Quantitative Trait Mapping" Genetics Society of America, 138: 963-971 (Nov. 2004).
Dik, et al., "Evaluation of Microbial Antagonists for Biological Control of *Botrytis cinerea* Stem Infection in Cucumber and Tomato" European Journal of Plant Pathology, 105: 115-122. 1999.
Frary, et al., "Fine Mapping of Quantitative Trait Loci for Improved Fruit Characteristics from Lycopersicon Chmielewskii Chromosome 1" Genome 46: 235-243 (2003).
Fridman, et al., "A Recombination Hotspot Delimits a Wild-Species Quantitative Trait Locus for Tomato Sugar Content to 484 bp Within an Invertase Gene" 4718-4723, PNAS, Apr. 25, 2000 vol. 97, No. 9.
Godoy, et al., "Use of Mutants to Demonstrate the Role of Oxalic Acid in Pathogenicity of *Sclerotinia sclerotiorum* on *Phaseolus vulgaris*" Physiological Molecular Plant Pathology, (1990) 37, 179-191.
Jansen, "Controlling the Type 1 and Type II Errors in Mapping Quantitative Trait Loci" Genetics 138: 871-881 (Nov. 1994).
Kosambi, "The Estimation of Map Distances from Recombination Values" Ann. Eugen. 1994, 12:172-175.
Ku, et al., "Exploitation of *Arabidopsis*-tomato Synteny to Construct a High-Resolution Map of the Ovate-Containing Region in Tomato Chromosome 2" Genome 44: 470-475 (2001).
Nicot, et al., "Differences in Susceptibility of Pruning Wounds and Leaves to Infection by *Botrytis cinerea* Among Wild Tomato Accessions" TGC Report, 2002, 52: 24-26.
Sanford, et al., "Optimizing the Biolistic Process for Different Biological Applications", Methods in Enzymology, 1993, 217:483-509.
Sobir, et al., "Molecular Characterization of the SCAR Markers Tightly Linked to the TM-2 Locus of the Genus" *Lycopersicon*. Theor. Appl. Genet. (2000) 101:64-69.
Utkhede, et al., "Effects of Biological and Chemical Treatments on *Botrytis* Stem Canker and Fruit Yield of Tomato Under Greenhouse Conditions" Can. J. Plant Pathol, 23: 253-259 (2001).
Utkhede, et al., "Biological Control of Stem Canker of Greenhouse Tomatoes Caused by *Botrytis cinerea*" Can. J. Microbiol 48: 550-554 (2002).
Voorrips, et al., "MapChart: Software for the Graphical Presentation of Linkage Maps and QTLs" The Journal of Heredity 2002:93(1) 77-78.
Salvi, et al., "To Clone or Not to Clone Plant QTLs: Present and Future Challenges" Trends in Plant Science vol. 10, No. 6, Jun. 2005 297-304.
Brouwer, et al., "QTL Analysis of Quantitative Resistance to *Phytophthora infestans* (Late Blight) in Tomato and Comparisons with Potato" Genome 47: 475-492 (2004).
van Heusden, et al., "Three QTLs from *Lycopersicon peruvianum* Confer a High Level of Resistance to *Clavibacter michiganensis* ssp. *Michiganensis*" Theor Appl Genet (1999) 99: 1068-1074.
Denby, et al., "Identification of *Botrytis cinerea* Susceptibility Loci in *Arabidopsis thaliana*" The Plant Journal (2004) 38, 473-486.
Ignatova, et al., "Resistance of Tomato F1 Hybrids to Grey Mold" Biotic Stresses, All-Russian Institute for Vegetable Crops, Novomitishinskiy pr. 82, NIIOH. Mitishi-18, Moscow Region, 141018, Russia, vol. 22, No. 3, 2000, 326-328.

*Primary Examiner* — Medina A Ibrahim
(74) *Attorney, Agent, or Firm* — Banner & Witcoff, Ltd.

(57) ABSTRACT

The present invention relates to a method for detecting a quantitative trait locus (QTL) associated with resistance to *Botrytis cinerea* in tomato, comprising the steps of crossing a *Botrytis*-resistant donor tomato plant with a non-resistant, or *Botrytis*-susceptible, recipient tomato plant, contacting one or more offspring plants with an infective amount of *Botrytis*, quantitatively determining the disease incidence and/or the rate of lesion growth in said one or more offspring plants, establishing a genetic linkage map that links the observed disease incidence and/or rate of lesion growth to the presence of chromosomal markers of said donor tomato plant in said one or more offspring plants, and assigning to a QTL the contiguous markers on said map that are linked to a reduced disease incidence and/or a reduced lesion growth rate.

25 Claims, 11 Drawing Sheets

| C12_12-1 | C12_12-2 | C12_12-3_(+ 9-2) |
|---|---|---|
| 0.0 — CT19 | 0.0 — CT19 | 0.0 — CT19 |
| 4.6 — TG68 | 4.6 — TG68 | 4.6 — TG68 |
| 9.6 — P14M48-411e | 9.6 — P14M48-411e | 9.6 — P14M48-411e |
| 13.6 — P18M50-244h | 13.6 — P18M50-244h | 13.6 — P18M50-244h |
| 14.3 — P18M50-273h | 14.3 — P18M50-273h | 14.3 — P18M50-273h |
| 24.0 — P14M61-420h | 24.0 — P14M61-420h | 24.0 — P14M61-420h |
| 25.4 — P14M61-406h | 25.4 — P14M61-406h | 25.4 — P14M61-406h |
| 31.7 — P14M61-223h | 31.7 — P14M61-223h | 31.7 — P14M61-223h |
| 33.9 — P14M60-193h | 33.9 — P14M60-193h | 33.9 — P14M60-193h |
| 38.2 — P22M51-314h | 38.2 — P22M51-314h | 38.2 — P22M51-314h |
| 39.5 — TG565 | 39.5 — TG565 | 39.5 — TG565 |
| 40.2 — P14M48-172h | 40.2 — P14M48-172h | 40.2 — P14M48-172h |
| 48.1 — P22M50-321e | 48.1 — P22M50-321e | 48.1 — P22M50-321e |
| 57.4 — P14M60-219e | 57.4 — P14M60-219e | 57.4 — P14M60-219e |
| 61.0 — P14M48-153h | 61.0 — P14M48-153h | 61.0 — P14M48-153h |
| 61.3 — P22M50-97h | 61.3 — P22M50-97h | 61.3 — P22M50-97h |
| 69.3 — TG296 | 69.3 — TG296 | 69.3 — TG296 |
| 75.2 — P22M50-131h | 75.2 — P22M50-131h | 75.2 — P22M50-131h |
| 89.7 — P22M51-135h | 89.7 — P22M51-135h | 89.7 — P22M51-135h |

Figure 5

Chromosome 1

SEQUENCE LISTING

<160> NUMBER OF SEQ ID NOS: 79

<210> SEQ ID NO 1
<211> LENGTH: 528
<212> TYPE: DNA
<213> ORGANISM: Solanum lycopersicon

<400> SEQUENCE: 1

```
gagacagctt gcatgcctgc agaggtgata aattcaccaa ggtttcatat ttaggaaaca      60
agaaaattaa aagatcatta acacagatga aaggatatga ctaggaggca atgactgatc     120
tttgactatc aaatacttct cagggaaaca atgtgaatgg gcttttacat gcagagatat     180
tgattgtgat catgttgaag aacttaggaa acatgaaatt aaatgatcat taacactgat     240
gcaaggatat gccaagtagg caagcaaatt aaggttgaac ataaatgtct gtgatctttg     300
actatcaaat atcttctcag aaaaaaaaat gtgaatgctc atttacatgc agagatggct     360
attgtgatca tgtggctcag ccttgagtct atattgaggt gcagacaaca tagtccctaa     420
ccacatgtgt gatcaagcaa cttttttgat gtccacaggg ttataagtag gcaacattta     480
agcaagaaaa aacacaggat cactattgag tcagctgctg ttgcctgt                   528
```

<210> SEQ ID NO 2
<211> LENGTH: 537
<212> TYPE: DNA
<213> ORGANISM: Solanum lycopersicon

<400> SEQUENCE: 2

```
ggagacaagc ttgcatgcct gcagaggtga taaattcacc aaggtttcat atttaggaaa      60
caagaaaatt aaaagatcat taacacagat gaaaggatat gactagtagg caatgactga     120
tctttgacta tcaaatactt ctcagggaaa caatgtgaat gggcttttac atgcagagat     180
attgattgtg atcatgttga agaacttagg aaacatgaaa ttaaatgatc attaacactg     240
atgcaaggat atgccaagta ggcaagcaaa ttaaggttga acataaatgt ctgtgatctt     300
tgactatcaa atatcttctc agaaaaaaaa atgtgaatgc tcatttacat gcagagatgg     360
ctattgtgat catgtggctc agccttgagt ctatattgag gtgcagacaa catagtccct     420
aaccacatgt gtgatcaagc aactttttg atgtccacag gtttataagt aggcaacatt     480
taagcaagaa aaaacacagg atcactattg agtcagctgc tgttgcctgt tactgag       537
```

<210> SEQ ID NO 3

```
<211> LENGTH: 517
<212> TYPE: DNA
<213> ORGANISM: Solanum lycopersicon

<400> SEQUENCE: 3
caaaatgctt cagctactgg ctaaatgaag tatgttctca acatattcac aagcttctgt    60
cttcgaagct caagaagtgt cggtattatc tgaattaaat agtaaagcaa agagatggtt   120
ttatgtttct taagcagcat ttcttagctt aacggccctc cagatatatg gtggacaaaa   180
tagaatccat tagatataac aaatgggatt agtataatga tcttttactt tgttagatga   240
tcatactaac agattgcaag ttaatcatat ccaacatatt ctgtagatat ttcacattgg   300
ctagcatgag gaaaggtcat gtaggaaatt gaatagagtt caattttggg aaaagttgca   360
ttgaagaagg taacttcaac aaacgtgtga aaaaatcaca tttgagttgc ccgctcacca   420
tcgtgattcc agtacgaact actcaaaaat ttacttttga gccttaaaca tcattttaag   480
ccttgaaaag ctgcttttga aaagatctaa gcaagat                            517

<210> SEQ ID NO 4
<211> LENGTH: 537
<212> TYPE: DNA
<213> ORGANISM: Solanum lycopersicon

<400> SEQUENCE: 4
ggagaatatt gtcactctat cagatagttc aaaactatcg gagaatgaaa tggtcaattc    60
ttctcacaag atattcatgc ctagttgcag tgtccgaatt aacataacat gctcaatttt   120
catatcttgc agcaaaattt atcattgaaa ctctctgaga tggaaacaga gaacaaagac   180
catattggaa agcttcaatc agacatgcag aaaaaggaag atgagattca tgttttacgc   240
aaggaaattg acaattacac ggaaacagtg gattcactgg agaagcatgt tacagagatt   300
aacaataaat tggaggagaa agatcagctt gttcaggaac ttcaggacaa ggagaagcag   360
ttggaagctg acagagaaaa ggttttttact acggatactt ttagttctac aaattctatt   420
ataaccaata caatgtgttc aagtgactag tgttttgcac cttgttgcag attcaggcat   480
cttttgcttg ctgctgaaagc aagctcacag aatccaaaaa gcagtatgat cagatgt      537

<210> SEQ ID NO 5
<211> LENGTH: 478
<212> TYPE: DNA
<213> ORGANISM: Solanum lycopersicon

<400> SEQUENCE: 5
aattcggagc tcactgcttc taatcctcag tgagacttat tttctacata ttaaacaata    60
agaaatttac gaaggaatat tatagactga attccttggt gacaagtatc aagacatctt   120
gaccaagttt aaagttttgt agtggcagtt cttttaagct ttacttgtgt gaggtagaca   180
tcaaggaaga taagtagcag ctactcttca cggagcagcc cataggacac tcaaattcac   240
tattgcgagg gtcaatctac caatttatgg aacgatacca gtaaagtcat ttttatgtaa   300
acatcagaca gcttttgact aagcagagac atgaataagt tctatttgtt agaagtcgaa   360
gagacaaata agttaatttc acctatgcta taaaagagga ctcttatagt tataaataca   420
gtacatttta ttaagggttc taattgttga ctatgatagc aagcatgccg tactaatt     478

<210> SEQ ID NO 6
<211> LENGTH: 503
<212> TYPE: DNA
<213> ORGANISM: Solanum lycopersicon
```

<400> SEQUENCE: 6

```
acattttgag aagacagga gttatgtatc gccatctggt gtgctccaag aacatgacag      60
atataaaaga ccgcggggtg caccagagaa atgttgcatt ggagcatatt gaacatcata     120
ggctcaatgg aattgtttac tttgcaatg atgataatat ctactcactt gagttgtttg     180
agagcattag atcgatcaag taagttgaga ttcatcagtc ttgtttacat gacttgtctt    240
tgttttgtcc tgctgtgagc atgttcagga tgatgttatg tgctttatgt agatgttcaa    300
gtcgataata gtgaatagtc tagagctatt tcacatatat tacaacttca ctaacaaatt    360
cttttcctgg tgtcctcggt tcatcactct tcatagttat aagaataaca gttgtagatt    420
agaccactgg tcgtgtgatt tttggactta attattatct caattcttcc tcaaaatagc    480
agtccttaga ttagaagctg agg                                            503
```

<210> SEQ ID NO 7
<211> LENGTH: 454
<212> TYPE: DNA
<213> ORGANISM: Solanum lycopersicon

<400> SEQUENCE: 7

```
ctttttttt ttttttatat attgtggtat agattattat ataataacaa ggtgaattaa      60
catgagaaat gaataattgt cacattcttg ttctgtccat tttccagtag cggctagttg    120
gaaaatttgt tgtaacatgt aacacaggct gtccacattc tactccagag agaaagttgg    180
taagtagtgg gggcaaaaga tagagacccc aatagctatc aattcacttt gttgacaatc    240
aagatttgag aaaaaagatc aaaactttac caacttagat agctccataa tcaactgtag    300
gtacaattct ttagtgaaat tgcggcgttc atcttctggg gacgaagagt aagtagacaa    360
tcaattgtct tgtagaactt gggctttacc attttcccta ggacataagc tcttgatcga    420
agcttgaagt ttaattttag tggcactggt aatg                                454
```

<210> SEQ ID NO 8
<211> LENGTH: 496
<212> TYPE: DNA
<213> ORGANISM: Solanum lycopersicon

<400> SEQUENCE: 8

```
tttttttttt ttttttagcca aaatgcatac aaaaactgat tcagaagata cgagcttggc     60
tccttcgtcg ccggacaata gagggccgac ggcgtattac gttcagagtc cgtcacgtga    120
ttctcacgat ggcgagaaga caacgacgtc gtttcactct actcctgtta tcagtcccat    180
gggttctcct cctcactctc actcatccgt cggccgtcac tcccgtgatt cctcttcctc    240
cagattctcc ggctccctca gcctggatc tcagaagatt ttacccgacg ccgccggagg    300
cgtcggcggc cgtcaccacc gcaaagggca gaagccctgg aaggaatgtg atgttatttg    360
aggaagaagg actacttgaa gatgatagat ccagtaaatc tcttccacgt cgttgctatg    420
tccttgcttt tgttgttgg tttcttcgtc ctttcctcct tctttgctct catcctttgg    480
ggtgctagtc gacctc                                                    496
```

<210> SEQ ID NO 9
<211> LENGTH: 26
<212> TYPE: DNA
<213> ORGANISM: Artificial Sequence
<220> FEATURE:
<223> OTHER INFORMATION: PCR primer

<400> SEQUENCE: 9

```
tcatcatcaa ctatcgtgat gctaag                                            26

<210> SEQ ID NO 10
<211> LENGTH: 23
<212> TYPE: DNA
<213> ORGANISM: Artificial Sequence
<220> FEATURE:
<223> OTHER INFORMATION: PCR primer

<400> SEQUENCE: 10
acgcttgcga gccttcttga gac                                               23

<210> SEQ ID NO 11
<211> LENGTH: 479
<212> TYPE: DNA
<213> ORGANISM: Solanum lycopersicon

<400> SEQUENCE: 11 ctttttttt ttttcaacac aaacaaaatt tcattatatt gtcaggtagc acactacatc        60
tttacactgt catcaaacga ccagagactt gagaacgttt taagagattc attttccggg      120
gacaaagttt gtggcgaaag cccaggcatt gttgtttacg gggtctgcaa ggtggtcagc      180
aaggttctcc aatggaccct ttccggtgac aatagcttga caaagaatc caaacataga       240 gaacatagca agtctaccgt tcttgatctc ctttaccttg agctcagcaa atgcctctgg      300
gtcttcagca aggcctaatg ggtcgaagct gccaccaggg tagagtgggt cgacaacctc      360
accaagaggt ccaccagcaa tacggtatcc ctcaacagct cccatcaaca caacttggca      420
agcccagatg ccaagatgc tttgtgcatg accaagcttt ggggttgccca agtagtcaa      479

<210> SEQ ID NO 12
<211> LENGTH: 495
<212> TYPE: DNA
<213> ORGANISM: Solanum lycopersicon

<400> SEQUENCE: 12
ctggtgatta cgggtgggat accgctggac tttcagcaga ccctgaaact tttgccaaga      60
accgtgaact tgaggtgatc cactgcagat gggctatgct tggtgctctt ggatgtgtct     120
tccctgagct cttggcccgt aatggtgtca agttcggtga ggctgtgtgg ttcaaggccg     180
gatcccagat cttcagtgaa ggtggacttg actacttggg caacccaagc ttggtccatg     240
cacaaagcat cttggccatc tgggcttgcc aagttgtgtt gatgggagct gttgagggat     300
accgtattgc tggtgggacc tcttggtgag gttgtcgacc cactctaccc tggtggcagc     360
ttcgacccat taggccttgc tgaagaccca gaggcatttg ctgagctcaa ggtaaaggag     420
atcaagaacg gtagacttgc tatgttctct atgtttggat tctttgttca agctattgtc     480
accggaaagg gtcca                                                       495

<210> SEQ ID NO 13
<211> LENGTH: 500
<212> TYPE: DNA
<213> ORGANISM: Solanum lycopersicon

<400> SEQUENCE: 13
tgctttgaga cagatgtctc tcattaagtg actgaagctt tcttctagtt ggctagcata     60
ttcattttca gcatataatc tgtatcatga acaaaattgc gacagtattg aatttttatt    120
gttgaatagt cttttattta tccccgaagt tgagggtgga acttcacttt tctgttgatc    180
cttgcttgct gttttttgtaa acaaaaaagc gtcacccatt atttttcttt tattctttct    240
```

```
aggttgggac taagattttt tgaaatgaga aaggtattcg ctaccttgag ggctgtggtt      300
gaagtgatgg agtatctgag caaagatgca gctcctgatg gtgtgggaag gcttataaag      360
gaggagggag tatttccttt catttctttg tatttccgtg tgtgtatagt ccggaactgg      420
ttccctactt atgaattctt tcatggtttg gtcaattgag aaggatcaag aaatctgatg      480
ctactttatc atgggaactt                                                  500

<210> SEQ ID NO 14
<211> LENGTH: 525
<212> TYPE: DNA
<213> ORGANISM: Solanum lycopersicon

<400> SEQUENCE: 14
gcttgcatgc ctgcagagtg gtcatacaat aaaaggtaaa aatcaacatt cttacctctg       60
gaaagaaacc aatagcattg gtcaatgatg ctgcctctag aggaacaata ttgtatggtg      120
caagttcccc tgataaagta gcatcagatt tcttgatcct tctcaactga ccaaaccatg      180
aaagaattca taagtaggga accagttccg gactatacac acacggaaat acaaagaaat      240
gaaaggaaat actacctcct cctttataag ccttcccaca ccatcaggag ctgcatcttt      300
gctcagatac tccatcactt caaccacagc cctcaaggta gcgaatacct ttctcatttc      360
aaaaaatctt agtcccaacc tagaaagaat aaaagaaaaa taatgggtga cgctttttg      420 tttacaaaaa cagcaagcaa ggatcaacag aaaatctaag ttccaccctc aacttcgggg      480
ataataaaaa gactattcaa caataaaaat tcaatactgt cgcaa                     525

<210> SEQ ID NO 15
<211> LENGTH: 456
<212> TYPE: DNA
<213> ORGANISM: Solanum lycopersicon

<400> SEQUENCE: 15
aactctgctc tgccaatagt agtcaggcag atcaagatgc tcaaaatttt ctatttgaat       60
tggaagcatc aagatggttc ttagcattta ttttagaaag actaaccata ttatcaaata      120
accagactga gacgcacaca aaagtttccc tctattattt ttataatgat gtgaagatgc      180
tacataatga gtacactttg ccttacttta ctgcagatgg acctaccagg cccaaacgga      240
catgtagcta tgcagaaaga gcaaccgcta tgaatgtctc aaactgttgg cctaggcgat      300
cagcacagat gatgaatctg gaagtacatt ccaagaagga agctggagc gtgggaacta      360 accagatgca gggatgaat ccacaccttt cagttgatca tctgaaggga aaactaagaa       420
ttttcatgag aaaatgactg gctatttca actttg                                456

<210> SEQ ID NO 16
<211> LENGTH: 562
<212> TYPE: DNA
<213> ORGANISM: Solanum lycopersicon

<400> SEQUENCE: 16
ttcaatgcat ttaagctcaa aaaaacaaag ctgtaggaag gagcatatta gtagcctaac       60
tctgctctgc caataatagt taagcagatc aagatgctca aaattttcta attgaattgt      120
tagcatcaag atgcttctta gcatttattt tagaaagatt aaccatatta tcaaataacc      180
agacagagac gcacacaaaa gtttcaatct attattttta taatgatgtg aaaatgctac      240
ataatgagta cactttccct tactttactg cagatggacc taccaggccc aaacggtcat      300
gtagttatga cagaagaaca acagtatgaa tttctcaaac tgttggccaa ggtgatcagc      360
```

```
aaagattatg aatttggaag tacattccaa gaggaaagct ggagcatcgt aactaaccag    420
atgcagggga tgaatccaca cctttcagtt gatcatctga aggcaaaact aagaattttc    480
atgagaaaat actggttatt ttcaactttg ttggccagac gaggagtcca atgggataga    540
aggactaact caatgacgta tg                                             562

<210> SEQ ID NO 17
<211> LENGTH: 422
<212> TYPE: DNA
<213> ORGANISM: Solanum lycopersicon
<220> FEATURE:
<221> NAME/KEY: misc_feature
<222> LOCATION: (2)..(2)
<223> OTHER INFORMATION: Wherein N is G, A, T or C
<220> FEATURE:
<221> NAME/KEY: misc_feature
<222> LOCATION: (10)..(12)
<223> OTHER INFORMATION: Wherein N is G, A, T or C

<400> SEQUENCE: 17
cnagctcgan nnaccctcac taaagggaac aaaagctgga gctccaccgc ggtggcggcc     60
gctctagaac tagtggatcc cccgggctgc aggctcctcc attgaaaagg gaatcaagtt    120
tgccaaagaa aactaaaaaa acaaaattat ggtctagttt tctatagtga cagttttgga    180
tcttttgggg tcaattgttt ttgtatcctt tgcaagtttc ttgcagccgg aggcttagat    240
ttagctcttt tgatattata cccaacattt ctacaaaata atgtatggca aactgggggc    300
ctatcccatt tgccttagtg tggaggtgtt attctcacat gaatcgtttt ccaattatgg    360
ttagtagcag acaattgatg caaaatgaag aaatgttcat gaccaaaaaa aaaaaaaaaa    420
aa                                                                   422

<210> SEQ ID NO 18
<211> LENGTH: 458
<212> TYPE: DNA
<213> ORGANISM: Solanum lycopersicon

<400> SEQUENCE: 18
aatgaagttc agttgataag ctaaatggtg gaaatactaa ttttaattga cagtaacttt     60
gcatttcaag gtccatacca aaacatttgc taacaccagt tgctttgtca acgaaaacct    120
tggcactcaa aaccctacca aaaggctgaa atgcatttgc aagctcttga tcaccaaatt    180
cttgaggaat atggtaaata aatagattag caccaggtgg acctgtaaac agcaaaatcg    240
tttttgataa gtacaggttt atttctacat gttcaactac cactgccaag tacactagtt    300
caagtgacat ctccaccact taattgcata aagctttacc aacgacaaat ataacaaact    360
tgtgcaagta atttgagttc ctgtctatac agtccagaat ctccatatgc tgctcatctc    420
acaatgttgg ttaaggaaat ttgtcaagta aagttcaa                            458

<210> SEQ ID NO 19
<211> LENGTH: 382
<212> TYPE: DNA
<213> ORGANISM: Solanum lycopersicon

<400> SEQUENCE: 19
catcttcaag tgtcagctca agtacagggg gtcaggttga aggttgttga acatttattt     60
tgtgaccttt ttagctctag aatttctgta gctaatcaag tacagtccca taacctaggg    120
gctgttaggg ttttctgctg aatgaggctg cttgtcttta ttttggttaa ttattttctg    180
gaaattgttc ctcgtcatag agaatagaag tagaagaaga agaagatagt ataatctatt    240
```

-continued

| | |
|---|---|
| atatttgttt tttacttaat ttataaagat tccataaatg catgtgatct ttgatcaatg | 300 |
| atatcttata caagtgtatc actagaatct attatatttg gatttactta ttttatatag | 360 |
| gatttcataa acgcatgtga tc | 382 |

<210> SEQ ID NO 20
<211> LENGTH: 331
<212> TYPE: DNA
<213> ORGANISM: Solanum lycopersicon

<400> SEQUENCE: 20

| | |
|---|---|
| tttttttttt taaaaattca aactccaatt atttgcagta taaaactaca gatacaaatc | 60 |
| ccagtacatg gtttgaggca cgataataag gtgctgatga aatccaagac atgagttcac | 120 |
| aatacattac tgaccaatat atttacaaag attagggtaa tggcagtaaa atcgctgatt | 180 |
| acagacaaca ttcttgggat atatttcatc ttaaagatta ggattagtag tatgtgtggc | 240 |
| agtcacagta gagaccatgg catcaactcc gcagatattg tgacccctgc agatcttgta | 300 |
| atatccgtgt tctccccaag tctttcccca a | 331 |

<210> SEQ ID NO 21
<211> LENGTH: 331
<212> TYPE: DNA
<213> ORGANISM: Solanum lycopersicon

<400> SEQUENCE: 21

| | |
|---|---|
| ttggggaaag acttggggag aacacggata ttacaagatc tgcagggtc acaatatctg | 60 |
| cggagttgat gccatggtct ctactgtgac tgccacacat actactaatc ctaatctta | 120 |
| agatgaaata tatcccaaga atgttgtctg taatcagcga ttttactgcc attacccta | 180 |
| tctttgtaaa tatattggtc agtaatgtat tgtgaactca tgtcttggat ttcatcagca | 240 |
| ccttattatc gtgcctcaaa ccatgtactg ggattgtat ctgtagtttt atactgcaaa | 300 |
| taattggagt ttgaattttt aaaaaaaaaa a | 331 |

<210> SEQ ID NO 22
<211> LENGTH: 478
<212> TYPE: DNA
<213> ORGANISM: Solanum lycopersicon

<400> SEQUENCE: 22

| | |
|---|---|
| ctagttggat tgaaacaatt gggaatatag tgtaggaaga cttcggggca attatctgct | 60 |
| ttcttctata tcaaactggg tctattgaag aattacaaac tggaccttaa atctttttgcc | 120 |
| agttttgta aaattgataa acttttgata ttttattatg gaaattcaaa atatatctta | 180 |
| atagtagctt gttaatttat ttcaagagac ccttttcatt gttcatagtt cattatcatc | 240 |
| cccttatcag tagtgcacca agggtgtgac ctagtggtca attaagtatg aatcatgagt | 300 |
| cttagacaga aacactaggt gattttcttc catgtgtcct agcctcttag gcttggtgga | 360 |
| tagaggaggt atcctgtctt tccccttcc agaaattcat agcattattt tctgttcttt | 420 |
| attgataaat tattcattag aacagttatt agaaatgtgg aactggttga ggtaggcg | 478 |

<210> SEQ ID NO 23
<211> LENGTH: 493
<212> TYPE: DNA
<213> ORGANISM: Solanum lycopersicon

<400> SEQUENCE: 23

| | |
|---|---|
| cagaacagag aacatgtaaa gttgttcaac taatgagcat atttagaaaa acttagtggc | 60 |

```
tatcaatagt tggcaatatg aaaactaaga tagtgtggtc acctgttgat caatttcttc      120
ttcaataggc atcttgtcag cttcctcttg taacaaggct ttcatttgtg acttgagaat      180
atatccagga ggaagtgcat gcctgtaatg gcattcttta ccatttggac aggcccagaa      240
ccaaccgtac tgcttttcct ccacagcatc caaaagaat ttacataccct gcatataaac       300 caaatcataa gcttgattta tgaaacgagc actgcattca tgtttggcaa tatttgactg      360
gaggaggagt tttaaagggg gaaattaaga ctatagacac atacactaaa tatgcataaa      420
acgccaaaag taccctggtt tcctatccag ttaaggcaac agtagcagaa atgagtgtt       480 gtaatgagtc aat                                                         493

<210> SEQ ID NO 24
<211> LENGTH: 465
<212> TYPE: DNA
<213> ORGANISM: Solanum lycopersicon

<400> SEQUENCE: 24
tattcaagaa atattgtgt agtgttctcc aatattcaac tatttaagtt caatggatct        60
agacacacaa tattattaat tctcgtcgcc gatgggatgg ttgagtgatt gaagcatagg      120
aataacatcc tggagattct aggtttggac tccagtttga acataagtgt gagcccatct      180
gctttatctt acaagttcaa ttcaaacttg tgtgagtggg ccatagtaga tccatgcaaa      240
atagtggtta tgacgctatg gtgagttcat gagaagaatt attgttcctt aggaacagtg      300
acaggaaatt caatggtcaa ataacatcaa gaagactttt tggattagtt actgagtgat      360
gttcagaaga gggactaaat atctaacatg cccccctcaag ctccagatgg taaagcaact      420
tgagtttgag ttactagaat ttagtaacat aaaaaggttt tccat                       465

<210> SEQ ID NO 25
<211> LENGTH: 393
<212> TYPE: DNA
<213> ORGANISM: Solanum lycopersicon

<400> SEQUENCE: 25
tttccacaca cacaaaaaaa acatcttgaa cacactgtaa tcccctctt catcaaattc         60 tcctgtgtca acacaacttc cttagccagt aaccacacaa cttccctctt ctgaacatta      120
caaagtcgct gatccagaaa gtcttgttct tgatgctatt tgaccattga atttcctgtc      180
actatccaac atgaatagtg tttgtaggga ataaattgaa atcagattac aaggatccaa      240
atatccatcc ccaacaatgt actgtttatg cccgaaggtg aggataaaaa gatgaaaac       300 ctttttatgt tactaaattc tagtaactca aactcaagtt gctttaccat ctggagcttg      360
agggggcatg ttagatattt agtccctctt ctg                                    393

<210> SEQ ID NO 26
<211> LENGTH: 544
<212> TYPE: DNA
<213> ORGANISM: Solanum lycopersicon

<400> SEQUENCE: 26
tgcagttgaa ttcgtcttct taacactatt ctcttatgct gtgcatcaag acaaccaccc       60
tcattgggcg gtcattgctt cttcaggcat gaccctacag ttagtacatt tggttttacc      120
aaatcttctt ctaaggataa atctatttga ctatggttca ctctctaaat cataagctga      180
aacaacatca acatacccccg tgtaaatcat aagctaaaac aaactctaga atagccttac      240
ctcatcattc ctaggaccat aattatatct atacttagtc aaaatcatca taaaatttac      300
```

```
ctacaagacc atttagatct cacctgatta agatttgttg gttactcgta atcccttgaa    360
ctaaggtgta acatcttaac ccctcctttt gagtatttat accatcatat tttgaaactt    420
ctcgtaggtt catatgtttc ttttggtact tgttagtata gcttggagtg ggacccaagg    480
ggctccagtg agttctagac aagaaaaacg agatttgaac attgcagatt ttatgttttc    540
tggt                                                                 544
```

```
<210> SEQ ID NO 27
<211> LENGTH: 484
<212> TYPE: DNA
<213> ORGANISM: Solanum lycopersicon

<400> SEQUENCE: 27
ctttgtttgc ttgcaagaca gagatttata cacgctaatg ctatctttt gtgtcattaa      60 cagctagttt gatttgcttg gttaatacag ttatggtaga tagagaagat agtttcaaaa    120
tagaaagaat gatgtagaca gcattaatga atctttctcc ttacaattgt acctttgaca    180
aggaatccac cttttatagg tagtttggtg agtttgatgg aagattgtgg ttgaatctgg    240
ttgagtcata gacactactt gtacattctt ttatgacact gacttgatgt tgtaagagtg    300
aaatgtatag acttatcaac aaataacaga gtagaaataa aagtaggttg aagatagctt    360
cttgtttggt tctaacttgc tcctttgttg actgatatga taacattgtg tcaatataag    420
atgattcaaa atgttgcctg aatttttatg aaattgatat tcatcgtcca gtttagagag    480
ttct                                                                 484
```

```
<210> SEQ ID NO 28
<211> LENGTH: 440
<212> TYPE: DNA
<213> ORGANISM: Solanum lycopersicon

<400> SEQUENCE: 28
actgactaag ctgctggatt tgattagccg aaggaattta cttttggtta catcttgctc     60
catcaccttt gtctttatct aggtcaatct tgtaccatag atgcaaataa cactatgaac    120
agattaacaa tgtcttgagg aggattaggc tgtcaacagc ctgcataata acaggaacaa    180
cattggcgtt tgtttgcatc agttactgtg actctgatta aggagaaaaa tgtggcatcc    240
tctgcttata ctgtcagtgt gtatacttgt caggttaagt tggttgctat aatctttaat    300
aattcttgat tttgtggttg tttctgaagt aaattgatat gtgggccttt gagctggagg    360
agatggtact ttagctattc actaacaatc gtttacctta aaaatgttat tctgtaagta    420
tctaaccaaa ttctgatcac                                                440
```

```
<210> SEQ ID NO 29
<211> LENGTH: 474
<212> TYPE: DNA
<213> ORGANISM: Solanum lycopersicon

<400> SEQUENCE: 29
tgcagacacc aaagaaacaa ttggttatat aaaaaacaat ccacaatcat tctctataga     60
agtcacgcaa agacactaca taacctccaa gtgcaatgaa gaggatgcag aataagaagc    120
tcagaacttc caaagaaaaa ggtgactgaa ataagtttg ctgaaaaggt acaaggcaag    180
ttctaattct caactagctt taggtataca ctaaagaaaa ggaaaataaa ttccaaacag    240
aagtttccat cctacctagt acataaaaga aaaggtaaa aaggaacata tggaagtgtt    300
cccctgttac ctaaactttt ggtgataaac agtaatcatg attaccccca cctcacacac    360
```

```
caccactaca gcacaaaaat tagaaatgtt gtatggacca tgatcaacca gccaagaatc    420
ccagaaggag aataaaggag ttctcttaat cacaagagga gaatatcatc tact          474

<210> SEQ ID NO 30
<211> LENGTH: 182
<212> TYPE: DNA
<213> ORGANISM: Solanum lycopersicon

<400> SEQUENCE: 30
gccccaaaac tcctgctgga ttttactgga tctccacttg ctgcggacat tgcttgcctc    60
cgacaatcat cttcccaact tcttcctttt tgtcttgaaa ttaatccctt gtacccattg    120
ctgcttctaa atgacctcct gcatcccggc ggatccacta ggtctaaagc tgccgccccc    180
gc                                                                  182

<210> SEQ ID NO 31
<211> LENGTH: 521
<212> TYPE: DNA
<213> ORGANISM: Solanum lycopersicon

<400> SEQUENCE: 31
ggattttgat gaacttgtat ctgtgcttct agctccacct aggatgagtt tggatttgta    60
cgattaacaa atgtttgagc tgaaagaatt aaatttgatt acacctgcct ttacatattt    120
ttgttgcgta aggattttct atgaagaata tatatgtatg tatgtgtaaa ggatgcacta    180
agcatctcgc attttgataa agaaatgaac tttgggctta actcaactcc aaaagttagc    240
tcatgaagtg aggatatcgc gtaagaccgt ataaggagac ctagaaccca tcccacaaca    300
atgtgtgact ccaacacatt cacgcaagtt ctggggaagg gttgcactcg taagggttgt    360
gatgtaggca gccataattg tgtgtaccca ttcgttagaa aactacactg tgcaagtgga    420
gttaaattgt atcttttttg gttttgtgtg agttgttcaa tccccttgac atgaaaaaaa    480
gaagcaaaat tcaagtataa tggtaaaagg ggattcaaaa t                       521

<210> SEQ ID NO 32
<211> LENGTH: 485
<212> TYPE: DNA
<213> ORGANISM: Solanum lycopersicon

<400> SEQUENCE: 32
ttgggtcagc catagtactt cgtgatatat ctctgacaga agatatctgc tcaagaccat    60
gaacaatacg gagacataag aaggaaagaa gttcagtgca gcacaaaatt ttaataagtt    120
aacttaaagg gggataagag gcaaaaccaa tataaaagtt tggacagaca aattttaatt    180
agtatcaaag agtgaatgat gctaaaagaa gagatgctta aatatctgat actataaagt    240
aagccatgac taattggtaa ttatgaatgg catatgatac gactatcagt tttgactgtt    300
gtctacaata atgatttcag aaacatatga tatatttcaa atagaattga ataacaacac    360
ttgttcaaat acctagctct cggaggcaga tccagaattt tagaaagtgg gtgcagtaaa    420
tcacaagagt acacctctgc tagaatgggt gtgtactgta acaaaacctg ttttgatatg    480
catat                                                               485

<210> SEQ ID NO 33
<211> LENGTH: 475
<212> TYPE: DNA
<213> ORGANISM: Solanum lycopersicon

<400> SEQUENCE: 33
```

```
actagcatct cttggaggat gctgaggtgt caagtggtgt tgaccactcg ttaccactga    60
ttcacagctg gtgtctttcg aagcaagctt cgtctgcaaa acaagaatca cactttaatc   120
ctctgttacc taaaaacaat agttgtttga tgtaatgaaa gaagaatttt cacttcaatg   180
atggaaagaa aatcttacag tttgagtttg cttgcgaaag tagccatttt catacaccag   240
ttgagaaact tgcttctgca atctatcatt ctcttccatt aatagcttgt tcattgctga   300
cagcttccta ttcacaccct gaagcctga tgactctttc ctctgttttt ccctacatct   360
atacaactca agaaacaat caattatact tcaaattaat tggggtcgct aaaaatgaat   420
cctttagact aacaacatcc cacaagtcct taccccctacc tcgcagaggt agaga       475
```

<210> SEQ ID NO 34
<211> LENGTH: 490
<212> TYPE: DNA
<213> ORGANISM: Solanum lycopersicon

<400> SEQUENCE: 34

```
tcagcaaaat gtcacacaga gagtacagta gtagagcaca gtagagtagg gagaagttgc    60
ctcaaaagag gaaagaaaa ggtaacgaac cacacatttg acagctcaaa accactttac   120
caatccaaac aaaaaatcat cacattatcc ctcccttctc tcctttctct attactctca   180
ttttccccaa gttcaggta cctttttcct aacataatcc gcccatagtg ttcatcattc   240
aagatctgtc cttttgagga gacttcattc cttactatgg tcttcttttt ttgatgattt   300
cttatgtgag atgttgaaaa ctggaagaa gtgataaaga taggaggttt ggttctggg   360 gtttgtttat tttgctttac aagggttaaa gattggatct ttttagttt tggtagatac   420 ccatgtctaa tcttgtttca gaattcaaaa ggttggtact ttactgtttt gcaagtggat   480
gacagaggag                                                          490
```

<210> SEQ ID NO 35
<211> LENGTH: 469
<212> TYPE: DNA
<213> ORGANISM: Solanum lycopersicon

<400> SEQUENCE: 35

```
ttaggtttt gtgtggttca acgttttgg ttttgatttt tatgtgtttt cttagttcct    60
tgcttcacca ttttgatggt attttgagtt tttgatgttc tgtcggcata aagtagtgat   120
ttttcagaca gtttggtatt atggagtatg tttcttttgct cttctctaat ttggattggt   180
tctgatttgt atatgcttgt tttagtttcg atggttttg agtttttgat gattcattgg   240
cacaaagtag tgattttca gactgttggg ttttgtgggg ttcccgtgct tgctcttcac   300
taatttggat tggttctgat ttgtatatgt tttagttttg atggttttg agttttgat   360 gattcatcgg cacaaagtag tgatctttca gacagttggg ttttgtgggg ttcacgtgct   420
tattcttcac tattctcggt tggtttgatt tgtaggtccg ttttagcat               469
```

<210> SEQ ID NO 36
<211> LENGTH: 502
<212> TYPE: DNA
<213> ORGANISM: Solanum lycopersicon

<400> SEQUENCE: 36

```
agaatataac aaaaaagcag ataaatcagt taattatgcc tcaatctcaa caagtgaata    60
acaaatccta tcagaagata tagtagacga taaacagtga aggtagaagc ctaactctat   120
gacattatct tgagacccaa aacacttcat caaagactca aagagaataa tttgttcacc   180
```

```
aagtactatt aactaattat caaaactaga attctcaaaa taaaaaataa caaatcttat    240
cagtcacatg gacattcatt aaacatcatg aagaagacaa caaggaagg tcaaaactgg      300 actccatggc acataagata ataacaaaag gtagtttaag gcctaaaaca cttcaaaaat    360
aaaatttatt caccagatat caataatatt atctgttctt ccttcattca tgagggcat    420 gcacaagaga caatatacat catttctcct tttactttt ctttcctgag gaagtaaaag    480
gagcagaaag cagatagaaa ga                                              502
```

<210> SEQ ID NO 37
<211> LENGTH: 45
<212> TYPE: DNA
<213> ORGANISM: Artificial Sequence
<220> FEATURE:
<223> OTHER INFORMATION: PCR primer
<400> SEQUENCE: 37

```
gtatactcaa cagagcttca gacgtgtaga tacctgcact ctcag                    45
```

<210> SEQ ID NO 38
<211> LENGTH: 40
<212> TYPE: DNA
<213> ORGANISM: Artificial Sequence
<220> FEATURE:
<223> OTHER INFORMATION: PCR primer
<400> SEQUENCE: 38

```
aactctacgc tgcactgctg ctgaagctca ccttgaggtg                           40
```

<210> SEQ ID NO 39
<211> LENGTH: 41
<212> TYPE: DNA
<213> ORGANISM: Artificial Sequence
<220> FEATURE:
<223> OTHER INFORMATION: PCR primer
<400> SEQUENCE: 39

```
cgaaatgtga ctattccaga ggtaatttgc acttcttgcc t                         41
```

<210> SEQ ID NO 40
<211> LENGTH: 43
<212> TYPE: DNA
<213> ORGANISM: Artificial Sequence
<220> FEATURE:
<223> OTHER INFORMATION: PCR primer
<400> SEQUENCE: 40

```
ttcatttgct ggacaggcag tctgtcatca aacgaccaga gac                       43
```

<210> SEQ ID NO 41
<211> LENGTH: 47
<212> TYPE: DNA
<213> ORGANISM: Artificial Sequence
<220> FEATURE:
<223> OTHER INFORMATION: PCR primer
<400> SEQUENCE: 41

```
atcatacctt ctctctccaa accctcgcca ttgctcactt taaactg                   47
```

<210> SEQ ID NO 42
<211> LENGTH: 51
<212> TYPE: DNA
<213> ORGANISM: Artificial Sequence
<220> FEATURE:
<223> OTHER INFORMATION: PCR primer -continued
<210> SEQ ID NO 43
<211> LENGTH: 44
<212> TYPE: DNA
<213> ORGANISM: Artificial Sequence
<220> FEATURE:
<223> OTHER INFORMATION: PCR primer

<400> SEQUENCE: 43
tccacagtta ttgcttcttg tttcgggtgt gtctgtttga cagc 44

<210> SEQ ID NO 44
<211> LENGTH: 42
<212> TYPE: DNA
<213> ORGANISM: Artificial Sequence
<220> FEATURE:
<223> OTHER INFORMATION: PCR primer

<400> SEQUENCE: 44
tgcagagctg taatatttag accggtctca gttgcaactc aa 42

<210> SEQ ID NO 45
<211> LENGTH: 46
<212> TYPE: DNA
<213> ORGANISM: Artificial Sequence
<220> FEATURE:
<223> OTHER INFORMATION: PCR primer

<400> SEQUENCE: 45
gcgagctcga attcaattcc aaccgggatt ttagtttttc cgatcc 46

<210> SEQ ID NO 46
<211> LENGTH: 43
<212> TYPE: DNA
<213> ORGANISM: Artificial Sequence
<220> FEATURE:
<223> OTHER INFORMATION: PCR primer

<400> SEQUENCE: 46
tttgtaccat gattgtccga tcggcattca tcattcaaca tgc 43

<210> SEQ ID NO 47
<211> LENGTH: 41
<212> TYPE: DNA
<213> ORGANISM: Artificial Sequence
<220> FEATURE:
<223> OTHER INFORMATION: PCR primer

<400> SEQUENCE: 47
tggaaagcca gacacacaga caggggtatc agtaggcagt g 41

<210> SEQ ID NO 48
<211> LENGTH: 40
<212> TYPE: DNA
<213> ORGANISM: Artificial Sequence
<220> FEATURE:
<223> OTHER INFORMATION: PCR primer

<400> SEQUENCE: 48
gcgatttggc tatctgggta aaccgaaagg cttttccaag 40

<210> SEQ ID NO 49
<211> LENGTH: 42
<212> TYPE: DNA

<400> SEQUENCE: 42
tgataaatgc tgggaagatt gactcatcaa cctggctcca tcttctattt g 51

```
<213> ORGANISM: Artificial Sequence
<220> FEATURE:
<223> OTHER INFORMATION: PCR primer

<400> SEQUENCE: 49
tggtgcaaca atcccgagc agttatcata atggctagct tg                    42

<210> SEQ ID NO 50
<211> LENGTH: 44
<212> TYPE: DNA
<213> ORGANISM: Artificial Sequence
<220> FEATURE:
<223> OTHER INFORMATION: PCR primer

<400> SEQUENCE: 50
acacaatgct aatcaacgtt atgctcatcc accgcccaca tttc                 44

<210> SEQ ID NO 51
<211> LENGTH: 39
<212> TYPE: DNA
<213> ORGANISM: Artificial Sequence
<220> FEATURE:
<223> OTHER INFORMATION: PCR primer

<400> SEQUENCE: 51
gcatgcctgc agagtggtca ttcgctacct tgagggctg                       39

<210> SEQ ID NO 52
<211> LENGTH: 46
<212> TYPE: DNA
<213> ORGANISM: Artificial Sequence
<220> FEATURE:
<223> OTHER INFORMATION: PCR primer

<400> SEQUENCE: 52
aattggcagg cttgagtgtt gctcccacca ttgttaccag gaccac               46

<210> SEQ ID NO 53
<211> LENGTH: 43
<212> TYPE: DNA
<213> ORGANISM: Artificial Sequence
<220> FEATURE:
<223> OTHER INFORMATION: PCR primer

<400> SEQUENCE: 53
ttcctcactg cttggaccag ctagaacttg gcatcccttg aag                  43

<210> SEQ ID NO 54
<211> LENGTH: 43
<212> TYPE: DNA
<213> ORGANISM: Artificial Sequence
<220> FEATURE:
<223> OTHER INFORMATION: PCR primer

<400> SEQUENCE: 54
ctacacaatt gtcacagaag tggagatcat tggtatacag ctg                  43

<210> SEQ ID NO 55
<211> LENGTH: 45
<212> TYPE: DNA
<213> ORGANISM: Artificial Sequence
<220> FEATURE:
<223> OTHER INFORMATION: PCR primer

<400> SEQUENCE: 55
atgcattcta gaatgccttt tgtctccctg gctttctgca gcatc                45
```

<210> SEQ ID NO 56
<211> LENGTH: 40
<212> TYPE: DNA
<213> ORGANISM: Artificial Sequence
<220> FEATURE:
<223> OTHER INFORMATION: PCR primer

<400> SEQUENCE: 56
atggagagaa gctggaacac ttcttagagc ccaccagcac                40

<210> SEQ ID NO 57
<211> LENGTH: 42
<212> TYPE: DNA
<213> ORGANISM: Artificial Sequence
<220> FEATURE:
<223> OTHER INFORMATION: PCR primer

<400> SEQUENCE: 57
atgggctggg atcgtagtaa aaagcttgcg attcccataa ca             42

<210> SEQ ID NO 58
<211> LENGTH: 40
<212> TYPE: DNA
<213> ORGANISM: Artificial Sequence
<220> FEATURE:
<223> OTHER INFORMATION: PCR primer

<400> SEQUENCE: 58
caaagcaatg ggcaatggta cacagcagtt tcagtaggac                40

<210> SEQ ID NO 59
<211> LENGTH: 40
<212> TYPE: DNA
<213> ORGANISM: Artificial Sequence
<220> FEATURE:
<223> OTHER INFORMATION: PCR primer

<400> SEQUENCE: 59
gattttgccc cctctaccaa catcttttcc ttccctctgc                40

<210> SEQ ID NO 60
<211> LENGTH: 40
<212> TYPE: DNA
<213> ORGANISM: Artificial Sequence
<220> FEATURE:
<223> OTHER INFORMATION: PCR primer

<400> SEQUENCE: 60
ggaacaggtc aggacagcat tggctaactg acgaagacga                40

<210> SEQ ID NO 61
<211> LENGTH: 40
<212> TYPE: DNA
<213> ORGANISM: Artificial Sequence
<220> FEATURE:
<223> OTHER INFORMATION: PCR primer

<400> SEQUENCE: 61
catgcctagt tgcagtgtcc ttcagcagca agcaaagatg                40

<210> SEQ ID NO 62
<211> LENGTH: 40
<212> TYPE: DNA
<213> ORGANISM: Artificial Sequence
<220> FEATURE:
<223> OTHER INFORMATION: PCR primer -continued

```
<400> SEQUENCE: 62
caccaacaac tagcccttga aagcaattcc tccagcttca                              40

<210> SEQ ID NO 63
<211> LENGTH: 40
<212> TYPE: DNA
<213> ORGANISM: Artificial Sequence
<220> FEATURE:
<223> OTHER INFORMATION: PCR primer

<400> SEQUENCE: 63
gacggcgtat tacgttcaga ctagcacccc aaaggatgag                              40

<210> SEQ ID NO 64
<211> LENGTH: 38
<212> TYPE: DNA
<213> ORGANISM: Artificial Sequence
<220> FEATURE:
<223> OTHER INFORMATION: PCR primer

<400> SEQUENCE: 64
tgtcagcata ggcttttcca cggtcgggaa aatgaca                                 38

<210> SEQ ID NO 65
<211> LENGTH: 40
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (23)..(24)
<223> OTHER INFORMATION: Wherein X is G, A, T or C
<220> FEATURE:
<221> NAME/KEY: misc_feature
<222> LOCATION: (28)..(28)
<223> OTHER INFORMATION: Wherein X is G, A, T or C

<400> SEQUENCE: 65
atctcgggat catggttgac atnnccanag aaattccaaa                              40

<210> SEQ ID NO 66
<211> LENGTH: 42
<212> TYPE: DNA
<213> ORGANISM: Artificial Sequence
<220> FEATURE:
<223> OTHER INFORMATION: PCR primer

<400> SEQUENCE: 66
caagccatag aaattgccgt atgctctctc tgtgatggaa gc                           42

<210> SEQ ID NO 67
<211> LENGTH: 48
<212> TYPE: DNA
<213> ORGANISM: Artificial Sequence
<220> FEATURE:
<223> OTHER INFORMATION: PCR primer

<400> SEQUENCE: 67 caactttttcc aggttcattt tctcacacct acatgctact aaggggtc                    48

<210> SEQ ID NO 68
<211> LENGTH: 44
<212> TYPE: DNA
<213> ORGANISM: Artificial Sequence
<220> FEATURE:
<223> OTHER INFORMATION: PCR primer
```

<400> SEQUENCE: 68
ttggctgaag tgaagaaaag taaagggcat tgtaatatct gtcc                    44

<210> SEQ ID NO 69
<211> LENGTH: 41
<212> TYPE: DNA
<213> ORGANISM: Artificial Sequence
<220> FEATURE:
<223> OTHER INFORMATION: PCR primer

<400> SEQUENCE: 69
accagccccg gaagatttta gcggtcaact tcagcaacta t                       41

<210> SEQ ID NO 70
<211> LENGTH: 42
<212> TYPE: DNA
<213> ORGANISM: Artificial Sequence
<220> FEATURE:
<223> OTHER INFORMATION: PCR primer

<400> SEQUENCE: 70
ctacttgtct gccaaggatt accgtgccgt tcaagaagag tg                      42

<210> SEQ ID NO 71
<211> LENGTH: 40
<212> TYPE: DNA
<213> ORGANISM: Artificial Sequence
<220> FEATURE:
<223> OTHER INFORMATION: PCR primer

<400> SEQUENCE: 71
attgaagaat ggcggtgaag atgccaactt cttggcaaac                         40

<210> SEQ ID NO 72
<211> LENGTH: 38
<212> TYPE: DNA
<213> ORGANISM: Artificial Sequence
<220> FEATURE:
<223> OTHER INFORMATION: PCR primer

<400> SEQUENCE: 72
ttgggaatat agtgtaggaa gctggaaagg ggaaagac                           38

<210> SEQ ID NO 73
<211> LENGTH: 47
<212> TYPE: DNA
<213> ORGANISM: Artificial Sequence
<220> FEATURE:
<223> OTHER INFORMATION: PCR primer

<400> SEQUENCE: 73
caagaaaata ttgtgtagtg ttctccatcc ccctcttcat caaattc                 47

<210> SEQ ID NO 74
<211> LENGTH: 40
<212> TYPE: DNA
<213> ORGANISM: Artificial Sequence
<220> FEATURE:
<223> OTHER INFORMATION: PCR primer

<400> SEQUENCE: 74
atgatatcca cacccctgga atgcctcgaa attcaaatgc                         40

<210> SEQ ID NO 75
<211> LENGTH: 48
<212> TYPE: DNA

```
<213> ORGANISM: Artificial Sequence
<220> FEATURE:
<223> OTHER INFORMATION: PCR primer

<400> SEQUENCE: 75
agcgtcactc catacttgga ataaagcgtc actcaaaatg tacccaaa                48

<210> SEQ ID NO 76
<211> LENGTH: 44
<212> TYPE: DNA
<213> ORGANISM: Artificial Sequence
<220> FEATURE:
<223> OTHER INFORMATION: PCR primer

<400> SEQUENCE: 76
agctgccgtg tcctgtatca actcatgttc acgccacttt ctta                    44

<210> SEQ ID NO 77
<211> LENGTH: 39
<212> TYPE: DNA
<213> ORGANISM: Artificial Sequence
<220> FEATURE:
<223> OTHER INFORMATION: PCR primer

<400> SEQUENCE: 77
tagaatatgg gaagcgaaat ggagaggaag cgtaatagg                          39

<210> SEQ ID NO 78
<211> LENGTH: 43
<212> TYPE: DNA
<213> ORGANISM: Artificial Sequence
<220> FEATURE:
<223> OTHER INFORMATION: PCR primer

<400> SEQUENCE: 78
atcccaagta ccctcgcatt agtagccttc tttgtcccat cag                     43

<210> SEQ ID NO 79
<211> LENGTH: 38
<212> TYPE: DNA
<213> ORGANISM: Artificial Sequence
<220> FEATURE:
<223> OTHER INFORMATION: PCR primer

<400> SEQUENCE: 79
tgttctgtcg gcataaagtt gctaaaacgg acctacaa                           38
```

TOMATO PLANTS HAVING HIGHER LEVELS OF RESISTANCE TO *BOTRYTIS*

RELATED APPLICATIONS

This application is a continuation of PCT Application No. PCT/NL2007/050183, designating the United States and filed Apr. 25, 2007; which claims the benefit of the filing date of European Application No. EP 06075950.3, filed Apr. 25, 2006; each of which is incorporated herein by reference in its entirety for all purposes.

FIELD

The present invention relates to plant breeding and molecular biology. More specifically, the present invention relates to a method for detecting a quantitative trait locus (QTL) associated with resistance to *Botrytis cinerea* in tomato, to a method of producing a *Botrytis*-resistant tomato plant therewith and to *Botrytis*-resistant tomato plants thus obtained and parts thereof.

BACKGROUND

*Botrytis cinerea* is a necrotrophic pathogenic fungus with an exceptionally wide host range comprising at least 235 possible hosts. Because of its wide host range and because it affects economically important parts of the plant *B. cinerea* is a major problem in many commercially grown crops. Amongst growers, the fungus is commonly referred to as *Botrytis*. The cultivated tomato (*Solanum lycopersicum*; formerly *Lycopersicon esculentum*) is also susceptible to infection by *Botrytis* and the fungus generally affects stem, leaves and fruit of the tomato plant. In heated greenhouses the occurrence of infections by *Botrytis* on stems is particularly common.

*Botrytis* actively kills infected cells, causing soft rot, blights, leaf spot, damping-off and stem cancers. Affected leaves become covered with conidiophores and conidia, and subsequently collapse and wither. The fungus will grow from diseased leaves into the stem and produces dry, light brown lesions a few millimeters to several centimeters in length. Lesions may also form at pruning scars on the stem. The stem lesions may also be covered with a gray mold. In severe cases, the infection girdles the stem and kills the plant. Older, senescent tissue of a tomato plant is usually more susceptible to attack by *Botrytis* than younger tissue.

In order to prevent the development of *Botrytis* in greenhouse grown tomatoes, the temperature and relative humidity must be closely regulated. It is further important to provide water without wetting the leaves. For field grown plants, good drainage and weed control should be employed. Moreover, the nutrient levels of the plants must be kept high. However, these preventive measures cannot fully avert the occurrence of considerable yield loss in case of infection.

Fungicides are available for controlling *Botrytis* in both greenhouse and field grown tomatoes. Examples of some fungicides include Dowicide A® and chlorothalonil, which may also be applied to the tomato fruits after harvest. However, *Botrytis* is known to have developed resistance against several commonly used fungicides. In addition, the use of fungicides is undesired both from an economic and from an environmental perspective. Presently, there is a need for commercial tomato varieties that exhibit resistance to *Botrytis*.

Partial resistance to *Botrytis* has been found in several wild species of tomato (Egashira et al. 2000; Nicot et al. 2002; Urbasch 1986). These plants however do not produce commercial crop tomatoes.

WO 02/085105 describes a genetic region on chromosome 10 of the genome of *S. habrochaites* that is believed to be involved in partial resistance to *Botrytis*. The introgression of this genetic material into cultivated tomato varieties was shown to provide for cultivated tomato plants that are partially resistant to *Botrytis*.

Thus far, however, breeding programs aimed at providing resistance to *Botrytis* in tomato have had limited success. The reason for these poor results is at present not clear. For one part, this may be due to insufficient knowledge on the genetic basis and inheritance of *Botrytis*-resistance. For another part, this may be due to the lack of proper bioassays for assessing *Botrytis*-resistance levels in tomato plants obtained in breeding programs. The lack of knowledge and methods also complicates the selection of plants among both wild accessions and offspring plants that comprise genes involved in resistance to *Botrytis*.

In a previous study, the present inventors found that *Botrytis* resistance in tomato is inherited polygenically, and that this may partly explain the poor results in breeding for resistant plants.

It is an aim of the present invention to improve the success of breeding programs aimed at providing commercial tomato varieties that are resistant to *Botrytis*. It is a further aim of the present invention to provide for additional and/or improved resistance to *Botrytis* in commercial tomato varieties. It is yet another aim of the present invention to provide for additional genetic material in the genome of wild tomato accessions that is involved in resistance to *Botrytis* in such plants. Such additional genetic material may be used to broaden the basis for the production of *Botrytis*-resistant varieties of cultivated tomato.

SUMMARY

The present inventors have now found that in the genome of *S. habrochaites* genetic material is present on a number of chromosomes which were not previously identified as involved in resistance to *Botrytis*. In fact, the present inventors have successfully identified quantitative trait loci (QTLs) in the genome of a line of a wild relative of tomato, i.e. in *Solanum habrochaites* LYC 4/78. These additional QTLs were discovered by the use of introgression lines.

The inventors were subsequently able to produce *Botrytis*-resistant tomato plants by crossing plants from these *Botrytis*-resistant wild (donor) tomato lines with non-resistant recipient tomato plants. These plants exhibited a higher level of resistance than any cultivated tomato plant produced thus far.

The improvement over the prior art resides in the availability of additional screening criteria by which the breeding process can be monitored and directed. The offspring plants produced from a cross between a resistant wild *Solanum habrochaites* and a susceptible cultivated tomato can be selected for having one or more, or even all of the genomic regions involved in the resistance to *Botrytis* in the wild accession. As a result, a method of producing a tomato plant is provided with which the required genetic constitution can be better controlled. An advantage of the present method is that, in a genetic sense, the progeny can be made to resemble the wild accession more closely for the desired trait. Consequently, the resistance trait in the cultivated tomato plant can be more stably introduced therein, i.e. the possibilities are now provided for assessing which of the genomic regions can be easily introgressed and which are difficult to transfer into offspring plants, which of the genomic regions are essential, which are co-operative, and which can be used to further improve resistance levels in partially resistant lines of cultivated tomato.

By assessing the *Botrytis* resistance level in various introgression lines, each having a specific genomic introgression from *S. habrochaites* LYC 4/78, in relation to the presence of molecular markers of the donor plant, the present inventors were able to identify additional QTLs linked to *Botrytis*-resistance in the resistant wild tomato lines and thereby establish the location of multiple resistance-conferring DNA sequences in the genome. In the description below, a quantitative trait locus (QTL) associated with resistance to *Botrytis* in tomato will be addressed in short as a QTL for *Botrytis*-resistance or a QTL associated with *Botrytis*-resistance.

A total of 5 new QTLs for *Botrytis*-resistance were found in a wild tomato line of *S. habrochaites*. One QTL was located on chromosome 4, which was previously identified as having a QTL associated with resistance to *Botrytis*. Yet it was found that an area on this chromosome previously associated with the resistance contained in fact two separate QTLs. The other QTLs were identified on chromosomes 6, 9, 11 and 12. The new QTLs could all be linked to a quantitative parameter that reflected the capability of the plant to reduce the initial establishment of an infection, hereinafter referred to as the parameter for disease incidence (DI), as well as to a quantitative parameter that reflected the capability of the plant to slow the progression of infection, hereinafter referred to as the parameter for lesion growth (LG) rate. Again the presence of a QTL on chromosome 10, as reported in the prior art, could not be confirmed by the methods used. All QTLs tested thus far could be confirmed by assessing disease resistance in $BC_5S_1$ or $BC_5S_2$ (backcross 5, selfed once or twice) progenies segregating for the QTLs under investigation.

The present invention relates in a first aspect to a method of producing a *Botrytis*-resistant tomato plant, said method comprising the steps of:

a) providing a *Botrytis*-resistant donor tomato plant, preferably a *Botrytis*-resistant plant of the species *S. habrochaites*, more preferably a *Botrytis*-resistant plant of the line *S. habrochaites* LYC 4/78;

b) transferring nucleic acid from said donor plant to one or more *Botrytis*-susceptible recipient tomato plants, preferably a plant of the species *S. lycopersicum*, wherein said transfer results in the introduction of genomic material from the donor plant in the corresponding region of the genome of said one or more susceptible recipient plants;

c) selecting from amongst said recipient tomato plants (or from additionally selfed of backcrossed plant obtained with said recipient tomato plant; i.e. from recombinant plants obtained after said transfer) a plant that comprises within its genome at least one QTL for *Botrytis*-resistance derived from said *Botrytis*-resistant donor tomato plant, wherein said selection comprises detecting on chromosome 4, 6, 9, 11 and/or 12 of said recipient tomato plant at least one genetic marker linked to said at least one QTL for *Botrytis*-resistance wherein the location of said QTL on chromosome 4 of said plant is indicated by a genomic region comprising the genetic markers CT50, C2At1g74970, P14M49-283e, P14M48-74e, P14M50-67e, CT1739 and P14M50-85h on chromosome 4 of *S. habrochaites* or on chromosome 4 of *S. lycopersicum*, more preferably on chromosome 4 of *S. habrochaites* LYC 4/78 or on chromosome 4 of *S. lycopersicum* cv. Moneymaker.

In preferred embodiments, the location of said QTL on chromosome 6 of said plant is indicated by a genomic region comprising the genetic markers P22M50-188h, P14M48-521e, P15M48-386h, P18M51-199h, P18M51-103h, P22M50-103e, P18M51-388e, P15M48-395e, P22M50-124e, P14M48-160e and P22M50-513h on chromosome 6 of *S. habrochaites* or on chromosome 6 of *S. lycopersicum*, more preferably on chromosome 6 of *S. habrochaites* LYC 4/78 or on chromosome 6 of *S. lycopersicum* cv. Moneymaker.

In other preferred embodiments, the location of said QTL on chromosome 9 of said plant is indicated by a genomic region comprising the genetic markers P18M50-141, P14M49-240, TG254, TG223, TG10, P18M50-134h, P14M49-243h, P18M50-599, P14M60-222h, P22M51-417h, P14M50-174h, P14M60-157h, P14M60-107h, P15M48-138h, P14M48-113h, Tm2a, P18M51-146h, P14M48-282h and P14M50-276h on chromosome 9 of *S. habrochaites* or on chromosome 9 of *S. lycopersicum*, more preferably on chromosome 9 of *S. habrochaites* LYC 4/78 or on chromosome 9 of *S. lycopersicum* cv. Moneymaker.

In still other preferred embodiments, the location of said QTL on chromosome 11 of said plant is indicated by a genomic region comprising the genetic markers P14M60-215e, P14M61-173h, P14M50-307h, TG47, P14M50-29xCD, P18M51-358h, P18M50-27xCD, P18M51-136h, P22M50-488h, TG393, P14M61-396h, P22M51-235h and P22M51-174e on chromosome 11 of *S. habrochaites* or on chromosome 11 of *S. lycopersicum*, more preferably on chromosome 11 of *S. habrochaites* LYC 4/78 or on chromosome 11 of *S. lycopersicum* cv. Moneymaker.

In yet other preferred embodiments, the location of said QTL on chromosome 12 of said plant is indicated by a genomic region comprising the genetic markers CT19, TG68, P14M48-411e, P18M50-244h, P18M50-273h, P14M61-420h, P14M61-406h, P14M61-223h, P14M60-193h, P22M51-314h, TG565, P14M48-172h, P22M50-321e, P14M60-219e, P14M48-153h, P22M50-97h, TG296, P22M50-131h and P22M51-135h, preferably by a genomic region comprising the genetic markers P14M61-420h, P14M61-406h, P14M61-223h, P14M60-193h, P22M51-314h, TG565, P14M48-172h, P22M50-321e, P14M60-219e, P14M48-153h, P22M50-97h, TG296, and P22M50-131h on chromosome 12 of *S. habrochaites* or on chromosome 12 of *S. lycopersicum*, more preferably on chromosome 12 of *S. habrochaites* LYC 4/78 or on chromosome 12 of *S. lycopersicum* cv. Moneymaker.

The transfer of nucleic acid comprising at least one QTL for *Botrytis*-resistance, or a *Botrytis*-resistance-conferring part thereof, may very suitably be performed by crossing said *Botrytis*-resistant donor tomato plant with a *Botrytis*-susceptible recipient tomato plant to produce offspring plants.

A preferred selection method therefore comprises marker-assisted selection (MAS) (see e.g. Tanksley et al. 1998) of said introgressed DNA wherein one or more markers associated with said QTL are detected in offspring plants. MAS may for instance be performed by isolating genetic material from said offspring plants and determining the presence therein, by molecular techniques, of one or more donor plant markers. Alternatively, molecular marker detection methods may be used without prior isolation of genetic material. Optionally, in addition to the marker detection, a phenotypic test on *Botrytis* resistance may be performed in order to select suitable plants. A very suitable test therefore is the quantitative bioassay as described herein, whereby such parameters as disease incidence and/or rate of lesion growth are determined. The confirmation of the presence of at least one marker from a QTL for *Botrytis*-resistance in combination with the establishment of the presence of a resistant phenotype provides evidence for the successful transfer of nucleic acid comprising at least one QTL, or a *Botrytis*-resistance-conferring part thereof, from the donor plant to the recipient plant.

In an alternative embodiment of a method of producing a *Botrytis*-resistant tomato plant, the indicated transfer of nucleic acid may very suitably be performed by transgenic methods (e.g. by transformation), by protoplast fusion, by a doubled haploid technique or by embryo rescue.

In a preferred embodiment of a method of producing a *Botrytis*-resistant tomato plant, the donor plants are *Solanum habrochaites* LYC 4/78 and the nucleic acid transferred from these donor plants into recipient plants preferably comprises at least one QTL for *Botrytis*-resistance selected from the group consisting of the QTLs on chromosomes 4, 6, 9, 11 and/or 12 of *Solanum habrochaites* LYC 4/78 associated with *Botrytis* resistance, or a *Botrytis*-resistance-conferring part thereof.

In another preferred embodiment of a method of producing a *Botrytis*-resistant tomato plant, the method comprises the crossing of said *Botrytis*-resistant donor tomato plant with a *Botrytis*-susceptible recipient tomato plant to produce first generation offspring plants; selecting from among the first generation offspring plants a plant that comprises in its genome nucleic acid introgressed from said donor tomato plant, wherein said introgressed nucleic acid comprises at least one QTL, preferably two, more preferably more than two QTLs for *Botrytis*-resistance according to the invention, or a *Botrytis*-resistance-conferring part thereof; crossing said selected offspring plant with a suitable commercial tomato line to produce second generation offspring plants; selecting from among the second generation offspring plants a plant that comprises in its genome nucleic acid introgressed from said first generation offspring tomato plant, wherein said introgressed nucleic acid comprises at least one QTL, preferably two, more preferably more than two QTLs for *Botrytis*-resistance according to the invention, or a *Botrytis*-resistance-conferring part thereof, and optionally producing further generations of offspring plants. The mentioned preferably two, more preferably more than two QTLs for *Botrytis*-resistance that are introgressed in offspring plants may be QTLs for disease incidence, QTLs for lesion growth rate or a combination of these types.

In a most preferred embodiment, step c) comprises selecting a plant that comprises within its genome at least 4 QTLs for *Botrytis*-resistance selected from the group consisting of the QTLs on chromosome 1, 2, 4, 6, 9, 11 and 12 of *Solanum habrochaites*, preferably line LYC 4/78, associated with *Botrytis* resistance.

In another aspect, the present invention relates to a *Botrytis*-resistant tomato plant, or part thereof, obtainable by a method of the present invention.

The present invention further relates to a QTL for *Botrytis*-resistance in tomato, wherein said QTL is selected from the group consisting of the QTLs on chromosomes 4, 6, 9, 11 and 12 of *Solanum habrochaites*, preferably line LYC 4/78, associated with *Botrytis* resistance. These QTLs are located on positions of the genome not previously associated with resistance to *Botrytis*. Details of these QTLs are described in more detail herein below.

The alleles present on the positions of the genome indicated by these QTLs are an aspect of the present invention.

A QTL of the present invention may be in the form of an isolated, preferably double stranded nucleic acid sequence comprising said QTL or a resistance-conferring part thereof. Very suitably, the size of the nucleic acid sequence, which may for instance be isolated from the chromosome of a suitable donor plant, may represent a genetic distance of 1-100 cM, preferably 10-50 cM on said chromosome. Said nucleic acid may comprise at least 50, more preferably at least 500, even more preferably at least 1000, still more preferably at least 5000 base pairs. One or more nucleic acid sequences comprising a QTL or a resistance-conferring part thereof according to the invention may in turn be comprised in a nucleic acid construct, said construct may further comprise regions that flank said one or more nucleic acid sequences and which regions are capable of being integrated into a suitable vector for transfer of said one or more nucleic acid sequences into a suitable *Botrytis*-susceptible recipient tomato plant. The vector may further comprise suitable promoter regions or other regulatory sequences. The QTLs may also be in a form present within the genome of a tomato plant. The QTLs of the present invention preferably comprise at least one marker, preferably two, more preferably three, still more preferably four, still more preferably more than four markers associated with *Botrytis*-resistance selected from the group consisting of the markers of Tables 1-5 linked to said QTL.

The present invention relates in another aspect to a method for detecting a QTL for *Botrytis*-resistance, comprising detecting at least one marker linked to a QTL for *Botrytis*-resistance on chromosome 4, 6, 9, 11 and/or 12 of a suspected *Botrytis*-resistant tomato plant, wherein the location of said QTL on chromosome 4 of said plant is indicated by a genomic region comprising the genetic markers CT50, C2At1g74970, P14M49-283e, P14M48-74e, P14M50-67e, CT1739 and P14M50-85h on chromosome 4 of *S. habrochaites* or on chromosome 4 of *S. lycopersicum*, more preferably on chromosome 4 of *S. habrochaites* LYC 4/78 or on chromosome 4 of *S. lycopersicum* cv. Moneymaker.

In a preferred embodiment of a method of detecting a QTL of the present invention, the location of said QTL on chromosome 6 of said plant is indicated by a genomic region comprising the genetic markers P22M50-188h, P14M48-521e, P15M48-386h, P18M51-199h, P18M51-103h, P22M50-103e, P18M51-388e, P15M48-395e, P22M50-124e, P14M48-160e and P22M50-513h on chromosome 6 of *S. habrochaites* or on chromosome 6 of *S. lycopersicum*, more preferably on chromosome 6 of *S. habrochaites* LYC 4/78 or on chromosome 6 of *S. lycopersicum* cv. Moneymaker.

In another preferred embodiment of a method of detecting a QTL of the present invention, the location of said QTL on chromosome 9 of said plant is indicated by a genomic region comprising the genetic markers P18M50-141, P14M49-240, TG254, TG223, TG10, P18M50-134h, P14M49-243h, P18M50-599, P14M60-222h, P22M51-417h, P14M50-174h, P14M60-157h, P14M60-107h, P15M48-138h, P14M48-113h, Tm2a, P18M51-146h, P14M48-282h and P14M50-276h on chromosome 9 of *S. habrochaites* or on chromosome 9 of *S. lycopersicum*, more preferably on chromosome 9 of *S. habrochaites* LYC 4/78 or on chromosome 9 of *S. lycopersicum* cv. Moneymaker.

In yet another preferred embodiment of a method of detecting a QTL of the present invention, the location of said QTL on chromosome 11 of said plant is indicated by a genomic region comprising the genetic markers P14M60-215e, P14M61-173h, P14M50-307h, TG47, P14M50-29xCD, P18M51-358h, P18M50-27xCD, P18M51-136h, P22M50-488h, TG393, P14M61-396h, P22M51-235h and P22M51-174e on chromosome 11 of *S. habrochaites* or on chromosome 11 of *S. lycopersicum*, more preferably on chromosome 11 of *S. habrochaites* LYC 4/78 or on chromosome 11 of *S. lycopersicum* cv. Moneymaker.

In still another preferred embodiment of a method of detecting a QTL of the present invention, the location of said QTL on chromosome 12 of said plant is indicated by a genomic region comprising the genetic markers CT19, TG68, P14M48-411e, P18M50-244h, P18M50-273h, P14M61-

420h, P14M61-406h, P14M61-223h, P14M60-193h, P22M51-314h, TG565, P14M48-172h, P22M50-321e, P14M60-219e, P14M48-153h, P22M50-97h, TG296, P22M50-131h and P22M51-135h, preferably by a genomic region comprising the genetic markers P14M61-420h, P14M61-406h, P14M61-223h, P14M60-193h, P22M51-314h, TG565, P14M48-172h, P22M50-321e, P14M60-219e, P14M48-153h, P22M50-97h, TG296, and P22M50-131h on chromosome 12 of S. habrochaites or on chromosome 12 of S. lycopersicum, more preferably on chromosome 12 of S. habrochaites LYC 4/78 or on chromosome 12 of S. lycopersicum cv. Moneymaker.

In a still further aspect, the present invention relates to a Botrytis-resistant plant of the species S. lycopersicum, or part thereof, comprising within its genome at least one QTL, or a Botrytis-resistance-conferring part thereof, wherein said QTL is selected from the group consisting of the QTLs on chromosome 4, 6, 9, 11 and 12 of Solanum habrochaites, preferably line LYC 4/78, associated with Botrytis resistance, wherein the location of said QTL on chromosome 4 of said plant is indicated by a genomic region comprising the genetic markers CT50, C2At1g74970, P14M49-283e, P14M48-74e, P14M50-67e, CT1739 and P14M50-85h on chromosome 4 of S. habrochaites or on chromosome 4 of S. lycopersicum, more preferably on chromosome 4 of S. habrochaites LYC 4/78 or on chromosome 4 of S. lycopersicum cv. Moneymaker, wherein said QTL or said Botrytis-resistance-conferring part thereof is not in its natural genetic background, and wherein said plant optionally further comprises one or more additional QTLs, or Botrytis-resistance-conferring parts thereof, associated with Botrytis resistance selected from the QTLs on chromosome 1, 2 and/or 4 of Solanum habrochaites, preferably of Solanum habrochaites line LYC 4/78, wherein the location of said additional QTL on chromosome 4 of said plant is indicated by a genomic region comprising the genetic markers P18M51-169.5e, P18M51-305.4h, P14M60-262.9e, P14M61-292.7h, TG609, P14M48-345e, P14M48-177e and P18M50-147e on chromosome 4 of S. habrochaites or on chromosome 4 of S. lycopersicum, more preferably on chromosome 4 of S. habrochaites LYC 4/78 or on chromosome 4 of S. lycopersicum cv. Moneymaker.

In yet another aspect, the present invention relates to a method of producing a Botrytis-resistant inbred tomato plant. The method comprises the steps of producing a Botrytis-resistant tomato plant according to a method of the invention as described above, selfing said plant, growing seed obtained from said selfed plant into new plants; identifying plants that exhibit Botrytis resistance and possess commercially desirable characteristics from amongst said new plants, and repeating the steps of selfing and selection until an inbred tomato plant is produced which exhibits Botrytis resistance and possesses commercially desirable characteristics.

A method of producing a Botrytis-resistant inbred tomato plant may further comprise the additional step of selecting homozygote inbred tomato plants that exhibit Botrytis resistance and possess commercially desirable characteristics.

In a further aspect, the present invention relates to a Botrytis-resistant inbred tomato plant, or parts thereof, obtainable by a method of the invention.

In a further aspect, the present invention relates to a hybrid tomato plant, or parts thereof, that exhibits resistance to Botrytis, wherein said hybrid tomato plant is obtainable by crossing a Botrytis-resistant inbred tomato plant obtainable by a method of the invention with an inbred tomato plant that exhibits commercially desirable characteristics.

The invention further relates to a tissue culture of regenerable cells of the tomato plants of the present invention. In a preferred embodiment of such a tissue culture, the cells or protoplasts of said cells having been isolated from a tissue selected from the group consisting of leaves, pollen, embryos, roots, root tips, anthers, flowers, fruits, and stems and seeds.

The invention further relates to the use of a marker selected from the group consisting of the markers of Tables 1-5 for the detection of QTLs for Botrytis-resistance according to the invention, and/or for the detection of Botrytis-resistant tomato plants.

The Botrytis-resistant donor tomato plant used in methods of the present invention is preferably selected from the group consisting of Lycopersicon cerasiforme, Lycopersicon cheesmanii, Lycopersicon chilense, Lycopersicon chmielewskii, Lycopersicon lycopersicum, Lycopersicon habrochaites, Lycopersicon parviflorum, Lycopersicon pennellii, Lycopersicon peruvianum, Lycopersicon pimpinellifolium and Solanum lycopersicoides, more preferably, a wild tomato accession is used as the donor plant. Highly preferred donor plants are Solanum habrochaites, in particular Solanum habrochaites LYC 4/78.

The Botrytis-susceptible recipient tomato plant used in methods of the present invention is preferably a plant of the species Solanum lycopersicum, more preferably an S. lycopersicum cultivar that possess commercially desirable characteristics, or another commercial tomato line.

BRIEF DESCRIPTION OF THE DRAWINGS

FIG. 5 shows the position of the quantitative trait loci (QTLs) for resistance to B. cinerea originating from S. habrochaites LYC 4/78 with the linkage maps representing chromosome 12 (putative position of QTL provided as dark section). The QTLs on chromosome 12 decreases both lesion growth rate and disease incidence.

DETAILED DESCRIPTION

Definitions

Figure 1:
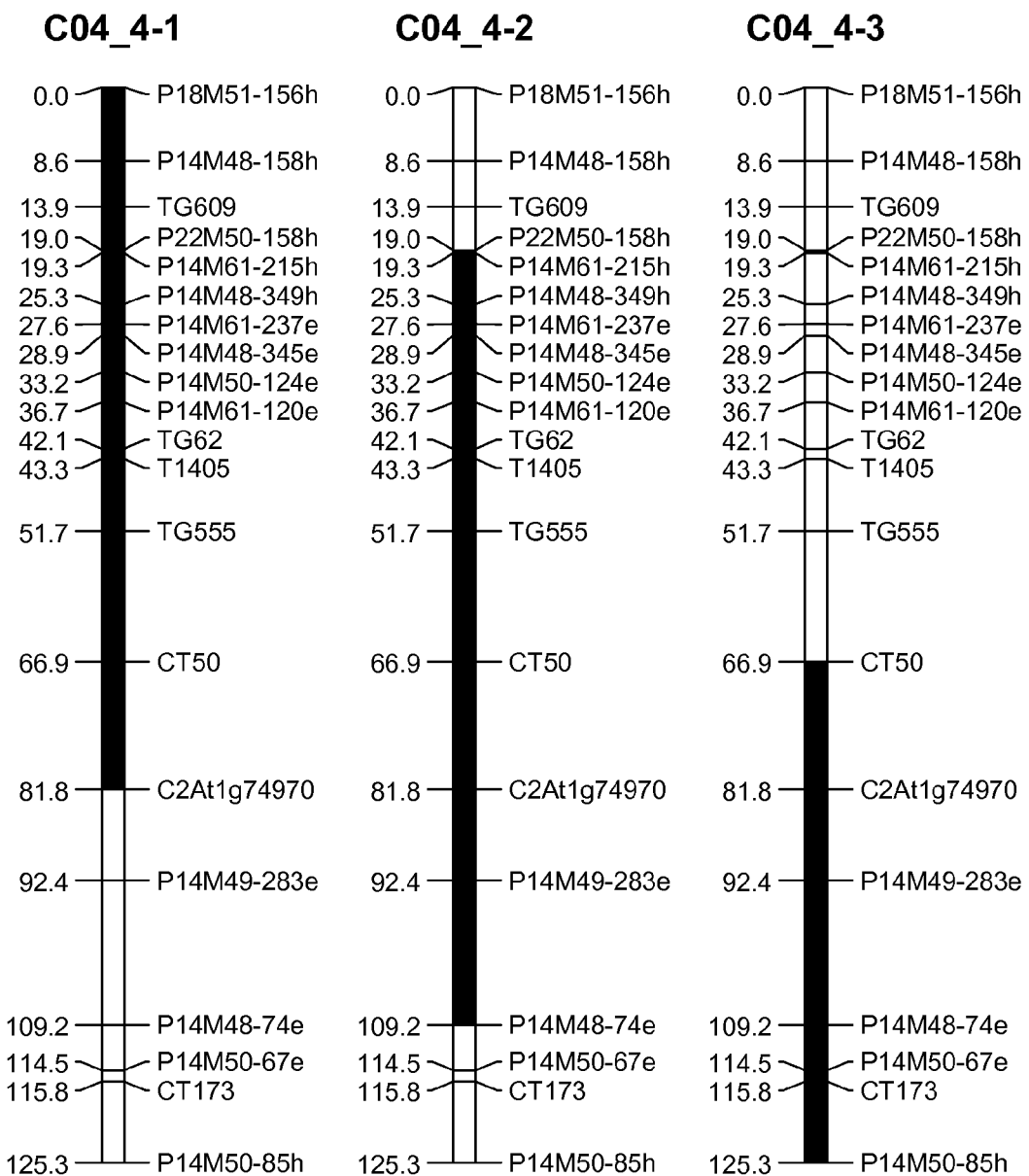
FIG. 1 shows the position of quantitative trait loci (QTLs) for resistance to B. cinerea originating from S. habrochaites LYC 4/78 with the linkage maps representing chromosome 4 (putative position of QTLs provided as dark sections). Map positions are given in cM. The data allow for putative identification of two separate QTLs, one centered around marker TG62 (see Example 1) and identified in IL 4-1 in Example 4, and another separate therefrom not including the marker TG62 but centered around marker P14M49-283e and identified in IL 4-3 in Example 4. The QTLs detected on chromosome 4 decrease both lesion growth rate and disease incidence. The codes for AFLP markers are more extensively described in Table 1. All markers indicated as associated to the QTLs in the Figures exemplifying the present invention may both individually as well as in combination be used as markers in aspects thereof.

As used herein, the term "*Botrytis*" means *Botrytis cinerea*, also known as gray mold or gray spot, a disease commonly found on the stem, leaves and fruit of tomatoes. It is generally considered that the plant pathogenic fungus *Sclerotinia sclerotiorum* has an infection mechanism similar to that of *B. cinerea* (Prins et al., 2000). Although *S. sclerotiorum*-infection in tomato is economically far less important than *B. cinerea*-infection, both fungi secrete a spectrum of proteases, plant cell wall-degrading enzymes, toxins as well as oxalic acid. Some of these factors are known to play a role in the infection strategy of both fungi. As a result, the mechanisms and genes that confer resistance to *Botrytis* are believed to be equally effective in providing resistance to infection by *S. sclerotiorum*. Therefore, when reference is made herein to "*Botrytis*-resistance", such resistance should be understood as including resistance to any fungus of the family of Sclerotiniaceae, preferably resistance to *S. sclerotiorum* and *B. cinerea*, more preferably resistance to *B. cinerea*.

As used herein, the term "allele(s)" means any of one or more alternative forms of a gene, all of which alleles relate to at least one trait or characteristic. In a diploid cell or organism, the two alleles of a given gene occupy corresponding loci on a pair of homologous chromosomes. Since the present invention relates to QTLs, i.e. genomic regions that may comprise one or more genes, but also regulatory sequences, it is in some instances more accurate to refer to "haplotype" (i.e. an allele of a chromosomal segment) in stead of "allele", however, in those instances, the term "allele" should be understood to comprise the term "haplotype".

A "gene" is defined herein as a hereditary unit consisting of a sequence of DNA that occupies a specific location on a chromosome and that contains the genetic instruction for a particular characteristics or trait in an organism.

A "locus" is defined herein as the position that a given gene occupies on a chromosome of a given species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "hybrid" means any offspring of a cross between two genetically unlike individuals, including but not limited to the cross between two inbred lines.

As used herein, the term "inbred" means a substantially homozygous individual or line In this application a "recombination event" is understood to mean a meiotic crossing-over.

As used herein, the terms "introgression", "introgressed" and "introgressing" refer to both a natural and artificial process whereby genes of one species, variety or cultivar are moved into the genome of another species, variety or cultivar, by crossing those species. The process may optionally be completed by backcrossing to the recurrent parent.

"Genetic engineering", "transformation" and "genetic modification" are all used herein as synonyms for the transfer of isolated and cloned genes into the DNA, usually the chromosomal DNA or genome, of another organism.

As used herein, the term "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

The terms "resistant" and "resistance" encompass both partial and full resistance to infection. A *Botrytis*-susceptible tomato plant may either be non-resistant or have low levels of resistance to infection by *Botrytis*.

As used herein, the term "plant part" indicates a part of the tomato plant, including single cells and cell tissues such as plant cells that are intact in plants, cell clumps and tissue cultures from which tomato plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation.

As used herein, the term "tomato" means any plant, line or population formerly known under the genus name of *Lycopersicon* including but not limited to *Lycopersicon cerasiforme, Lycopersicon cheesmanii, Lycopersicon chilense, Lycopersicon chmielewskii, Lycopersicon esculentum* (now *Solanum lycopersicum*), *Lycopersicon hirsutum, Lycopersicon parviflorum, Lycopersicon pennellii, Lycopersicon peruvianum, Lycopersicon pimpinellifolium*, or *Solanum lycopersicoides*. The newly proposed scientific name for *Lycopersicon esculentum* is *Solanum lycopersicum*. Similarly, the names of the wild species may be altered. *L. pennellii* has become *Solanum pennellii, L. hirsutum* may become *S. habrochaites, L. peruvianum* may be split into *S. 'Nperuvianum'* and *S. 'Callejon de Huayles', S. peruvianum*, and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense*, and *L. pimpinellifolium* may become *S. pimpinellifolium* (Solanacea Genome Network (2005) Spooner and Knapp; Worldwide Website: sgn.cornell.edu/help/about/solanum_nomenclature.html).

It is especially noted that *S. habrochaites* can be defined as a tomato species that carries hairy fruits, while *S. lycopersicum* is a tomato species carrying hairless fruits.

As used herein, the term "variety" or "cultivar" means a group of similar plants that by structural or genetic features and/or performance can be distinguished from other varieties within the same species.

The term "QTL" is used herein in its art-recognised meaning. The term "QTL associated with resistance to *B. cinerea* in tomato" as well as the shorter term "QTL for *Botrytis*-resistance" refer to a region located on a particular chromosome of tomato that is associated with at least one gene that encodes for *Botrytis*-resistance or at least a regulatory region, i.e. a region of a chromosome that controls the expression of one or more genes involved in *Botrytis*-resistance. The phenotypic expression of that gene may for instance be observed as a reduced rate of lesion growth and/or as a reduced disease incidence. A QTL may for instance comprise one or more genes of which the products confer the genetic resistance. Alternatively, a QTL may for instance comprise regulatory genes or sequences of which the products influence the expression of genes on other loci in the genome of the plant thereby conferring the *Botrytis*-resistance. The QTLs of the present invention may be defined by indicating their genetic location in the genome of the respective wild tomato accession using one or more molecular genomic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL.

The term "*Botrytis*-susceptible recipient tomato plant" is used herein to indicate a tomato plant that is to receive DNA obtained from a donor tomato plant that comprises a QTL for *Botrytis*-resistance. Said "*Botrytis*-susceptible recipient tomato plant" may or may not already comprise one or more QTLs for *Botrytis*-resistance, in which case the term indicates a plant that is to receive an additional QTL.

The term "natural genetic background" is used herein to indicate the original genetic background of a QTL. Such a background may for instance be the genome of a *Botrytis*-resistance wild accession of tomato. For instance, the QTLs of the present invention were found at specific locations on chromosomes 4, 6, 9, 11 and 12 of *Solanum habrochaites* LYC 4/78. As an example, the *Solanum habrochaites* LYC 4/78 represents the natural genetic background of the QTLs on chromosomes 4, 6, 9, 11 and 12 of *Solanum habrochaites* LYC 4/78. Also the *Solanum habrochaites* LYC 4/78 represents the natural genetic background of said QTLs. Conversely, a method that involves the transfer of DNA comprising the QTL, or a resistance-conferring part thereof, from chromosomes 4 of *Solanum habrochaites* LYC 4/78 to the same position on chromosome 4 of another tomato species, most notably *S. lycopersicum*, will result in that QTL, or said resistance-conferring part thereof, not being in its natural genetic background.

The term "disease incidence" is defined herein as the parameter that reflects the capability of the plant to reduce the establishment of an infection and may for instance be established by determining the success of achieving infection of the plant upon contact with the infectious agent.

The term "rate of lesion growth" or "lesion growth rate" is defined herein as the parameter that reflects the capability of the plant to slow or reduce the progression of infection, and may for instance be established by determining the rate of growth of expanding lesions.

The term "quantitatively determining" is defined herein as establishing or assessing in a manner involving measurement, in particular the measurement of aspects measurable in terms of amounts and number. Determinations in degrees of severity and indications of greater, more, less, or equal or of increasing or decreasing magnitude, are not comprised in the present term "quantitatively determining", which term ultimately implies the presence of objective counting mechanism for determining absolute values. Therefore "quantitatively determining disease incidence and/or rate of lesion growth" preferably comprises determining the percentage of all potentially infectious contacts between plant and infectious agent that result in measurable lesions (in order to assess the disease incidence), and/or determining the increase in diameter, circumference, surface area or volume of one or more of said lesions over time under favourable conditions for fungal growth (in order to assess the rate of lesion growth).

The term "standard practice conditions", "standard greenhouse conditions" and "standard conditions" refer to the conditions of light, humidity, temperature, etc. where under plants are grown or incubated, for instance for the purpose of phenotypic characterization of disease resistance, as being standard. For greenhouses for instance, this refers to 16-h day, 15° C.-25° C. More in general, the terms refer to standard and reference growth conditions with a photoperiod of 8 to 24 h (photosynthetic photon flux (PPF) 50 to 1000 μmol m$^{-2}$ s$^{-1}$), preferably a light regime of 16 hours light and 8 hours dark, an air temperature of about 19° C. during the day and 15° C. at night, a water vapour pressure deficit of about 4.4 g m$^{-3}$ corresponding to a relative humidity (RH) of about 60%-85%, at 600-700 ppm $CO_2$ and atmospheric $O_2$ concentration and at atmospheric air pressure (generally 1008 hPa). Water and nutrients may be given drop wise near the stem, or in the form of spray or mist. Standard bioassay experimentation conditions, such as stem lesion length assay, disease incidence and lesion growth rate measurements, are further specified in the Examples below. In more detail, the average stem lesion length assay is to be performed as described in Examples 3.10 and 3.11.

Identification of QTLs Associated with Resistance to *Botrytis* in Tomato

It is known that wild tomato species provide suitable sources for disease and pest resistance traits and the presence of partial resistance to *B. cinerea* in leaves of wild tomato species has been documented (Urbasch, 1986). Two factors have hampered breeding for *B. cinerea* resistance in tomato in the past. Firstly, crossing partial resistance into commercial breeding lines has met with limited success. Secondly, reliable and reproducible disease assays were lacking that would enable the identification and localization of genetic material responsible for conferring resistance.

Urbasch (Urbasch, 1986), for instance, infected leaves with mycelium using agar plugs providing the fungus with an excess of nutrients, which strongly affected the infection process. Other researchers have used subjective plant disease indices, which are unsuitable for quantitative analysis required for the identification of quantitative trait loci (QTLs).

*Botrytis cinerea* infection in *Solanum lycopersicum* under laboratory conditions is relatively well studied (e.g. Benito et al., 1998). Droplet inoculation of leaves and subsequent incubation at moderate temperatures (15-20° C.) results in a rapid (16-24 h post-infection (hpi)) development of necrotic spots at the site of the inoculum. Infection is temporarily restricted at this point for approximately 48 h. From that moment onwards a proportion of the lesions (usually 5-10%) starts to expand. Outgrowth of these so called "expanding lesions" is accompanied by an increase in fungal biomass and results in colonisation of the complete leaflet in the following 48 h.

The present inventors found earlier that specific QTLs associated with *Botrytis*-resistance in tomato can be identified when a bioassay for measuring resistance is used wherein the rate of the progression of infection and or the success of achieving infection upon contact with the infectious agent are measured quantitatively on parts of the tomato plant, preferably on detached parts, more preferably on stem segments.

In addition a test can be used as described in Example 4, wherein resistance of whole plants is studied and wherein the stem was mechanically wounded, and *Botrytis* inoculum was applied to the wound.

On using introgression lines, each containing a specific introgression segment of the genome of *S. habrochaites* LYC 4/78 in an *S. lycopersicum* cv. Moneymaker background, the inventors surprisingly were able to discover still further QTLs associated with resistance to *Botrytis* in *S. habrochaites* LYC 4/78. Thus, the present invention now provides a method for producing a cultivated tomato plant that is resistant to *Botrytis*, comprising:

- producing an series of introgression lines of cultivated tomato, wherein each introgression line contains a specific genomic introgression (a chromosomal region) from a *Botrytis*-resistant wild tomato accession, preferably *S. habrochaites* LYC 4/78, and which series together cover the genome of said resistant wild tomato accession;
- identifying QTLs associated with *Botrytis*-resistance in plants of each of said individual introgression lines by performing a quantitative bioassay for measuring resistance to *Botrytis* in plants of each of said individual introgression lines, preferably by measuring disease incidence and/or the rate of lesion growth, and establishing a genetic linkage map that links the observed resistance to *Botrytis* with the presence of chromosomal markers in said introgression lines and assigning contiguous markers on said map that are linked to a enhanced resistance (e.g. a reduced disease incidence and/or a reduced rate of lesion growth) to a quantitative trait locus;
- and using an introgression line that contains a QTL associated with *Botrytis* resistance for the production of a cultivated tomato plant that is resistant to *Botrytis*, or using the marker information for the QTLs thus identified in marker-assisted selection of suspected *Botrytis*-resistant tomato plants.

It was surprisingly found that multiple QTLs for *Botrytis*-resistance were present in the genomes of *Botrytis*-resistant tomato plants, whereas the prior art methods resulted in the tentative identification of QTLs on chromosomes 1, 2, 4 and 10. Moreover, the QTLs that were found by using the present methods were located on chromosomes not previously associated with *Botrytis*-resistance of tomato plants, even when using a similar genetic background (WO 02/085105) Therefore, the methods of the present invention have provided the additional insight that the use on ILs can result in more detailed investigation of the genetic origin of *Botrytis* resistance in tomato and can result in the identification of chromosomal material involved in such resistance not previously identified therewith.

A method for detecting a quantitative trait locus (QTL) associated with resistance to *Botrytis* in tomato according to the present invention, otherwise addressable as method for identifying or locating a quantitative trait locus (QTL), requires the availability of a (partially) *Botrytis*-resistant tomato plant. Such a plant may be provided by any means known in the art, and by using any method for the determination of the presence of said (partial) resistance in said plant. The provision of a (partially) *Botrytis*-resistant tomato plant (which will further serve as a donor plant in a method of the present invention) enables the establishment or provision of chromosomal markers, preferably AFLP, CAPS and/or SCAR markers, most preferably CAPS and/or SCAR markers, for at least one, but preferably for all chromosome of said plant. By establishing a collection of chromosomal markers over the whole length of said chromosomes, the various locations of said chromosomes may effectively be marked. Such methods are well known in the art and exemplary methods will be described in more detail herein below.

A method for detecting a quantitative trait locus (QTL) associated with resistance to *Botrytis* in tomato in accordance with the present invention may comprise the step of measuring the resistance to *Botrytis* in a plant. Hereto, a plant is contacted with an infective amount of *Botrytis*. Such an amount may vary between plants and between fungal species tested. Usually an amount of about 1 to 10 to an amount of about 500-5000 conidia of said fungus will be sufficient.

Measuring the resistance to *Botrytis* may comprises quantitatively determining the disease incidence and/or the rate of lesion growth in a plant.

The step of contacting a plant with an infective amount of *Botrytis* and quantitatively determining the resistance is preferably performed as part of a resistance bioassay on stem segments or leaves as described herein, preferably a resistance bioassay on stem segments more preferably on whole plants as described in Example 4. The skilled person will understand that variations to these assays as described herein below are possible.

A resistance bioassay on stem segments may essentially be performed as follows: First, seeds for the offspring plants are planted and grown to seedlings/plants of suitably approximately 50 cm in height. The top 5-10 cm and bottom 5-10 cm of the stem of the plants may be removed and the remaining 30 cm may be cut into equal segments of 5-6 cm. The stem segments are preferably placed upright in a lattice with the stem base on wet filter paper. Prior to inoculation, the stem segments are suitably sprayed with water in order to ensure an equal spread of the inoculum over the wound surface. Each stem segment may then be inoculated by a conidial suspension of *B. cinerea*. A suitable amount of inoculum, for instance one drop of about 5 µl, comprising approximately $10^6$ conidia·$ml^{-1}$, may thereto be applied on the top of each stem segment. The stem segments are then incubated at a temperature of suitably about 16° C., preferably in the dark, and preferably at high humidity (e.g. 100% RH). Infection progress may be determined quantitatively by measuring the maximum advance of rot symptom at various time intervals after inoculation with a Vernier caliper. At a number of suitable time intervals, for instance at 96, 120 and 144 hours post-infection (hpi), the stems may then be inspected for lesion formation (disease incidence) and lesion growth, in a quantitative manner. Very suitable parameters comprise the measurement of the size of the lesion, for instance by using a caliper. In order to correct for variation caused by the season or cultivation of the plants, the quantitative measurements of the bioassays may be related to the comparable measurements in susceptible control or reference lines. The disease incidence may suitably be determined by dividing the total number of expanding lesions by the total number of inoculation droplets. The proportion of expanding lesions on a particular genotype may then be divided by the proportion of expanding lesions observed in a control or reference genotype and expressed as a percentage. Alternatively, or additionally, lesion growth rates may be determined by calculating the increase in lesion size (e.g. in mm) over a suitable period, for instance over a 24 h period. Data for the non-expanding lesions may be deleted from the quantitative analysis. The lesion growth rate obtained may then optionally be divided by the lesion growth rate observed in a control or reference genotype and expressed as a percentage or as an absolute figure, for instance in millimeters.

Alternatively, plants can be screened by using a leaf infection bioassay as follows: First, tomato seeds are planted and grown to seedlings/plants. For each individual plant one or two compound leaves may be cut from the main stem and transferred to pre-wetted florist foam. The florist foam is then placed in a Petri dish containing tap water and subsequently placed in a spray-wetted container containing wet filter paper. A suitable inoculum comprising *B. cinerea* conidia may be prepared by methods known in the art, for instance as described by Benito et al., 1998. The compound leaves are then inoculated with the conidial suspension of *B. cinerea* by placing a number of droplets, suitably for instance 6 to 10 droplets of 2 μl each, onto the upper surface of the leaves. The container is then closed and the leaves are incubated at a temperature of suitably between 15° C.-20° C., preferably in the dark, and preferably at high humidity. At a number of suitable time intervals, for instance at 96, 120 and 144 hpi, the leaves may then be inspected for disease incidence and lesion growth, in a quantitative manner as described above for the stem bioassay.

A method for detecting a quantitative trait locus (QTL) associated with resistance to *Botrytis* in tomato according to the present invention comprises the steps of establishing a genetic linkage map that links the observed resistance with the presence of chromosomal markers of the donor tomato plant in the recipient plants of the ILs and assigning contiguous markers on said map that are linked to an enhanced resistance to a quantitative trait locus.

A genetic linkage map that links the observed enhanced resistance with the presence of chromosomal markers of the donor tomato plant in said IL plants may be established by any method known in the art. The skilled person is aware of methods for identifying molecular markers linked to resistance quantitative trait loci (QTLs) and the mapping of these markers on a genetic linkage map (see e.g. Bai et al., 2003; Foolad et al., 2002; van Heusden et al., 1999). The association between the *Botrytis*-resistant phenotype and marker genotype may suitably be performed by using such software packages as JoinMap® and MapQTL® (see Examples) or any standard statistical package which can perform analysis of variance analysis. The molecular markers can be used to construct genetic linkage maps and to identify quantitative trait loci (QTLs) for *Botrytis* resistance. Suitable types of molecular markers and methods for obtaining those are described in more detail herein below.

Molecular Markers and QTLs

Molecular markers are used for the visualisation of differences in nucleic acid sequences. This visualisation is possible due to DNA-DNA hybridisation techniques (RFLP) and/or due to techniques using the polymerase chain reaction (e.g. STS, microsatellites, AFLP). All differences between two parental genotypes will segregate in a mapping population (e.g., $BC_1$, $F_2$; see FIG. 2) based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a low distance between markers on a chromosome. Comparing all recombination frequencies will result in the most logical order of the molecular markers on the chromosomes. This most logical order can be depicted in a linkage map (Paterson, 1996). A group of adjacent or contiguous markers on the linkage map that is associated to a reduced disease incidence and/or a reduced lesion growth rate pinpoints the position of a QTL.

Upon the identification of the QTL, the QTL effect (the resistance) may for instance be confirmed by assessing *Botrytis*-resistance in $BC_2S_1$ progenies segregating for the QTLs under investigation. The assessment of the *Botrytis* resistance may suitably be performed by using a stem or leaf bioassay as described herein.

The QTLs for resistance against *Botrytis* in tomato obtainable by using a method of the invention are an aspect of the present invention. A characteristic of such QTLs is that, when present in plants, they are indicative of the presence of a reduced disease incidence and/or a reduced lesion growth rate upon contacting said plant with infective amount of *Botrytis* material, which material may be provided in any form, such as in the form of conidia or mycelium.

The present invention also relates to a QTL for resistance against *Botrytis* in tomato, wherein said QTL is selected from the group consisting of the QTLs on chromosomes 4, 6, 9, 11 and 12 of *Solanum habrochaites* LYC 4/78 associated with *Botrytis* resistance. These QTLs may be more clearly defined or indicated by the markers listed in Tables 1-5. In these tables, the genomic region where the QTLs are located is indicated by the AFLP-markers listed. The QTLs of the present invention comprise genetic information in the form of DNA responsible for conferring (partial) *Botrytis* disease incidence and/or a reduced rate of *Botrytis* lesion growth in a tomato plant. The genetic information may for instance comprise a gene or a regulatory element.

TABLE 1

QTLs found on chromosome 4 in offspring of a cross of *S. lycopersicum* cv. Moneymaker × *S. habrochaites* LYC 4/78 and related quantitative resistance information. Susceptible *S. Lycopersicum* cv. Moneymaker plants showed on average a lesion growth rate of 4.6 mm/day and an average disease incidence of 73 ± 6.4% (See tables 8 and 9).

| QTL | Marker[1]* | Chromosome | Lesion growth rate[2] (mm/day) | Disease incidence[2] (%) |
|---|---|---|---|---|
| QTL-4hA | P18M51-156h<br>P14M48-158h<br>TG609[3]<br>P22M50-158h<br>P14M61-215K<br>P14M48-349h<br>P14M61-237e<br>P14M48-345e<br>P14M50-124e<br>P14M61120e<br>TG62[4]<br>T1405[5]<br>TG555[6]<br>CT50[7]<br>C2At1g74970[8] | 4 | 2.5 | 41 ± 6.4 |
| QTL-4hB | CT50<br>C2At1g74970 | 4 | 2.8 | 51 ± 9.6 |

TABLE 1-continued

QTLs found on chromosome 4 in offspring of a cross of S. *lycopersicum* cv. Moneymaker × S. *habrochaites* LYC 4/78 and related quantitative resistance information. Susceptible S. *Lycopersicum* cv. Moneymaker plants showed on average a lesion growth rate of 4.6 mm/day and an average disease incidence of 73 ± 6.4% (See tables 8 and 9).

| QTL | Marker[1]* | Chromosome | Lesion growth rate[2] (mm/day) | Disease incidence[2] (%) |
|---|---|---|---|---|
| | P14M49-283e | | | |
| | P14M48-74e | | | |
| | P14M50-67e | | | |
| | CT173[9] | | | |
| | P14M50-85h | | | |

[1]*marker nomenclature: Codes by which the AFLP primer combination is commonly indicated, e.g. P18M51-156h, wherein P and M are the common PstI and MseI primer sequences or universal primers (Vos et al., 1995; Bai et al., 2003) followed by 2 or 3 extra selective bases as indicated by a two digit extension code. Two digit extension codes are as follows: 14: AT; 15: CA; 18: CT; 22: GT; 48: CAC; 49: CAG; 50: CAT; 51: CCA; 60: CTC; 61: CTG. 156h is the approximated size in basepairs of the resulting polymorphic fragment (given size ± 2 basepairs). The size is normally rounded off but may also be given in decimals. This fragment is amplified in either S. *lycopersicum* cv Moneymaker (e) or S. *habrochaites* LYC 4/78 (h). Presence of a marker indicates that at least one allele of the indicated origin is present. Primer and adapter sequences are described in detail by Bai et al. 2003.
[2]Disease incidence and lesion growth are determined using methods as explained in detail in the Examples.
[3]TG609: see Table 10.
[4]TG62: See Table 11.
[5]T1405: see Table 20.
[6]TG555: see Table 12.
[7]CT50: see Table 13.
[8]C2_At1g74970: see Table 14.
[9]CT173: see Table 21.

TABLE 2

QTLs found on chromosome 6 in offspring of a cross of S. *lycopersicum* cv. Moneymaker × S. *habrochaites* LYC 4/78 and related quantitative resistance information. Susceptible S. *Lycopersicum* cv. Moneymaker plants showed on average a lesion growth rate of 4.6 mm/day and an average disease incidence of 73 ± 6.4%. See Table 1 for remarks.

| QTL | Marker[1]* | Chromosome | Lesion growth rate[2] (mm/day) | Disease incidence[2] (%) |
|---|---|---|---|---|
| QTL-6h | P22M50-188h | 6 | 3.6 | 49 ± 6.5 |
| | P14M48-521e | | | |
| | P15M48-386h | | | |
| | P18M51-199h | | | |
| | P18M51-103h | | | |
| | P22M50-103e | | | |
| | P18M51-388e | | | |
| | P15M48-395e | | | |
| | P22M50-124e | | | |
| | P14M48-160e | | | |
| | P22M50-513h | | | |

TABLE 3

QTLs found on chromosome 9 in offspring of a cross of S. *lycopersicum* cv. Moneymaker × S. *habrochaites* LYC 4/78 and related quantitative resistance information. Susceptible S. *Lycopersicum* cv. Moneymaker plants showed on average a lesion growth rate of 4.6 mm/day and an average disease incidence of 73 ± 6.4%. See Table 1 for remarks.

| QTL | Marker[1]* | Chromosome | Lesion growth rate[2] (mm/day) | Disease incidence[2] (%) |
|---|---|---|---|---|
| QTL-9h | P18M50-141 | 9 | 3.0-3.1 | 49 ± 6.4-69 ± 6.5 |
| | P14M49-240 | | | |
| | TG254[1] | | | |
| | TG223[2] | | | |
| | TG10[3] | | | |
| | P18M50-134h | | | |

TABLE 3-continued

QTLs found on chromosome 9 in offspring of a cross of S. *lycopersicum* cv. Moneymaker × S. *habrochaites* LYC 4/78 and related quantitative resistance information. Susceptible S. *Lycopersicum* cv. Moneymaker plants showed on average a lesion growth rate of 4.6 mm/day and an average disease incidence of 73 ± 6.4%. See Table 1 for remarks.

| QTL | Marker[1]* | Chromosome | Lesion growth rate[2] (mm/day) | Disease incidence[2] (%) |
|---|---|---|---|---|
| | P14M49-243h | | | |
| | P18M50-599 | | | |
| | P14M60-222h | | | |
| | P22M51-417h | | | |
| | P14M50-174h | | | |
| | P14M60-157h | | | |
| | P14M60-107h | | | |
| | P15M48-138h | | | |
| | P14M48-113h | | | |
| | Tm2a[4] | | | |
| | P18M51-146h | | | |
| | P14M48-282h | | | |
| | P14M50-276h | | | |

[1]TG254: see Table 22.
[2]TG223: see Table 23.
[3]TG10: see Table 17.
[4]Tm2a: see Table 18 or Sorbir, O. T. et al. (2000).

TABLE 4

QTLs found on chromosome 11 in offspring of a cross of S. *lycopersicum* cv. Moneymaker × S. *habrochaites* LYC 4/78 and related quantitative resistance information. Susceptible S. *Lycopersicum* cv. Moneymaker plants showed on average a lesion growth rate of 4.6 mm/day and an average disease incidence of 73 ± 6.4%. See Table 1 for remarks.

| QTL | Marker[1]* | Chromosome | Lesion growth rate[2] (mm/day) | Disease incidence[2] (%) |
|---|---|---|---|---|
| QTL-11h | P14M60-215e | 11 | 3.2 | 34 ± 6.4 |
| | P14M61-173h | | | |
| | P14M50-307h | | | |
| | TG47 | | | |
| | P14M50-29xCD | | | |
| | P18M51-358h | | | |
| | P18M50-27xCD | | | |
| | P18M51-136h | | | |
| | P22M50-488h | | | |
| | TG393 | | | |
| | P14M61-396h | | | |
| | P22M51-235h | | | |
| | P22M51-174e | | | |

[1]TG47: see Table 24.
[2]TG393: see Table 25.

TABLE 5

QTLs found on chromosome 12 in offspring of a cross of S. *lycopersicum* cv. Moneymaker × S. *habrochaites* LYC 4/78 and related quantitative resistance information. Susceptible S. *Lycopersicum* cv. Moneymaker plants showed on average a lesion growth rate of 4.6 mm/day and an average disease incidence of 73 ± 6.4%. See Table 1 for remarks.

| QTL | Marker[1]* | Chromosome | Lesion growth rate[2] (mm/day) | Disease incidence[2] (%) |
|---|---|---|---|---|
| QTL-12h | CT19 | 12 | 2.3 | 24 ± 8.6 |
| | TG68 | | | |
| | P14M48-411e | | | |
| | P18M50-244h | | | |
| | P18M50-273h | | | |
| | P14M61-420h | | | |
| | P14M61-406h | | | |

TABLE 5-continued

QTLs found on chromosome 12 in offspring of a cross of *S. lycopersicum* cv. Moneymaker × *S. habrochaites* LYC 4/78 and related quantitative resistance information. Susceptible *S. Lycopersicum* cv. Moneymaker plants showed on average a lesion growth rate of 4.6 mm/day and an average disease incidence of 73 ± 6.4%. See Table 1 for remarks.

| QTL | Marker[1]* | Chromosome | Lesion growth rate[2] (mm/day) | Disease incidence[2] (%) |
|---|---|---|---|---|
| | P14M61-223h | | | |
| | P14M60-193h | | | |
| | P22M51-314h | | | |
| | TG565 | | | |
| | P14M48-172h | | | |
| | P22M50-321e | | | |
| | P14M60-219e | | | |
| | P14M48-153h | | | |
| | P22M50-97h | | | |
| | TG296 | | | |
| | P22M50-131h | | | |
| | P22M51-135h | | | |

[1]CT19: see Table 26.
[2]TG68: see Table 27. TG565: see Table 28. TG296: see Table 29.

Most reliably, the genomic region where QTL-4hA is located is positioned between markers P18M51-156h and C2_At1g74970 (Table 14) as shown in FIG. 1. Therefore, any marker located within that region may be used to assess the presence of the QTL in the genome of a plant, as well as any marker known to be located in that region based on publicly available information, such as from consensus maps Tomato-EXPEN 1992 (Tanksley et al., 1992), Tomato-EXHIR 1997 (Bernacchi and Tanksley, 1997), Tomato-EXPEN 2000 (Fulton et al., 2002) or Tomato-EXPIMP 2001 (Grandillo and Tanksley, 1996; Tanksley et al. 1996, Doganlar et al. 2002).

Most reliably, the genomic region where QTL-4hB is located, is positioned between markers CT50 (Table 13) and P14M50-85h as shown in FIG. 1. Therefore, any marker located within that region may be used to assess the presence of the QTL in the genome of a plant, as well as any marker known to be located in that region based on publicly available information.

Figure 2:
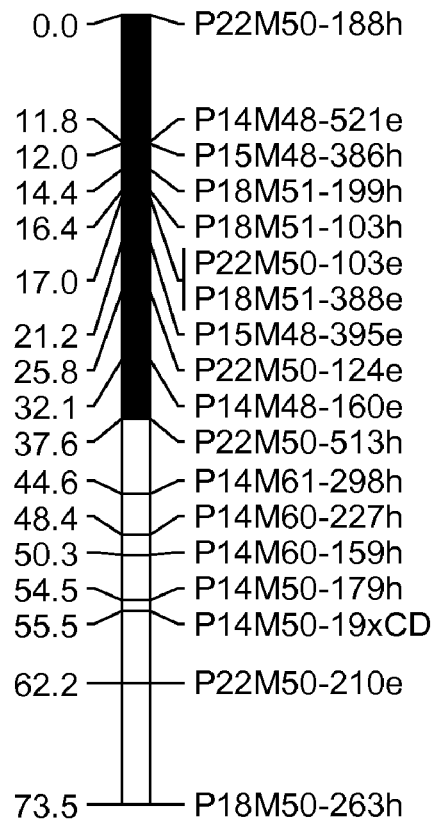
FIG. 2 shows the position of the quantitative trait locus (QTL) for resistance to B. cinerea originating from S. habrochaites LYC 4/78 with the linkage maps representing chromosome 6 (putative position of QTL provided as dark section). The QTL on chromosome 6 decreases both lesion growth rate and disease incidence.

Most reliably, the genomic region where QTL-6h is located, is positioned between markers P22M50-188h and P22M50-513h as shown in FIG. 2. Therefore, any marker located within that region may be used to assess the presence of the QTL in the genome of a plant, as well as any marker known to be located in that region based on publicly available information.

Figure 3:
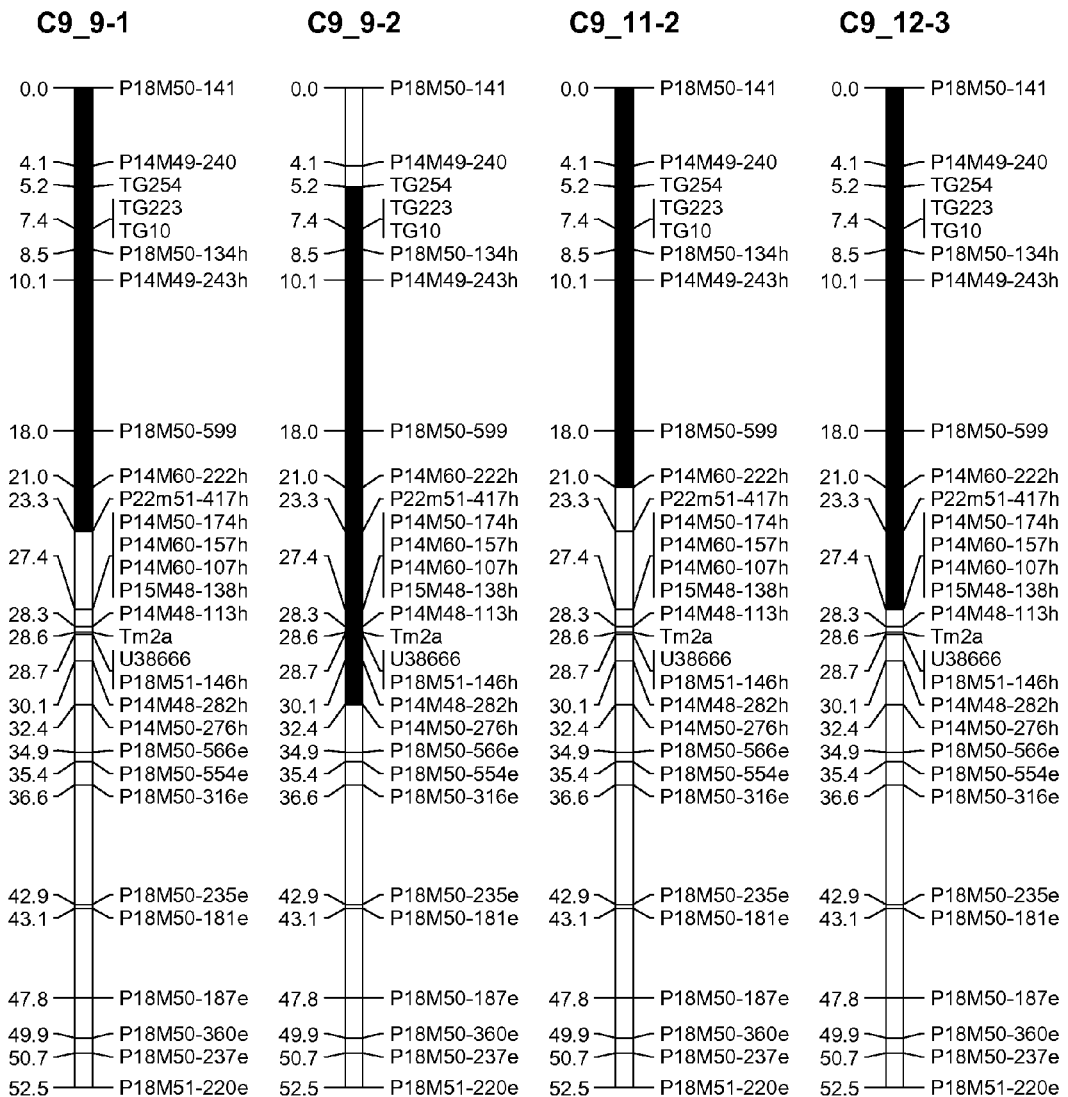
FIG. 3 shows the position of the quantitative trait locus (QTL) for resistance to B. cinerea originating from S. habrochaites LYC 4/78 with the linkage maps representing chromosome 9 (putative position of QTL provided as dark section). The QTL on chromosome 9 decreases both lesion growth rate and disease incidence. The Figure further shows the introgression on chromosome 9 of IL lines 11-2 and 12-3.

Most reliably, the genomic region where QTL-9h is located, is positioned between markers P18M50-141 and P14M50-276h as shown in FIG. 3. Therefore, any marker located within that region may be used to assess the presence of the QTL in the genome of a plant, as well as any marker known to be located in that region based on publicly available information.

Figure 4:
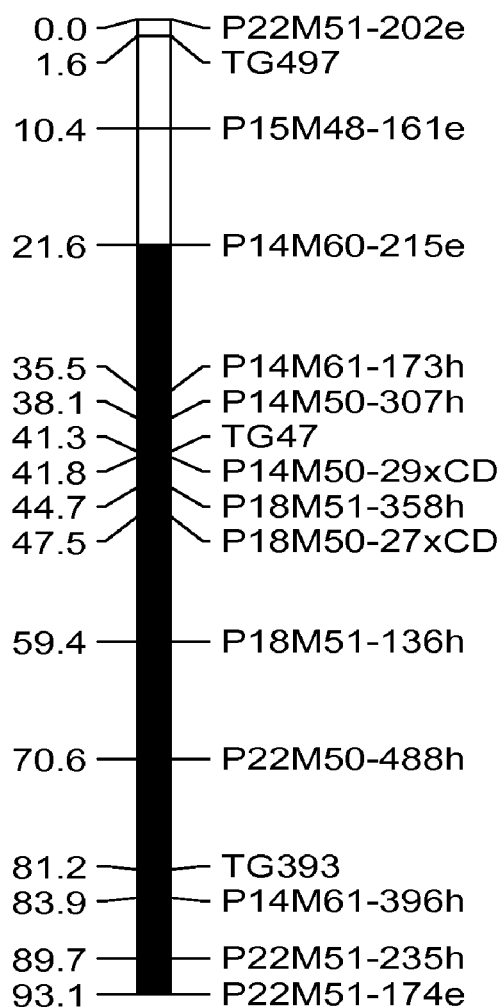
FIG. 4 shows the position of the quantitative trait locus (QTL) for resistance to B. cinerea originating from S. habrochaites LYC 4/78 with the linkage maps representing chromosome 11 (putative position of QTL provided as dark section). The QTL on chromosome 11 decreases both lesion growth rate and disease incidence. The linkage map represents IL line 11-2 of Example 4.

Most reliably, the genomic region where QTL-11h is located, is positioned between markers P14M60-215e and P22M51-174e as shown in FIG. 4. Therefore, any marker located within that region may be used to assess the presence of the QTL in the genome of a plant, as well as any marker known to be located in that region based on publicly available information.

Most reliably, the genomic region where QTL-12h is located, is positioned between markers P14M61-420h and P22M50-131h as shown in FIG. 5. Therefore, any marker located within that region may be used to assess the presence of the QTL in the genome of a plant, as well as any marker known to be located in that region based on publicly available information.

Preferably, a QTL of the present invention comprises at least one marker of Tables 1-5 associated with said QTL. Because the nucleic acid sequence of the QTL that is responsible for conferring the *Botrytis* resistance may only be a fraction of the entire QTL herein identified, the markers merely indicate linked inheritance of genetic regions or the absence of observed recombination within such genetic regions. Therefore, it is noted that the markers listed in Tables 1-5 indicate the chromosomal region where a QTL of the invention is located in the genome of the specified *Solanum* lines and that those markers do not necessarily define the boundaries or the structure of that QTL. Thus, the part of the QTL that comprises the essential resistance-conferring nucleic acid sequence(s) may be considerably smaller than that indicated by the contiguous markers listed for a particular QTL. Such a part is herein referred to as a "resistance-conferring part" of a QTL. As a result a resistance-conferring part of a QTL need not necessarily comprise any of said listed markers. Also other markers may be used to indicate the various QTLs, provided that such markers are genetically linked to the QTLs and the skilled person may find or use a QTL that is analogous to those of the present invention, but wherein one or more markers listed in tables 1-5 and indicated as being linked to said QTL are absent.

A *Botrytis*-resistance-conferring part of a QTL for resistance against *Botrytis* in tomato may be identified by using a molecular marker technique, for instance with one or more of the markers for a QTL shown in Tables 1-5 as being linked to said QTL, preferably in combination with a resistance bioassay. Tomato plants that do not comprise a *Botrytis*-resistance-conferring part of a QTL of the present invention are relatively susceptible to infection by *Botrytis*.

The markers provided by the present invention may very suitably be used for detecting the presence of one or more QTLs of the invention in a suspected *Botrytis*-resistant tomato plant, and may therefore be used in methods involving marker-assisted breeding and selection of *Botrytis* resistant tomato plants. Preferably, detecting the presence of a QTL of the invention is performed with at least one of the markers for a QTL shown in Tables 1-5 as being linked to said QTL. The present invention therefore relates in another aspect to a method for detecting the presence of a QTL for *Botrytis*-resistance, comprising detecting the presence of a nucleic acid sequence of said QTL in a suspected *Botrytis*-resistant tomato plant, which presence may be detected by the use of the said markers.

The nucleic acid sequence of a QTL of the present invention may be determined by methods known to the skilled person. For instance, a nucleic acid sequence comprising said QTL or a resistance-conferring part thereof may be isolated from a *Botrytis*-resistant donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

The present invention therefore also relates to an isolated nucleic acid (preferably DNA) sequence that comprises a QTL of the present invention, or a *Botrytis*-resistance-conferring part thereof. Thus, the markers that pinpoint the various QTLs described herein may be used for the identification, isolation and purification of one or more genes from tomato that encode for *Botrytis* resistance.

The nucleotide sequence of a QTL of the present invention may for instance also be resolved by determining the nucleotide sequence of one or more markers associated with said QTL and designing internal primers for said marker sequences that may then be used to further determine the sequence the QTL outside of said marker sequences. For instance the nucleotide sequence of the AFLP markers from Tables 1-5 may be obtained by isolating said markers from the electrophoresis gel used in the determination of the presence of said markers in the genome of a subject plant, and determining the nucleotide sequence of said markers by for instance dideoxy chain terminating methods, well known in the art.

In embodiments of such methods for detecting the presence of a QTL in a suspected *Botrytis*-resistant tomato plant, the method may also comprise the steps of providing a oligonucleotide or polynucleotide capable of hybridizing under stringent hybridization conditions to a nucleic acid sequence of a marker linked to said QTL, preferably selected from the markers of Tables 1-5 as being linked to said QTL, contacting said oligonucleotide or polynucleotide with a genomic nucleic acid of a suspected *Botrytis*-resistant tomato plant, and determining the presence of specific hybridization of said oligonucleotide or polynucleotide to said genomic nucleic acid. Preferably said method is performed on a nucleic acid sample obtained from said suspected *Botrytis*-resistant tomato plant, although in situ hybridization methods may also be employed. Alternatively, and in a more preferred embodiment, the skilled person may, once the nucleotide sequence of the QTL has been determined, design specific hybridization probes or oligonucleotides capable of hybridizing under stringent hybridization conditions to the nucleic acid sequence of said QTL and may use such hybridization probes in methods for detecting the presence of a QTL of the invention in a suspected *Botrytis*-resistant tomato plant.

The phrase "stringent hybridization conditions" refers to conditions under which a probe or polynucleotide will hybridize to its target subsequence, typically in a complex mixture of nucleic acids, but to essentially no other sequences. Stringent conditions are sequence-dependent and will be different in different circumstances. Longer sequences hybridize specifically at higher temperatures. An extensive guide to the hybridization of nucleic acids is found in Tijssen (Thijssen, 1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. Additional guidelines for determining hybridization parameters are provided in numerous references, e.g. Current Protocols in Molecular Biology, eds. Ausubel, et al. 1995).

"Nucleic acid" or "oligonucleotide" or "polynucleotide" or grammatical equivalents used herein means at least two nucleotides covalently linked together. Oligonucleotides are typically from about 7, 8, 9, 10, 12, 15, 18 20 25, 30, 40, 50 or up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, 1991), and peptide nucleic acid backbones and linkages. Mixtures of naturally occurring nucleic acids and analogs can be used. Particularly preferred analogs for oligonucleotides are peptide nucleic acids (PNA).

Production of *Botrytis*-Resistant Tomato Plants by Transgenic Methods

According to another aspect of the present invention, a nucleic acid (preferably DNA) sequence comprising at least one QTL of the present invention or a *Botrytis*-resistance-conferring part thereof, may be used for the production of a *Botrytis*-resistant tomato plant. In this aspect, the invention provides for the use of a QTL of to the present invention or *Botrytis*-resistance-conferring parts thereof, for producing a *Botrytis*-resistant tomato plant, which use involves the introduction of a nucleic acid sequence comprising said QTL in a *Botrytis*-susceptible recipient tomato plant. As stated, said nucleic acid sequence may be derived from a suitable *Botrytis*-resistant donor tomato plant. Two suitable *Botrytis*-resistant donor tomato plants capable of providing a nucleic acid sequence comprising at least one of the hereinbefore described QTLs, or *Botrytis*-resistance-conferring parts thereof, are *S. habrochaites* LYC 4/78. Other related tomato plants that exhibit resistance to *Botrytis* and comprise one or more genes that encode for *Botrytis* resistance may also be utilized as *Botrytis*-resistance donor plants as the present invention describes how this material may be identified. Other accessions of tomato species can be examined for *Botrytis*-resistance including, but not limited to, *Lycopersicon cerasiforme, Lycopersicon cheesmanii, Lycopersicon chilense, Lycopersicon chmielewskii, Solanum lycopersicum, Lycopersicon hirsutum, Lycopersicon parviflorum, Lycopersicon pennellii, Lycopersicon peruvianum, Lycopersicon pimpinellifolium* and *Solanum lycopersicoides*.

Once identified in a suitable donor tomato plant, the nucleic acid sequence that comprises a QTL for *Botrytis*-resistance according to the present invention, or a *Botrytis*-resistance-conferring part thereof, may be transferred to a suitable recipient plant by any method available. For instance, the said nucleic acid sequence may be transferred by crossing a *Botrytis*-resistance donor tomato plant with a susceptible recipient tomato plant (i.e. by introgression), by transformation, by protoplast fusion, by a doubled haploid technique or by embryo rescue or by any other nucleic acid transfer system, optionally followed by selection of offspring plants comprising the QTL and exhibiting *Botrytis*-resistance. For transgenic methods of transfer a nucleic acid sequence comprising a QTL for *Botrytis*-resistance according to the present invention, or a *Botrytis*-resistance-conferring part thereof, may be isolated from said donor plant by using methods known in the art and the thus isolated nucleic acid sequence may be transferred to the recipient plant by transgenic methods, for instance by means of a vector, in a gamete, or in any other suitable transfer element, such as a ballistic particle coated with said nucleic acid sequence.

Plant transformation generally involves the construction of an expression vector that will function in plant cells. In the present invention, such a vector comprises a nucleic acid sequence that comprises a QTL for *Botrytis*-resistance of the present invention, or a *Botrytis*-resistance-conferring part thereof, which vector may comprise a *Botrytis*-resistance-conferring gene that is under control of or operatively linked to a regulatory element, such as a promoter. The expression vector may contain one or more such operably linked gene/regulatory element combinations, provided that at least one of the genes contained in the combinations encodes for *Botrytis*-resistance. The vector(s) may be in the form of a plasmid, and can be used, alone or in combination with other plasmids, to provide transgenic plants that are resistant to *Botrytis*, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (see e.g. Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (see e.g. Kado, 1991). Methods of introducing expression vectors into plant tissue include the direct infection or co-cultivation of plant cells with *Agrobacterium tumefaciens* (Horsch et al., 1985). Descriptions of *Agrobacterium* vectors systems and methods for *Agrobacterium*-mediated gene transfer provided by Gruber and Crosby, 1993 and Moloney et al., 1989. See also, U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993. General methods of culturing plant tissues are provided for example by Miki et al., 1993 and by Phillips, et al., 1988. A proper reference handbook for molecular cloning techniques and suitable expression vectors is Sambrook and Russell (2001).

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes (See, Sanford et al., 1987, 1993; Sanford, 1988, 1990; Klein et al., 1988, 1992). Another method for introducing DNA to plants is via the sonication of target cells (see Zhang et al., 1991). Alternatively, liposome or spheroplast fusion has been used to introduce expression vectors into plants (see e.g. Deshayes et al., 1985 and Christou et al., 1987). Direct uptake of DNA into protoplasts using $CaCl_2$ precipitation, polyvinyl alcohol or poly-L-ornithine has also been reported (see e.g., Hain et al. 1985 and Draper et al., 1982). Electroporation of protoplasts and whole cells and tissues has also been described (D'Halluin et al., 1992 and Laursen et al., 1994).

Following transformation of tomato target tissues, expression of the above described selectable marker genes allows for preferential selection of transformed cells, tissues and/or plants, using regeneration and selection methods now well known in the art. The markers of Tables 1-5 may also be used for that purpose.

Production of *Botrytis*-Resistant Tomato Plants by Non-Transgenic Methods

In an alternative embodiment for producing a *Botrytis*-resistant tomato plant, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbreeded in nature, is tissue cultured into a hybrid plant exhibiting the desirable combination of traits. More specifically, a first protoplast can be obtained from a tomato plant or other plant line that exhibits resistance to infection by *Botrytis*. For example, a protoplast from *S. habrochaites* LYC 4/78 can be used. A second protoplast can be obtained from a second tomato or other plant variety, preferably a tomato line that comprises commercially desirable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a nucleic acid comprising one or more QTLs of the present invention from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (Pierik, 1999).

The present invention also relates to a method of producing a *Botrytis*-resistant tomato plant comprising the steps of performing a method for detecting the presence of a quantitative trait locus (QTL) associated with resistance to *B. cinerea* in a donor tomato plant according to invention as described above, and transferring a nucleic acid sequence comprising at least one QTL thus detected, or a *Botrytis*-resistance-conferring part thereof, from said donor plant to a *Botrytis*-susceptible recipient tomato plant. The transfer of said nucleic acid sequence may be performed by any of the methods previously described herein.

A preferred embodiment of such a method comprises the transfer by introgression of said nucleic acid sequence from a *Botrytis*-resistant donor tomato plant into a *Botrytis*-susceptible recipient tomato plant by crossing said plants. This transfer may thus suitably be accomplished by using traditional breeding techniques. QTLs are preferably introgressed into commercial tomato varieties by using marker-assisted breeding (MAS). Marker-assisted breeding or marker-assisted selection involves the use of one or more of the molecular markers for the identification and selection of those offspring plants that contain one or more of the genes that encode for the desired trait. In the present instance, such identification and selection is based on selection of QTLs of the present invention or markers associated therewith. MAS can also be used to develop near-isogenic lines (NIL) harboring the QTL of interest, allowing a more detailed study of each QTL effect and is also an effective method for development of backcross inbred line (BIL) populations (see e.g. Nesbitt et al., 2001; van Berloo et al., 2001). Tomato plants developed according to this preferred embodiment can advantageously derive a majority of their traits from the recipient plant, and derive Botrytis-resistance from the donor plant.

Since resistance to B cinerea is inherited polygenically, it is preferred that at least two, preferably three QTLs or Botrytis-resistance-conferring parts thereof, are inserted by a suitable transfer method into a single recipient plant, i.e. that multiple QTLs are stacked in the recipient plant's genome. It is believed that stacking of two or more QTLs of the invention may lead to increased resistance to Botrytis. As the skilled person will readily understand, stacking may be achieved by any method, for instance by transforming a plant with a nucleic acid construct comprising multiple QTLs of the invention. Alternatively, at least one QTL may be present in each parent plant of a cross, so that at least two QTLs are comprised in the resulting hybrid. By stacking of these resistance traits highly resistant plants may be obtained. Such plants are highly preferred embodiments of the present invention.

As discussed briefly above, traditional breeding techniques can be used to introgress a nucleic acid sequence encoding for Botrytis resistance into a Botrytis-susceptible recipient tomato plant. In one method, which is referred to as pedigree breeding, a donor tomato plant that exhibits resistance to Botrytis and comprising a nucleic acid sequence encoding for Botrytis resistance is crossed with a Botrytis-susceptible recipient tomato plant that preferably exhibits commercially desirable characteristics, such as, but not limited to, disease resistance, insect resistance, valuable fruit characteristics, etc. The resulting plant population (representing the $F_1$ hybrids) is then self-pollinated and set seeds ($F_2$ seeds). The $F_2$ plants grown from the $F_2$ seeds are then screened for resistance to Botrytis. The population can be screened in a number of different ways.

First, the population can be screened using a traditional disease screen. Such disease screens are known in the art. Preferably a quantitative stem or leaf infection bioassay is used, preferably the stem bioassay used in methods of the present invention as outlined in more detail hereinabove and the Examples is used. Second, marker-assisted selection can be performed using one or more of the hereinbefore-described molecular markers to identify those progeny that comprise a nucleic acid sequence encoding for Botrytis-resistance. Other methods, referred to hereinabove by methods for detecting the presence of a QTL may be used. Also, marker-assisted selection can be used to confirm the results obtained from the quantitative bioassays, and therefore, several methods may also be used in combination.

Botrytis-Resistant Tomato Plants and Seeds

A Botrytis-resistant tomato plant of the present invention is characterized by having a high level of resistance. This is defined as being a resistance level that is higher than that observed for susceptible control plants. In fact, the plants of the invention have a level of resistance that is higher than that of any commercial tomato variety, i.e. a variety having commercially desirable characteristics, known to date. A plant of the invention has a susceptibility to Botrytis cinerea which is at least 3 times lower than a susceptible control plant when measured by a bioassay. For instance when measured by a bioassay wherein the average length of a stem lesion resulting from Botrytis cinerea infection in adult plants is measured during a three week period under standard practice conditions as described in more detail in the Examples 3.10 and 3.11. Typically, a plant of the invention has a level of resistance that results in an average stem lesion length of Botrytis cinerea lesions in adult plants of less than 3.2 cm three weeks after inoculation using standard practice conditions in a resistance bioassay designed to determine resistance based on such characteristics. More typically, a plant of the invention shows an average stem lesion length of less than 2.9 cm. Some plants of the invention even show an average stem lesion length of 2.0 cm. Taking into account that said numbers express the length of a lesion including the 2 cm initial inoculation wound, it can be inferred that a high level of resistance, and even full resistance in the case of some QTLs, is observed in plants of the invention. In comparison, susceptible control plants show a mean average stem lesion length under the same conditions of about 3.6 cm to about 6.0 cm, with an average of 4.85 cm (see Table 7). Also as a comparison, S. habrochaites LA 1777, the QTL-10 containing partially Botrytis resistant source of WO02/085105, shows an average stem lesion length under the same conditions of about 4.3 cm. In summary, the plants of the invention show net stem lesions in the above referred resistance bioassay that are generally less than about 30% (0.9/2.85×100%) of the net length of susceptible control plants, and generally less than about 40% (0.9/2.3×100%) of the net length of partially resistant S. habrochaites LA 1777.

Thus, a plant of the present invention has a susceptibility to Botrytis cinerea when measured by a bioassay which is 3 times lower than, or which is less than ⅓ the level of, a susceptible control plant. Reciprocally, a plant of the invention is more than 3 times more resistant than a susceptible control plant, as defined herein and determined with the bioassay as described. With QTL-1h full resistance is observed. A susceptible control plant is defined as a plant showing normal susceptibility, or no resistance, to Botrytis cinerea infection. An example of a susceptible control plant is plant of the hybrid Solanum lycopersicum cv. "Moneyberg" (De Ruiter Seeds R&D BV, Bergschenhoek, The Netherlands).

A Botrytis-resistant tomato plant, or a part thereof, obtainable by a method of the invention is also an aspect of the present invention.

Another aspect of the present invention relates to a Botrytis-resistant tomato plant, or part thereof, comprising within its genome at least one QTL, or a Botrytis-resistance-conferring part thereof, selected from the group consisting of the QTLs on chromosomes 4, 6, 9, 11 and 12 of Solanum habrochaites LYC 4/78 associated with Botrytis resistance, wherein said QTL or said Botrytis-resistance-conferring part thereof is not in its natural genetic background. The Botrytis-resistant tomato plants of the present invention can be of any genetic type such as inbred, hybrid, haploid, dihaploid, parthenocarp or transgenic. Further, the plants of the present invention may be heterozygous or homozygous for the resistance trait, preferably homozygous. Although the QTLs of the present invention, as well as those QTLs obtainable by a method of the invention, as well as Botrytis-resistance-conferring parts thereof may be transferred to any plant in order to provide for a Botrytis-resistant plant, the methods and plants of the invention are preferably related to plants of the Solanaceae family, more preferably tomato.

In addition to the QTLs on chromosomes 4 (QTL-4hB), 6, 9, 11 and 12 of *Solanum habrochaites* LYC 4/78 associated with *Botrytis* resistance as identified herein, a plant of the present invention may optionally further comprise one or more *S. habrochaites*-derived QTLs identified herein as QTL-1h, QTL-2h and QTL-4hA and described in great detail in co-pending applications PCT/NL2005/000762 and EP 1 652 930 A (European patent application 04077931.6), to which explicit reference is made in this context.

It is submitted that a combination of QTLs, either the QTLs as described herein or the QTLs as described in PCT/NL2005/000762, would increase the disease resistance in plants harboring such a combination. However, each of the QTLs also brings along genetic information from the background ancestor *S. habrochaites*, which means that in offspring with too much genetic information of this background, it will not be possible to obtain plants with the desired optimal agronomic characteristics.

Inbred *Botrytis*-resistant tomato plant lines can be developed using the techniques of recurrent selection and backcrossing, selfing and/or dihaploids or any other technique used to make parental lines. In a method of selection and backcrossing, *Botrytis*-resistance can be introgressed into a target recipient plant (which is called the recurrent parent) by crossing the recurrent parent with a first donor plant (which is different from the recurrent parent and referred to herein as the "non-recurrent parent"). The recurrent parent is a plant that is non-resistant or has a low level of resistance to *Botrytis* and possesses commercially desirable characteristics, such as, but not limited to disease resistance, insect resistance, valuable fruit characteristics, etc. The non-recurrent parent exhibits *Botrytis* resistance and comprises a nucleic acid sequence that encodes for *Botrytis* resistance. The non-recurrent parent can be any plant variety or inbred line that is cross-fertile with the recurrent parent. The progeny resulting from a cross between the recurrent parent and non-recurrent parent are backcrossed to the recurrent parent. The resulting plant population is then screened. The population can be screened in a number of different ways. For instance, the population can be screened using a stem quantitative bioassays as described previously herein. $F_1$ hybrid plants that exhibit a *Botrytis*-resistant phenotype comprise the requisite nucleic acid sequence encoding for *Botrytis* resistance, and possess commercially desirable characteristics, are then selected and selfed and selected for a number of generations in order to allow for the tomato plant to become increasingly inbred. This process of continued selfing and selection can be performed for two to five or more generations. The result of such breeding and selection is the production of lines that are genetically homogenous for the genes associated with *Botrytis* resistance as well as other genes associated with traits of commercial interest. In stead of using phenotypic pathology screens of bioassays, MAS can be performed using one or more of the hereinbefore described molecular markers, hybridization probes or polynucleotides to identify those progeny that comprise a nucleic acid sequence encoding for *Botrytis*-resistance. Alternatively, MAS can be used to confirm the results obtained from the quantitative bioassays. Once the appropriate selections are made, the process is repeated. The process of backcrossing to the recurrent parent and selecting for *Botrytis*-resistance is repeated for approximately five or more generations. The progeny resulting from this process are heterozygous for one or more genes that encode for *Botrytis*-resistance. The last backcross generation is then selfed in order to provide for homozygous pure breeding progeny for *Botrytis*-resistance.

The *Botrytis*-resistant inbred tomato lines described herein can be used in additional crossings to create *Botrytis*-resistant hybrid plants. For example, a first *Botrytis*-resistant inbred tomato plant of the invention can be crossed with a second inbred tomato plant possessing commercially desirable traits such as, but not limited to, disease resistance, insect resistance, desirable fruit characteristics, etc. This second inbred tomato line may or may not be *Botrytis*-resistant.

Another aspect of the present invention relates to a method of producing seeds that can be grown into *Botrytis*-resistant tomato plants. In one embodiment, the method comprises the steps of providing a *Botrytis*-resistant tomato plant of the invention, crossing said *Botrytis*-resistant plant with a *Solanum lycopersicum* plant, and collecting seeds resulting from said cross, which when planted, produce *Botrytis*-resistant tomato plants.

In another embodiment, the method comprises the steps of providing a *Botrytis*-resistant tomato plant of the invention, crossing said *Botrytis*-resistant plant with a *Solanum lycopersicum* plant, collecting seeds resulting from said cross, regenerating said seeds into plants, selecting *Botrytis*-resistant plants by any of the methods described herein, self-crossing the selected plants for a sufficient number of generations to obtain plants that are fixed for an allele that confers *Botrytis*-resistance in the plants, backcrossing the plants thus produced with *S. lycopersicum* plants having desirable phenotypic traits for a sufficient number of generations to obtain *S. lycopersicum* plants that are *Botrytis*-resistant and have desirable phenotypic traits, and collecting the seeds produced from the plants resulting from the last backcross, which when planted, produce tomato plants which are *Botrytis*-resistant.

By way of example, and not of limitation, Examples of the present invention will now be given.

EXAMPLE 1

Method of Identifying QTLs Associated with Resistance to *Botrytis cinerea*

1.1. Introduction

This Example presents the development of a quantitative bioassay for evaluating the resistance to *Botrytis cinerea* of a collection of wild tomato genotypes.

Partial resistance against *Botrytis cinerea* has been reported in wild tomato species, but these reports have largely been descriptive and qualitative. The identification of partially resistant genotypes would provide perspectives to introgress resistance into commercial breeding lines to obtain lines with manageable resistance levels. The availability of a reproducible, objective and quantitative assay, as well as the identification of genotypes with a genetically determined (partial) grey mould resistance opens the way for resistance breeding in cultured tomato varieties.

The present Example describes a quantitative disease assay. The assay is applied on leaves (leaf inoculation assay) and stem segments (stem inoculation assay). Two parameters for disease susceptibility were examined. The first parameter measured was the disease incidence (DI), i.e. the proportion of inoculation that resulted in an expanding lesion. If the (partial) failure of a primary *B. cinerea* lesion to expand on a particular host genotype is a genetic trait of the plant, such a trait is important as it directly limits the number of disease foci in the crop. The second parameter tested was the lesion growth rate over a period of 24 h (lesion growth, LG). Lesions that expanded from the primary inoculation spot appeared to spread at an even rate (in mm/day) over time until the lesion reached the edge of the leaf or the bottom end of the stem segment. The present assays enable the quantification of both the occurrence (disease incidence) and development (lesion growth) of *B. cinerea* infection, resulting in two sets of quantitative trait data. The assay was used to screen a collection of tomato species (hereinafter also termed "accessions") for the presence of resistance therein.

1.2. Plants

Plant genotypes tested are listed in Table 6.

TABLE 6

List of Solarium genotypes tested.

| Code | Source [1] | Species | Specification/ Cultivar | Leaf [2] | Stem [2] | Reference [3] |
|---|---|---|---|---|---|---|
| 78/1604 | DRS | *S. lycopersicum* | Kecksemeti Torpe | Y | Y | |
| 82/2577 | DRS | *S. lycopersicum* | Futuria | Y | Y | |
| 83/2896 | DRS | *S. lycopersicum* | Biruinca | Y | | |
| 89/3695 | DRS | *S. lycopersicum* | X *S. lycopersicum* var. cerasiforme | | Y | |
| 89/3793 | DRS | *S. pimpinellifolium* | | | Y | |
| 89/3862 | DRS | *S. lycopersicum* | Olomoucke | Y | | |
| 90/4063 | DRS | *S. lycopersicum* | L 4034 | Y | | |
| 91/4311 | DRS | *S. lycopersicum* | Seedathip 2 | Y | Y | |
| 96/4326 | DRS | *S. lycopersicoides* | Gb nr 90124 | Y | Y | |
| MM | WU PPW | *S. lycopersicum* | Moneymaker | S | S | |
| G1.1290 | WU LoPB | *S. habrochaites* | | | Y | |
| G1.1556 | WU LoPB | *S. chilense* | | Y | Y | |
| G1.1558 | WU LoPb | *S. chilense* | | Y | | |
| G1.1560 | WU LoPB | *S. habrochaites* | | Y | Y | |
| G1.1601 | WU LoPB | *S. neorickii* | | Y | Y | |
| G1.1615 | WU LoPB | *S. cheesmanii* | | | Y | |
| IZ.2 [3] | MPIZK | *S. pimpinellifolium* | | | Y | (Urbasch, 1986) |
| LA.716 | TGRC | *S. pennellii* | | Y | | |
| LA.2157 | TGRC | *L. peruvianum* | | | Y | |
| LA.2172 | TGRC | *L. peruvianum* | | | Y | |
| Lyc. 4/78 [3] | IPK | *S. habrochaites* | | Y | Y | (Urbasch, 1986) |
| T160/79 [3] | IPK | *L. glandulosum* | | | Y | (Urbasch, 1986) |
| T566/81 [3] | IPK | *S. habrochaites* | | | Y | (Urbasch, 1986) |

[1] DRS: De Ruiter Seeds, Bergschenhoek, The Netherlands; WU PPW: Plantkundig Proefcentrum Wageningen, Wageningen University, Wageningen, The Netherlands; LoPB: Laboratory of Plant Breeding, Wageningen University, Wageningen, The Netherlands; MPIZK: Max Planck Institut fur Züchtungsforschung an Kulturpflanze, Köln, Germany; TGRC: Tomato Genetics Resource Center, University of California at Davis, Davis CA, USA; IPK: Institut fur Pflanzengenetik und Kulturpflanzenforschung, Gatersleben, Germany.
[2] Y indicates that the genotype was tested in the particular assay, S indicates the genotype served as a susceptible reference control.
[3] Published before as being resistant against *B. cinerea*.

Plants were grown in potting soil in 12 cm pots in a greenhouse with minimal temperature of 15° C. Artificial sodium lamplight was applied (16 h/day) from October through March. At 5-7 days after germination, 10 ml FeNaEDTA solution (3.5 g/l) was added, followed 3 days later by 10 ml of micronutrient solution (0.286 g/l $H_3BO_3$; 0.1558 g/l $MnSO_4.H_2O$; 0.008 g/l $CuO_4.H_2O$; 0.022 g/l $ZnSO_4$; 0.00196 $(NH_4)_6Mo_7O_{24}.4H_2O$). From two weeks after germination onwards, 5 ml of a Hoagland solution (5 mM $Ca(NO_3)_2$; 5 mM $KNO_3$; 2 mM $MgSO_4$; 1 mM $KH_2PO_4$) was added on a weekly basis.

1.3. Leaf Assay

An inoculum from *B. cinerea* strain B05.10 was prepared according to Benito (1998). For each individual plant one or two compound leaves that were fully stretched were detached from the main stem with a sharp razor blade and transferred to pre-wetted florist foam. The florist foam was placed in a Petri dish containing tap water and subsequently placed in a spray-wetted container containing wet filter paper. The compound leaves were then inoculated with a conidial suspension of *B. cinerea* by carefully pipetting a total of 6 to 10 droplets of inoculum (2 µl) onto the upper surface of the leaves. The containers were closed with a spray-wetted lid and incubated at 15° C. in the dark at 100% RH, essentially as described by Benito et al., 1998. Suitably, one composite leaf was divided into four leaflets, and wherein every leaflet was inoculated with 10 drops of 2 µl each, containing 2000 conidia. Both the proportion of aggressive expanding lesions (disease incidence) and the lesion growth rate were monitored over several days.

To correct for variation caused by the season or cultivation of the plants, the disease incidence of a particular genotype in each experiment was related to the disease incidence of Moneymaker tested in that same experiment.

Lesion sizes were measured at 96, 120 and 144 hpi using a caliper. The disease incidence was determined by dividing the total number of expanding lesions by the total number of inoculation droplets. Lesion growth rates were determined by calculating the increase in lesion size (in mm) over a 24 h period. Data for the non-expanding lesions were deleted from the quantitative analysis.

1.4. Stem Assay (Standardized Procedure)

The stem assay was performed as follows: The top 5-10 cm and bottom 5-10 cm of the stem of approximately 50 cm high plants were removed and the remaining 30 cm was cut into equal segments of 5-6 cm. Each stem segment was placed upright in a lattice with the stem base on wet filter paper. Prior to inoculation, the stem segments were sprayed with tap water in order to ensure an equal spread of the inoculum over the wound surface. Inoculum was prepared as described for the leaf assay. One drop of a 5 µl inoculum, containing approximately $10^6$ conidia·ml$^{-1}$, was applied on the top of each stem segment. Incubations were performed at 15±2° C. in the dark with 100% relative humidity. Infection progress was determined by measuring the maximum advance of rot symptom at various time intervals after inoculation with a Vernier caliper.

For each genotype, the percentage of infected stem pieces was calculated. The disease incidence was determined by dividing the total number of stem segments with expanding lesions by the total number of inoculated segments. Lesion growth rates were determined by calculating the increase in lesion size over a 24 h period, whereby the data for the non-expanding lesions were omitted from the analysis.

1.5. Results

The disease incidence and lesion growth in detached leaf infection experiments were determined over several days for each genotype, usually from 2-4 days post-infection. The disease incidence in *S. lycopersicum* cv. Moneymaker, which served as a reference, fluctuated between 15 and 78% in these experiments. Except for genotypes 82/2577 and 83/2896 (both of the species *S. lycopersicum*), the genotypes tested showed in all experiments a lower disease incidence than Moneymaker. Genotypes G1.1556, G1.1560 and G1.1601 showed a low disease incidence in three independent experiments, ranging from 0 to 21%. Statistical analysis indicated that the disease incidence in genotypes 78/1604, 91/4311, 96/4326, G1.1556, GI 1558, G1.1560, G1.1601, LA716 and LYC 4/78 was significantly lower than in the control line *S. lycopersicum* cv. Moneymaker ($p<0.05$). There was, however, a great variation between weeks and some of the differences observed in detached leaf assays may actually not be very robust because of the fluctuations in disease incidence between experiments/weeks (15-78%).

Within these resistant genotypes (with a disease incidence significantly lower than that in the Moneymaker reference), the lesions that expanded successfully often did so at similar rate as in Moneymaker (e.g. 96/4326, G1.1560, LA716). The converse situation was not found: none of the genotypes displayed a disease incidence similar to that of Moneymaker but a lesion growth rate slower than Moneymaker.

Lesion growth rate over a 24 h period (between 48 and 72 hpi) in most genotypes was in the same range as Moneymaker. Five accessions (91/4311, 160/79, G1.1556, G1.1601 and LYC 4/78) showed a slower lesion growth rate, which was statistically significantly different from that of *S. lycopersicum* cv. Moneymaker.

The stem segment infection assay appeared to be more robust than the leaf assay in terms of reproducibility between experiments performed in different seasons. Even though the number of data points with stem segments (5-8 segments per plant) is a great deal smaller than with the leaf assay (40 inoculation droplets per compound leaf, one or two leaves could be tested per plant), the variability between experiments was generally lower in the stem segment assay. The disease incidence in the stem assay for the control genotype *S. lycopersicum* cv. Moneymaker ranged from 52-95%. The disease incidence in 17 genotypes was compared to the disease incidence of the control line *S. lycopersicum* cv. Moneymaker determined in the same experiment/week. Most genotypes showed a disease incidence in a similar range as the control line Moneymaker. Genotypes G1.1556 (29% and 41%) and G1.1560 (28% and 7%) showed a reduced disease incidence. Only G1.1560 differed statistically significant ($p<0.05$) from the control.

The lesion growth rates in the stem assay for the control genotype *S. lycopersicum* cv. Moneymaker ranged from 5.4 to 9.2 mm/day. The lesion growth rates of many genotypes were in a similar range as the control. However, in accessions 89/3793, G1.1601, LYC 4/78, T566-81, the lesion growth rate was statistically significantly different ($p<0.01$) from the control cv. Moneymaker.

With a number of genotypes that were rated as partially resistant in the stem segment assay, qualitative assays were performed on whole plants, grown in a glasshouse on ROCKWOOL®. The aim was to evaluate whether genotypes that appeared resistant in stem segments under laboratory conditions indeed were more resistant than control lines in a semi-commercial cropping system. Plants were grown in randomised order in rows of Rockwool®, the glasshouse compartment was filled with citrus fruit heavily infected by *B. cinerea* at point of sporulation. The glasshouse compartment was kept at high humidity by spraying the floor twice a day with tap water and leaving doors and windows closed. At regular intervals pruning wounds were made on all plants and the occurrence of grey mould was monitored over time.

A number of wild tomato accessions were identified that displayed a severe reduction of both parameters, thus providing potential sources for introgressing two, potentially independent mechanisms of partial resistance into *S. lycopersicum*.

EXAMPLE 2

Mapping Partial Resistance to *Botrytis cinerea* in an Interspecific Tomato Population

*S. lycopersicum* cv Moneymaker×*S. habrochaites* Accession LYC 4/78

In this Example, two QTL loci conferring partial resistance to *B. cinerea* originating from *S. habrochaites* LYC 4/78 are presented. A confirmation of the results was obtained by assessing the resistance level to *B. cinerea* in two $BC_2S_1$ populations segregating for one of the two QTL loci respectively.

2.1. Plant Material

Seeds of *Solanum habrochaites* LYC 4/78 (hereafter referred as LYC 4/78) were obtained from the gene bank located at the Institute for Plant Genetics and Crop Plant Research, Gatersleben, Germany.

Seeds of *Solanum lycopersicum* cv. Moneymaker (hereafter referred as Moneymaker) were obtained from the seed bank of De Ruiter Seeds R&D BV, Bergschenhoek, The Netherlands.

An interspecific cross between Moneymaker and LYC 4/78 was made to produce $F_1$ seeds. The $F_1$ seeds were grown into $F_1$ plants. $F_2$ seeds, derived from selfing one $F_1$ plant were sown to obtain an $F_2$ population of 174 individuals. A $BC_2$ (backcross 2) population of 59 individuals was generated by two rounds of backcrossing with Moneymaker as the recurrent and female parent. Using MAS, $BC_2$, $BC_3$, and $BC_4$ genotypes were selected containing one of the two identified QTLs and some $BC_2$ were self pollinated to produce $BC_2S_1$ seeds (see FIG. 2). Two $BC_2S_1$ populations were grown: one of 60 $BC_2S_1$ individuals that segregated for the QTL for disease incidence and another one of 47 $BC_2S_1$ individuals that segregated for the QTL for lesion growth.

2.2. Stem Assay

An inoculum from *B. cinerea* strain B05.10 was prepared according to Benito (1998). The stem assay was performed as described in Example 1.

2.3. DNA Isolation and Marker Analysis

Genomic DNA was isolated from two young (rolled up) leaves using a cetyltrimethylammonium bromide (CTAB) based protocol according to Steward and Via (1993), adjusted for high throughput DNA isolation using one ml micronic tubes (Micronic B V, Lelystad, The Netherlands) and grounded using a Retsch 300 mm shaker at maximum speed (Retsch B V, Ochten, The Netherlands). The AFLP analysis (Vos et al., 1995) of $F_2$, $BC_2$, $BC_3$, $BC_4$ and $BC_2S_1$ populations was done and the AFLP fragments were resolved on a LI-COR 4200 DNA sequencer, essentially following the method published by Myburg (Myburg et al. 2001). The selective Pst primer was labeled with an IRD 700 or IRD 800 fluorescent label. AFLP gel images were scored using the AFLP-Quantar Pro software package (Keygene B V, Wageningen, The Netherlands). The following ten primer combinations and adapter sequences were used for genotyping: P14M48, P14M49, P14M50, P14M60, P14M61, P15M48, P18M50, P18M51, P22M50 and P22M51, as described by Bai et al. (2003).

2.4. Phenotypic Analysis of the $F_2$ Population

Variation in disease incidence between the different Botrytis assays was observed (See Example 1, supra). Therefore seven independent consecutive stem disease assays were performed on 172 of the 174 individuals of the $F_2$ population derived from the cross between Moneymaker×LYC 4/78. This resulted in at least five independent evaluations of the disease bioassay for almost each $F_2$ genotype. In each individual disease bioassay six stem segments contributed to the calculation of the lesion growth. The average values for disease incidence and lesion growth for the $F_2$ population showed a normal distribution (data not shown). The average disease incidence for Moneymaker is 59% with a lesion growth of 9.2 mm/day. The average disease incidence in the $F_2$ population ranged between 10% and 97% with a population average of 48%. Lesion growth ranged between 3.3 mm and 11.5 mm/day with an average of 7.8 mm/day.

Average disease incidence of each individual experiment ranged from 31% to 73%, while the average lesion growth ranged from 6.2 to 7.9 mm/day (data not shown). Lesion growth can only be calculated if there is at least infection in one of the six stem pieces. Consequently an increase in the number of informative genotypes for lesion growth could be observed with higher disease incidences. For instance, with the low average disease incidence (31%) only 52% of the genotypes were informative for lesion growth.

2.5. Molecular Markers & Genetic Linkage Map

A genetic linkage map was calculated for an $F_2$ population (n=174) derived from the cross of Moneymaker×LYC 4/78. Ten primer combinations were used to obtain 218 amplified fragment length polymorphism (AFLP) markers in the $F_2$ population (n=174). A total of 69 markers (31.7%) could be readily scored co-dominantly, thus allowing the calculation of an integrated $F_2$ genetic linkage map. Marker analysis performed on $BC_2$, $BC_3$ and $BC_2S_1$ genotypes allowed the addition of an additional 145 AFLP markers. A total of 102 out of these 145 additional AFLP markers were previously not scored due to complexity of the $F_2$ gels. The overall genetic linkage map consisted of 315 AFLP markers of 14 linkage groups and has a total length of 958 cM. Since co-migrating AFLP markers within a species are generally allele specific, co-linearity with other AFLP linkage maps was used to assign linkage groups to chromosomes. Some Moneymaker specific AFLP markers were in common with the genetic linkage maps as published (Haanstra et al. 1999; Bai et al. 2003) and therefore some linkage groups could be assigned to chromosomes, including the linkage groups harboring the identified QTLs. To improve the linkage map in the QTL intervals, diagnostic CAPS markers were added in these regions based on the published S. lycopersicum×L. pennellii map (Tanksley et al. 1992; Haanstra et al. 1999).

2.6. Linkage Analysis and QTL Mapping

Marker data were analyzed and a genetic linkage map was calculated as described in paragraph 3.5.

The total length of the $F_2$ linkage map was 958 cM, which is less then other published interspecific Lycopersicon maps with genetic lengths ranging from 1200-1400 cM (Foolad et al. 2002; Haanstra et al. 1999; Tanksley et al. 1992). Additional AFLP markers were scored using AFLP marker data obtained from backcross and $BC_2S_1$ populations. Although 46% more markers were placed on the linkage map, the length of the genetic linkage map did not increase. The reason for this is that the used data were obtained from several small sub-families and thus not informative for the calculation of genetic distances, but estimation of the position is possible by visual inspection of the graphical genotypes (Van Berloo, 1999).

2.7. QTL Mapping in the $F_2$ Population

The phenotypical and marker data were used for the identification of QTLs by means of interval mapping (IM, see paragraph 3.5). IM was both applied to data obtained from individual replicates and to the average values of the replicates.

Disease Incidence

Interval mapping for disease incidence in the $F_2$ population was done for those individual disease tests with an average disease incidence lower than 50% and for average data obtained from all disease tests. The average data of all tests gave in the interval mapping procedure a single significant QTL for disease incidence (likelihood of odds (LOD) score must be higher than 3.4 for a genome-wide confidence level of P<0.05). This QTL had a LOD score of 4.5 and explained 13% of the total phenotypic variation. The allele contributing to resistance originated from the resistant parent LYC 4/78. QTL mapping on each individual experiment gave in all four cases the same QTL region. In each independent experiment occasionally other "minor QTLs" were observed.

Lesion Growth

Lesion growth can best be measured in those disease tests with a high disease incidence. For QTL mapping the average of all 7 disease tests was used and one QTL for lesion growth of B. cinerea was identified above the threshold (LOD 3.4 for a genome-wide confidence level of P<0.05). This QTL had a LOD score of 4.2 and explained 12% of the total phenotypic variation. The positive effect originated from the resistant parent LYC 4/78. The necessity of performing multiple disease tests is illustrated because in only one single repetition a LOD profile above the threshold was found. A QTL for lesion growth was found on chromosome 1 (QTL-1h), and a QTL for disease incidence was found on chromosome 2 (QTL-2h). These QTLs, as well as the QTL denoted QTL4hA are the subject of co-pending application PCT/NL2005/000762.

2.8. Confirmation of QTLs in a Bioassay

The $F_1$ plant of the cross Moneymaker×LYC 4/78 was twice backcrossed with Moneymaker and the 59 progeny plants were screened for the presence of the two identified QTL-regions (QTL-1 h and QTL-2h) using AFLP markers. Plants, heterozygous for one of the two identified QTLs, were selected and selfed to obtain two $BC_2S_1$ populations. A total of four disease bioassays were performed with each $BC_2S_1$ genotype. The data of both $BC_2S_1$ subpopulations, analyzed with SPSS, showed normal distributions for lesion growth, but not for disease incidence as some subclasses were observed.

All $BC_2S_1$ plants were AFLP genotyped with the same 10 primer combinations as described for the $F_2$ population in section 3.3 above. The average lesion growth in the population segregating for the lesion growth locus was 5.3 mm/day while in the other population an average lesion growth of 6.3 mm/day was observed. Not a single plant had a lesion growth as low as the resistant parent LYC 4/78. For disease incidence, however, plants with a lower disease incidence then the resistant parent LYC 4/78 were observed. The average disease incidence for both $BC_2S_1$ populations was equal (57-59%).

The positive effect of each QTL was confirmed in the $BC_2S_1$ populations. The QTL for disease incidence decreased the chance of infection with 17% (46% of the parental variation) and the QTL for lesion growth reduced fungal growth with 1.3 mm/day (33% of the parental variation).

Only a part of the variation could be explained by the effect of both QTLs. Some additional ("minor") QTL loci were identified.

During analysis of data of disease tests obtained from both $F_2$ and $BC_2S_1$ genotypes, one major QTL for disease incidence was identified (QTL-2h). Besides this QTL, other "putative" QTL loci for disease incidence were identified. Using this information cofactors were selected to perform a restricted 'multiple QTL mapping' (MQM) procedure on the $F_2$ dataset. In this analysis, one additional "minor" QTL loci for disease incidence was identified (QTL-4hA). A QTL is denoted as "minor" when its score is below the significance threshold of LOD 3.4. The effects however are believed to be real QTL effects.

QTL-4hA is located on chromosome 4 and reduces disease incidence.

2.9 Conclusions of Disease Assay and QTL Mapping

The bioassay for measuring resistance to *B. cinerea* has proven to be a valuable tool. However, a still large and unknown variation appears to influence the development of the infection process. This large non-genetic variation can be minimized by using standardized procedures and by performing many independent replications. The variation can be caused by the greenhouse conditions changing from week to week (day length, hours of sunlight and temperature) causing differences in physiological conditions of the stem. Also, small variations in the preparation of the fungal inoculum may play a role in the variation of the infection process. Another observation is that the development of the disease can also be affected by the microclimate in the trays in which the stem pieces were placed. Ten different experimental trays were used for the $BC_2S_1$ bioassays. Statistical analysis was used to compensate for variation between and within experiments. Experiments with the highest average disease incidence were the most informative for measuring lesion growth while experiments with a more moderate disease incidence were more informative. Disease incidence and lesion growth are independent traits, since no linear correlation between the two traits could be observed.

Quantitative trait loci for resistance against *B. cinerea* in tomato were identified in the $F_2$. These identified QTLs were confirmed in $BC_2S_1$ populations and explained 46% and 33% of the parental variation for disease incidence and lesion growth, respectively. These results suggest that not all QTLs conferring resistance to *B. cinerea* were detected in the original $F_2$ mapping population. In both $BC_2S_1$ populations plants were found with higher resistance levels as the resistant parent LYC 4/78. This is indicative for the presence of additional resistance loci segregating in the $BC_2S_1$ population. An additional segregation of resistance was surprising because it may have been expected that already large parts of the genome of the two $BC_2S_1$ populations were homozygous Moneymaker.

2.10 Confirmation of Effect of Individual QTLs in Greenhouse Conditions

Plants containing either of the QTLs described above were placed in an *S. lycopersicum* background using the method described in FIG. 2. $BC_2S_2$ lines were placed in the greenhouse in soil and grown under standard practice conditions in the Netherlands. After 3 months plants were inoculated by placing an agar disc containing *Botrytis* in a wound in the main stem. The wound was subsequently closed using Parafilm®. Three weeks after inoculation stem lesion length was measured (in cm) (For more details see below). Results are listed in Table 7. Clearly, lines containing the QTL for lesion growth show an extreme reduction in lesion size.

TABLE 7

Average stem lesion length of *Botrytis cinerea* lesions in adult plants of *S. habrochaites* accession LYC 4/78 and *S. habrochaites* LA 1777, three weeks after inoculation.

| Line | Repeat | Average stem lesion length (cm) | St. dev. | Background | Comments/QTL |
|---|---|---|---|---|---|
| 21 | a*** | 4.2 | 1.1 | GT | Susceptible control |
| 21 | b | 3.6 | 0.9 | GT | Susceptible control |
| 22 | a | 3.0 | 0.0 | Durintha | Partially resistant control |
| 22 | b | 5.0 | 2.9 | Durintha | Partially resistant control |
| 23 | a | 5.6 | 3.0 | Tradiro | Relatively susceptible control |
| 23 | b | 6.0 | 3.3 | Tradiro | Relatively susceptible control |
| 26 | a | 3.2 | 0.8 | BChirs3 | QTL-2h |
| 26 | b | 2.6 | 0.9 | BChirs3 | QTL-2h |
| 26 | c | 2.6 | 1.3 | BChirs3 | QTL-2h |
| 26 | d | 3.2 | 2.2 | BChirs3 | QTL-2h |
| 28 | a | 2.6 | 0.5 | BChirs5 | QTL-1h |
| 28 | b | 2.0 | 0.0 | BChirs5 | QTL-1h |
| 28 | c | 2.0 | 0.0 | BChirs5 | QTL-1h |
| 28 | d | 2.0 | 0.0 | BChirs5 | QTL-1h |
| 373 | e | 4.3 | 0.6 | LA 1777 | QTL-10 containing source of WO02/085105 |
| 373 | f | 4.3 | 0.2 | LA 1777 | QTL-10 containing source of WO02/085105 |
| 374 | e | 4.8 | 0.6 | BC chrs 10 | Introgr. line from *S. lycopersicum* x LA 1777 |
| 374 | f | 4.5 | 0.0 | BC chrs 10 | Introgr. line from *S. lycopersicum* x LA 1777 |
| 375 | e | 4.2 | 0.3 | BC chrs 10 | Introgr. line from *S. lycopersicum* x LA 1777 |
| 375 | f | 4.2 | 0.2 | BC chrs 10 | Introgr. line from *S. lycopersicum* x LA 1777 |
| 376 | e | 4.3 | 0.3 | BC chrs 10 | Introgr. line from *S. lycopersicum* x LA 1777 |
| 376 | f | 5.0 | 0.7 | BC chrs 10 | Introgr. line from *S. lycopersicum* x LA 1777 |
| 377 | e | 4.2 | 0.3 | BC chrs 10 | Introgr. line from *S. lycopersicum* x LA 1777 |
| 377 | f | 4.3 | 0.2 | BC chrs 10 | Introgr. line from *S. lycopersicum* x LA 1777 |

TABLE 7-continued

Average stem lesion length of *Botrytis cinerea* lesions in adult plants of *S. habrochaites* accession LYC 4/78 and *S. habrochaites* LA 1777, three weeks after inoculation.

| Line | Repeat | Average stem lesion length (cm) | St. dev. | Background | Comments/QTL |
|---|---|---|---|---|---|
| 378 | e | 4.8 | 0.2 | BC chrs 10 | Introgr. line from *S. lycopersicum* x LA 1777 |
| 378 | f | 4.6 | 0.4 | BC chrs 10 | Introgr. line from *S. lycopersicum* x LA 1777 |
| 68 | e | 2.0 | 0.0 | parv1 | QTL-3p + QTL-4p |
| 68 | f | 2.0 | 0.0 | parv1 | QTL-3p + QTL-4p |
| 78 | e | 2.0 | 0.0 | parv2 | QTL-9p + QTL-4p |
| 78 | f | 2.0 | 0.0 | parv2 | QTL-9p + QTL-4p |

***a, b, c and d are repeats whereby each repeat represents 5 plants; e and f are repeats whereby each repeat represents 3 plants; GT is Moneyberg with TMV resistance; Durintha is a hybrid with partial resistance according to growers; Tradiro is a hybrid, susceptible to *Botrytis* according to growers; BChirs indicates backcross lines resulting from *S. habrochaites* LYC 4/78 introgressions; LA 1777 is wild species accession *S. habrochaites* LA 1777; BC chrs 10 indicates backcross lines with introgression at chromosome 10 from *S. habrochaites* LA 1777; parv indicates lines resulting from *S. neorickii* introgressions.

2.11. The Level of Resistance to *Botrytis* Conferred by *S. habrochaites* LYC 4/78 QTLs is Higher than the Level of Resistance Conferred by *S. habrochaites* LA 1777 QTLs at Chromosome 10

The level of resistance in plants containing the *S. habrochaites* LYC 4/78 QTLs described herein was compared to that of *S. habrochaites* LA1777, the source of WO02/085105 that contains a QTL for partial *Botrytis* resistance on chromosome 10, and to introgression lines derived therefrom with introgressions at chromosome 10.

Lines were placed in the greenhouse in soil and grown under standard practice conditions in the Netherlands. After 3 months plants were inoculated by placing an 0.5 cm×0.5 cm agar disc containing *Botrytis* in a vertical stem wound of 2 cm length in the main stem. The wound was subsequently closed using Parafilm®. Three weeks after inoculation stem lesion length (length of discolored tissue dotted with fungal growth) was measured (in cm) from top of the lesion to the bottom of the lesion. Results are listed in Table 7. It was observed that lines containing the QTLs from *S. habrochaites* LYC 4/78 showed a higher level of resistance to *Botrytis* than the LA 1777 source and IL-lines. Former lines showed less lesion growth on the stem and therefore exhibit a higher level of resistance to *Botrytis* then the lines derived from LA 1777 (See Table 7). Where a lesion length of 2.0 cm is recorded, only the original wound could be measured and no fungal growth was observed, which indicates a high level of resistance. Thus, a stem lesion length of 2 cm indicates absence of net growth.

EXAMPLE 3

Mapping Partial Resistance to *Botrytis cinerea* in an Interspecific Tomato Population

*S. lycopersicum* cv Moneymaker×*S. habrochaites* Accession LYC 4/78

Introduction

In order to make for a more effective breeding process, involving the selection of candidate parent plants having the proper genetic constitution, it is necessary to have at one's disposal one or more genetic markers that indicate the presence of that genetic constitution in at least one of the candidate parent plants. This process, which includes crossing of the selected plants and is termed marker assisted selection (MAS), efficiently transfers favourable parental alleles from a donor to a recipient population and ensures that breeding is no longer dependent on coincidence and is economically much more effective in terms of development costs.

Resistance to *B. cinerea* was identified in the wild accession *Solanum habrochaites* LYC 4/78 (Urbasch, 1986; Example 1). To study the genetics behind this resistance, an $F_2$ mapping (n=174) population of the cross between *S. lycopersicum* cv. Moneymaker and *S. habrochaites* LYC 4/78 was developed (see Example 3). Initially, two QTLs for resistance to *B. cinerea* were identified in the $F_2$ mapping study (QTL-1h and QTL-2h as described above). Later on a third QTL (QTL-4hA) was detected in segregating $BC_2S_1$ progenies, a QTL from which the effect could only be observed in the absence of QTL-2h. Using a 2-way ANOVA analysis a significant epistatic interaction between both QTLs was identified in the $F_2$ dataset. Some genotypic classes are represented at a low frequency and therefore large $F_2$ populations are needed to detect QTL interactions (Tanksley 1993). In our $F_2$ population, three plants were homozygous *S. lycopersicum* for QTL-1h and QTL-2h while 12 plants were homozygous *S. habrochaites* for both. Using a 2-way ANOVA, a significant interaction was detected between both loci. Analysis of mean observations of each of the classes showed then when QTL2 is homozygously *S. habrochaites* there is no additional effect of QTL-4hA.

One disadvantage of QTL-mapping in interspecific segregating F2 populations is the wide variation of phenotypes that easily mimics QTLs with minor effects. Another disadvantage is the inability to do repeated tests as each F2 plant is a unique genotype. Alternatively, a genetic library consisting of a set of introgression lines (IL) can be used for mapping purposes. Each IL ideally harbors a single, defined chromosome segment that originates from the donor species in an otherwise uniform genetic background (Zamir 2001). Such lines have an increased ability to identify QTLs because: I) phenotypic variation between the line and the control cultivar is associated with the introgressed segment; II) each line contains mostly more then 95% of the recurrent cultivated parent genome and minor quantitative effects can easily be identified by comparison with the recurrent parent; III) epistatic effects caused by other regions of the wild genome are not present. Unlinking negative epistatic interactions may thus lead to identification of novel QTLs (Eshed et al. 1995); IV) each line is homozygous and immortal and thus allowing multiple testing (in multiple environments) and V) sterility problems are nearly absent due to the fact that the genetic constitution of each line is largely identical to the cultivated variety.

The first developed IL population already dates back to 1965 (Wehrhahn et al.), the majority of the IL populations were developed during the last decade. Besides tomato, IL populations were developed for barley (von Korff et al. 2004), cabbage (Ramsay et al. 1996), lettuce (Jeuken et al. 2004), melon (Eduardo et al. 2005), rice (Lin et al. 1998) and wheat (Pestsova et al. 2001). All these IL populations were developed using marker assisted selection (MAS) but different strategies indicated by the different number of backcross and inbreeding generations to obtain the IL populations were used. A second difference in the strategy was the choice which marker system (i.e. which type of markers) was used to develop the IL population. Four of the populations mentioned above were developed using SSR markers.

Within *Solanum*, ILs have been developed for *Solanum pennellii* LA716 (Eshed et al. 1994), *S. habrochaites* LA1777 (Monforte et al. 2000a) and *Solanum lycopersicoides* LA2951 (Canady et al. 2005). Such populations have shown to be extremely helpful in the identification of quantitative traits (Eshed et al. 1995; Rousseaux et al. 2005), fine mapping of QTLs (Fridman et al. 2004; Monforte et al. 2001; Monforte et al. 2000b) and QTL cloning (Frary et al. 2000; Fridman et al. 2000; Ku et al. 2001).

Currently, one *S. habrochaites* LA1777 IL population exists in a determinate growing *S. lycopersicum* E6203 (Monforte et al. 2000a).

In this Example we describe the development of a second IL population of *S. habrochaites*, now based on introgressions from *S. habrochaites* LYC 4/78 in the background of the indeterminate growing cultivated tomato *S. lycopersicum* cv. Moneymaker, and the use of the lines in the identification of QTLs for resistance to *B. cinerea*.

Material & Methods

Plant Material and Development of the ILs

Figure 6:
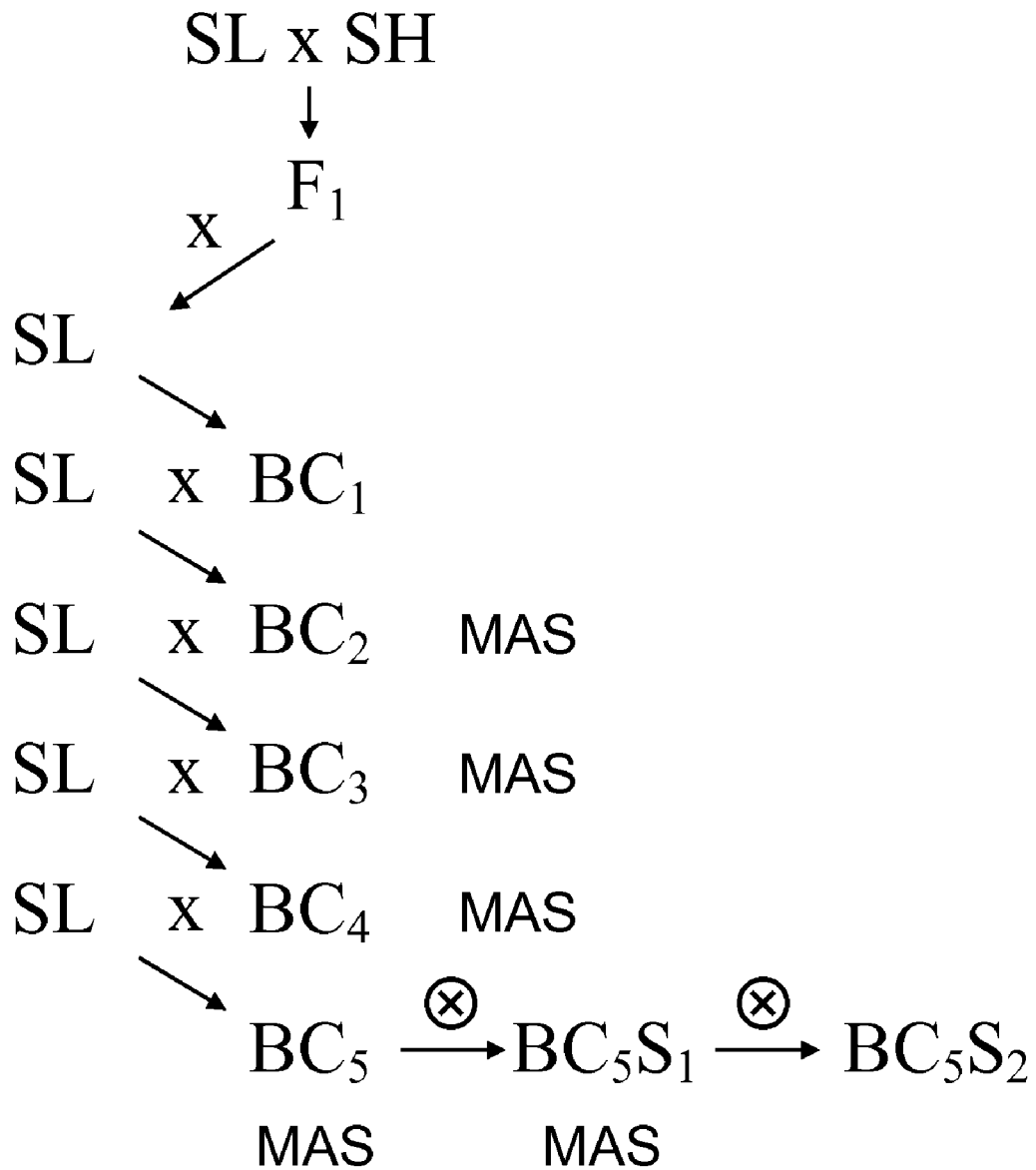
FIG. 6 shows the backcross and selection strategy used to obtain the *S. habrochaites* LYC 4/78 IL population introgressed in the *S. lycopersicum* cv. Moneymaker genetic background described in Example 4.

An interspecific cross between *S. lycopersicum* cv. Moneymaker (hereafter referred as SL) and *S. habrochaites* LYC 4/78 (hereafter referred as SH; seed batch of 1978) was made to produce $F_1$ seeds. Seeds of SH were obtained from the gene bank located at the Institute for Plant Genetics and Crop plant research, Gatersleben, Germany. One $F_1$ plant was self pollinated to obtain $F_2$ seeds and backcrossed to SL to obtain $BC_1$ seeds. The $F_2$ seeds were initially used for the construction of the genetic linkage map. The $BC_1$ seeds were used to develop the ILs (FIG. 6).

Marker Analysis

Genomic DNA was isolated from two young (rolled up) leaves using a CTAB based protocol according to Steward et al. (1993), adjusted for high throughput DNA isolation using one ml micronic tubes (Micronic B V, Lelystad, The Netherlands) and grounded using a Retsch 300 mm shaker at maximum speed (Retsch B V, Ochten, The Netherlands).

AFLP™ analysis (Vos et al. 1995) of each backcross and IL was done and the AFLP fragments were resolved on a LI-COR 4200 DNA sequencer, essentially following the method published by Myburg (2001). The selective Pst primer was labeled with an IRD700 or IRD 800 fluorescent label. AFLP gel images were scored using the AFLP-Quantar™Pro software package World Wide Website keygene-products.com Primer and adapter sequences are described by Bai et al (2003).

Sets of CAPS primers were obtained from the "Solanaceae Genomics Website" (Worldwide Website: sgn.cornell.edu) or designed on sequences of genomic or cDNA clones available from the same source. Polymorphisms between *S. habrochaites* and *S. lycopersicum* were determined using the CAPS digestion approach described by Brugmans et al (2003). Marker sequences, PCR conditions, and specific restriction endonucleases used to genotype are presented in table 30. PCR products were generally separated using a 2.5% agarose gel. In Table 31 the different digestion products which discriminate between *S. lycopersicum* and *S. habrochaites* are indicated for each of the markers of Table 30 found in the QTLs of interest.

Graphical Genotype

Graphical genotypes for each backcross and the ILs were obtained using the software program GGT (van Berloo, 1999). For the calculation of introgression size and genome percentages, the half-intervals flanking a marker locus were considered to be of the same introgression as implemented by the GGT software. Missing marker data were estimated from the flanking markers; they were assumed to have the same genotype of the two flanking markers, if these had identical genotypes. If the two flanking markers had contrasting genotypes, then the data were recorded as missing.

Disease Evaluations

To assess resistance, 16 incomplete randomized blocks were used with in total 11 replications for each IL. Each block contained at least two SE plants and one plant of *S. lycopersicum* cv. Durinta. Durinta is a commercial cultivar producing truss tomatoes with a long shelf life and displays a certain (but not high) level of resistance. Six weeks after sowing, plants were transplanted to full soil compartments and grown in a regime of 15 degrees at night/19 degrees during the day and a photo period of 16 hours. After 11 weeks, two lesions of approximately 15 mm were cut into the stem of each plant using a kitchen knife. Each wound was inoculated with a 1 $cm^2$ plug of *B. cinerea* B05.10 containing agar (Benito et al (1998)), and closed with tape. A second inoculation was performed two weeks later. During the test, plants were watered at the beginning of the evening to maintain a humid climate during the night. Disease progress was measured 9, 12 and 22 days after inoculation using a caliper. The disease progress was described according to the following parameters: corrected lesion size (LS) after 12 days (i.e., the total length of the lesion minus 15 mm of the wound), percentage of outgrowing lesions (DI), and lesion growth rate expressed as the difference in corrected lesion size measured at days 9 and 12 and expressed in mm/day (LG).

Statistical Analysis

Statistical analysis was performed using the SPSS 12.0 software package (SPSS Inc, Chicago, U.S.A.). Using the general linearized model (GLM) procedure, means for each IL/trait were estimated. Mean values of the traits measured were compared to the control genotype SL using a Dunnett test (Dunnett, 1955) and probabilities smaller then 0.05 were considered as significant. To analyse LG and LS, a square root transformation was applied to normalize the data of both traits. Correlations between traits were calculated using a Pearson-correlation coefficient.

Results

IL Population

Figure 7:
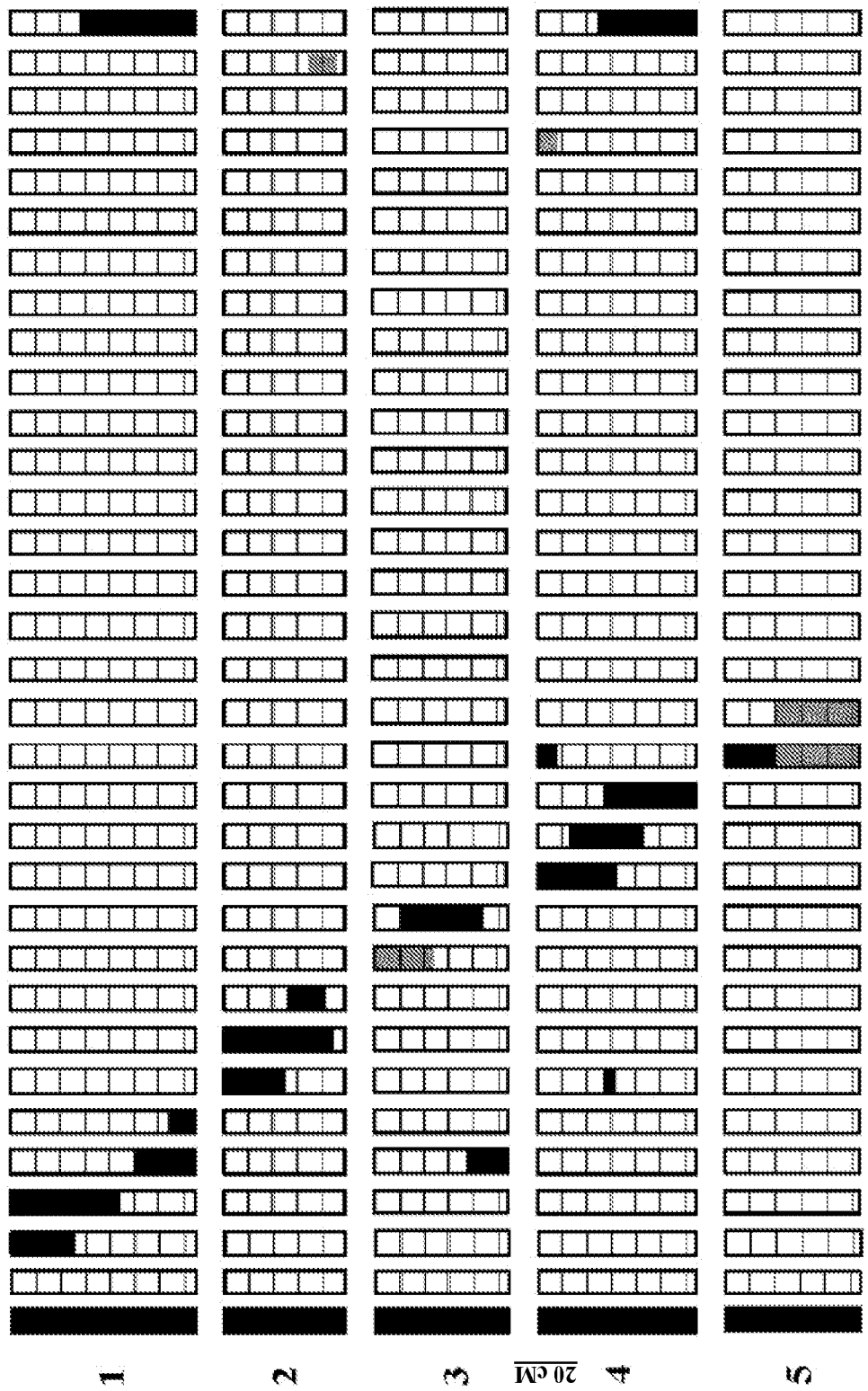
FIG. 7 shows a graphical genotype of the *S. lycopersicum* cv. Moneymaker×*S. habrochaites* LYC 4/78 introgression line population used in Example 4. All chromosomes are drawn to scale in 20 cM segments according to the $F_2$ genetic linkage map. Some regions were added to the ends of Chromosomes 3, 4, 5 and 9 (CAPS markers). Homozygous introgressions from *S. habrochaites* are presented in black, while heterozygous introgressions are marked using a diagonal pattern (grey).
Figure 7:
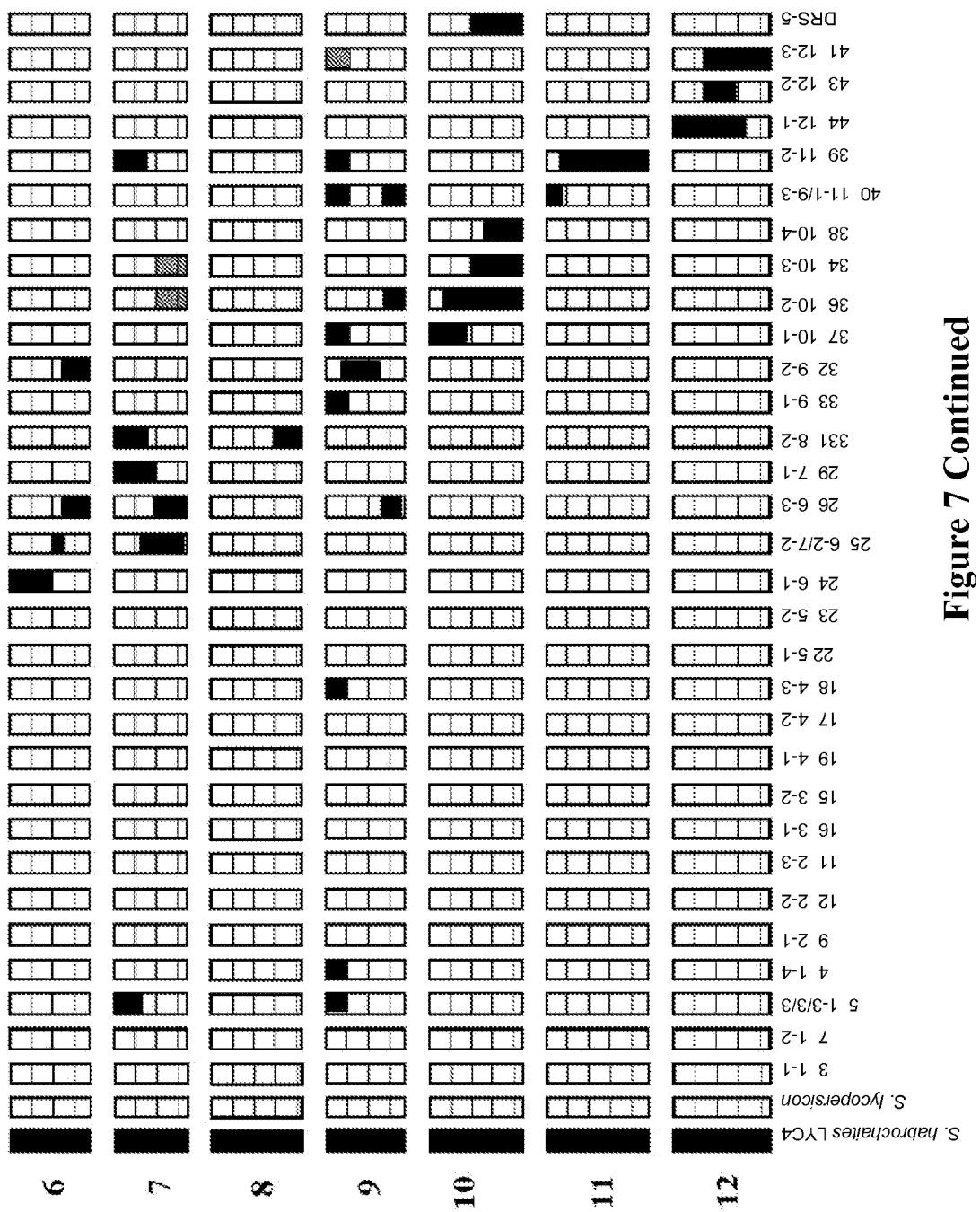
Figures 8, 8A:
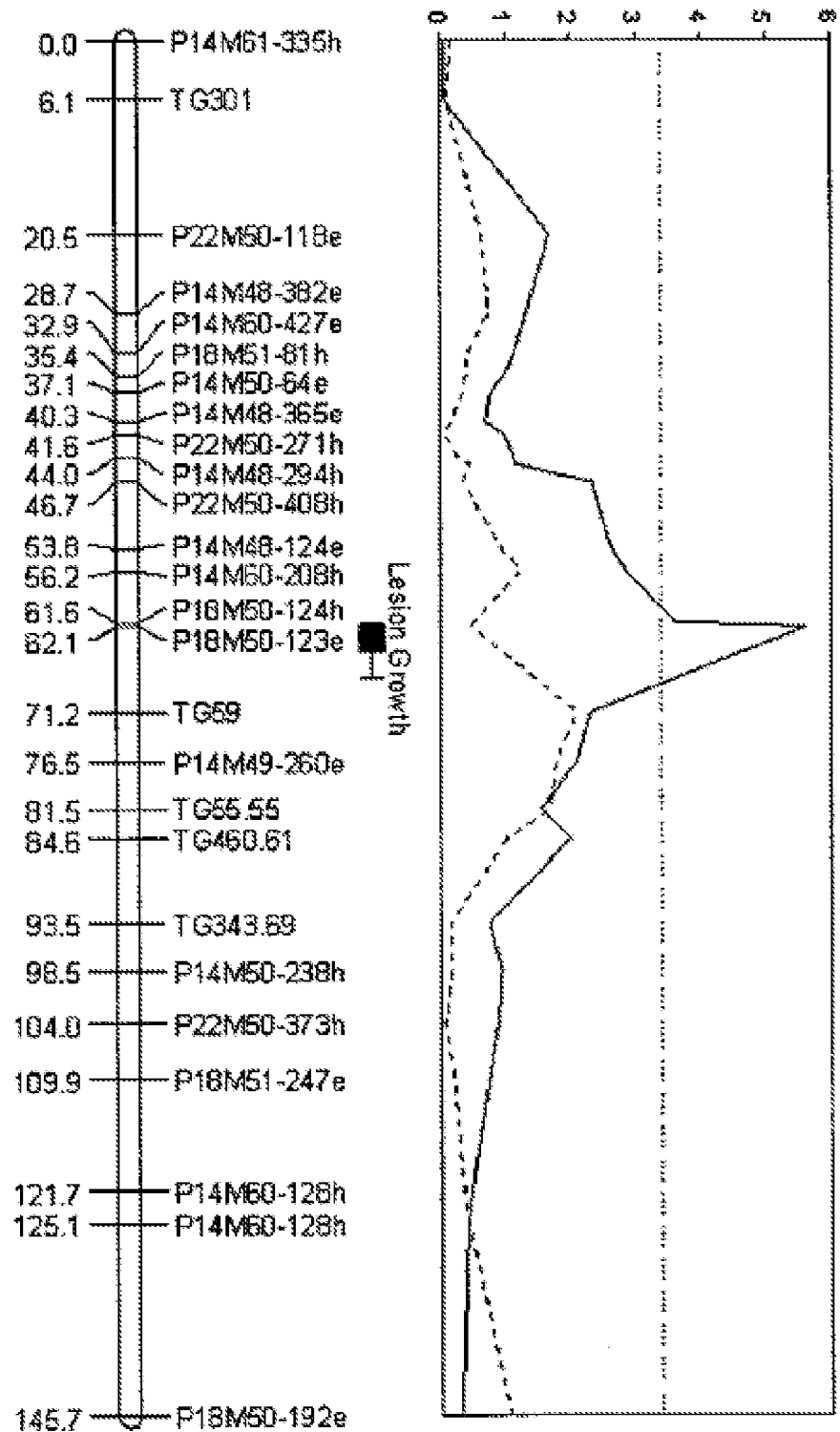
FIG. 8 shows the position of quantitative trait loci (QTLs) for resistance to *B. cinerea* originating from *S. habrochaites* LYC 4/78 with the linkage maps representing chromosome 1, 2 and 4 and indicate QTLs indicated in this application as QTL-1h, QTL-2h and QTL-4hA.
Figures 8, 8B:
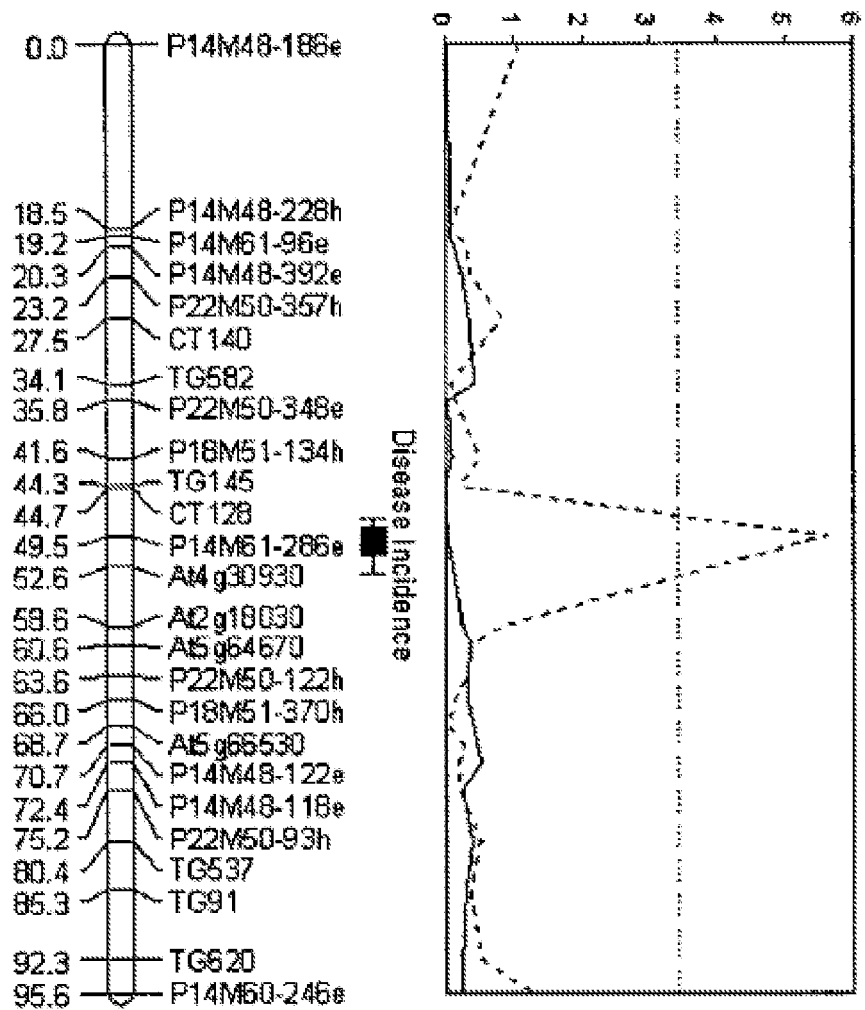
Figures 8, 8C:
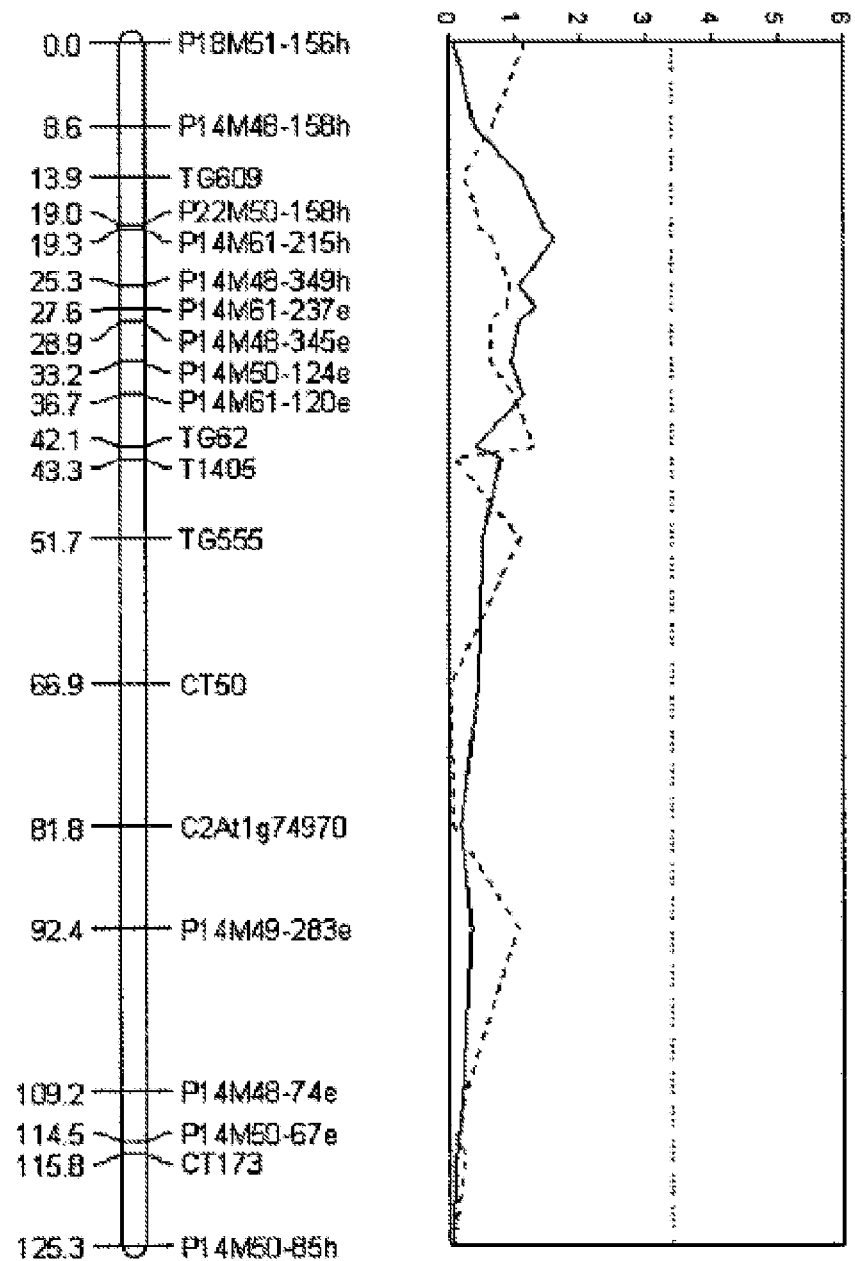

An introgression line (IL) population of *S. habrochaites* LYC 4/78 (SH) in the genetic background of *S. lycopersicum* cv. Moneymaker (SL) was developed. One $F_1$ plant derived from the cross between SL and SH was backcrossed to SL (FIG. 6). Subsequently a random set of 14 $BC_1$ plants was backcrossed to SL to obtain a $BC_2$ progeny (n=59). All $BC_2$ plants were genotyped and a selected set was backcrossed to SL. This set was chosen in such a way that the combined introgressions covered as much as possible of the SH genome while selecting recombinants in such a way that each alien chromosome will be represented by three ILs. This process of selection and backcrossing was repeated until $BC_5$. 31 selected $BC_5$ plants, mainly containing one or two introgressions were self pollinated. Up to 12 plants of each of the 31 $BC_5S_1$ families were self pollinated and screened with AFLP markers to obtain a $BC_5S_2$ progeny (n=44) homozygous for the introgression. The markers of the 44 ILs were screened once more and a core set of 30 ILs was chosen. This core set represents the maximum coverage of the SH genome in as few as possible ILs (FIG. 7). The core set consists of 15 ILs harboring a single introgression, 10 ILs containing two introgressions, 4 ILs containing three introgressions while one IL still contained four homozygous introgressions. On average each IL contained 60 cM (=5.2%) of the SH genome and the length of the introgressions varied between 20 (1.7%) and 122 cM (10.6%). Our IL population covers 95% of the length of the original $F_2$ linkage map.

However, we realize this $F_2$ linkage map is not completely covering the genome. This is illustrated by additional CAPS analysis on chromosomes 3 (top of the short arm), 4 (top of the short arm), 5 (long arm) and 9 (top of the short arm) where CAPS markers revealed introgressions with no markers in the AFLP based $F_2$ linkage map. The size of these introgressions was estimated based on the high density RFLP map (Tanksley et al. 1992; World Wide Website sgn.cornell.edu). Since no previous screening was applied for the top of Chromosome 3 the IL for this region is heterozygous. Plants, selected to be homozygous SH for IL5-1 and 5-2 failed to set seeds therefore these lines were maintained in their heterozygous state. No ILs containing the top of the short arm of Chromosome 8 and the bottom of the long arm of Chromosome 2 were present. Introgressions, on the top of the short arm of Chromosome 7 and 9 are present in multiple ILs. Selection for the top of Chromosome 9 was only possible after development of CAPS markers specific for this region.

Disease Evaluations

The population of 30 ILs was grown in eleven replicates in an incomplete randomized block design, inoculated and evaluated for disease symptoms. A set of fairly resistant and susceptible controls was included in the test. On 9, 12 and 22 days after inoculation the disease progress was measured and evaluated by scoring the following three parameters: Chance of outgrowing infections, or disease incidence (DI), corrected size of the outgrowing lesion (LS) and lesion growth rate (LG). The resistant parent SH hardly showed any symptoms (Table 8, Table 9) while 73% of the SL lesions were outgrowing.

TABLE 8

Mean phenotypic observations for LS, LG and DI of the most resistant ILs and control lines.

| IL | N | Corrected lesion size $^a$ (mm) LS | | Lesion growth $^a$ (mm/day) LG | | Outgrowing lesions (%) DI | |
|---|---|---|---|---|---|---|---|
| 1-3/3-3 | 29 | 30 | ** | 1.7 | ** | 45 ± 9.1 | ** |
| 1-4 | 44 | 34 |  | 2.4 | * | 37 ± 6.4 | ** |
| 2-2 | 44 | 26 | * | 2.8 |  | 37 ± 6.5 | ** |
| 4-1 | 44 | 26 | ** | 2.5 | * | 41 ± 6.4 | ** |
| 6-1 | 44 | 44 |  | 3.6 |  | 49 ± 6.5 | * |
| 9-2 | 44 | 33 |  | 3.1 |  | 49 ± 6.4 | * |
| 11-2 | 44 | 33 | * | 3.2 |  | 34 ± 6.4 | ** |
| 12-3 | 24 | 21 | ** | 2.3 |  | 24 ± 8.6 | ** |
| SL | 156 | 46 |  | 4.6 |  | 73 ± 4.0 |  |
| SH | 44 |  |  |  |  | −3 ± 6.4 | ** |
| DRS5 | 39 | 20 | * | ND$^b$ |  | 15 ± 6.9 | ** |
| Durinta | 68 | 29 | ** | 2.3 | ** | 42 ± 5.5 | ** |

$^a$ first observation of a measurable lesion was after 12 days.
$^b$ Not determined.

Means of each IL per trait (Table 9) were compared to the mean of *S. lycopersicum* cv Moneymaker (SL) using an Dunnett test and significant differences are marked with * or ** (p < 0.05, p < 0.01 respectively).

TABLE 9

Estimated mean phenotypic observations for LS, LG and DI. The table is sorted on DI.

| IL | N | Corrected lesion size $^a$ (mm) LS | | Lesion growth $^a$ (mm/day) LG | | Outgrowing lesions (%) DI | |
|---|---|---|---|---|---|---|---|
| 12-3 | 24 | 21 | ** | 2.3 |  | 24 ± 8.6 | ** |
| 11-2 | 44 | 33 | * | 3.2 |  | 34 ± 6.4 | ** |
| 1-4 | 44 | 34 |  | 2.4 | * | 37 ± 6.4 | ** |
| 2-2 | 44 | 26 | * | 2.8 |  | 37 ± 6.5 | ** |
| 4-1 | 44 | 26 | ** | 2.5 | * | 41 ± 6.4 | ** |
| 2-1 | 44 | 30 | * | 3.0 |  | 41 ± 6.4 | ** |
| 1-3/3-3 | 29 | 30 | ** | 1.7 | ** | 45 ± 9.1 | ** |
| 4-2 | 42 | 33 |  | 3.8 |  | 45 ± 6.7 | * |
| 3-2 | 44 | 35 |  | 4.2 |  | 46 ± 6.5 | * |
| 3-1 | 43 | 41 |  | 2.8 | * | 47 ± 6.6 |  |
| 1-2 | 40 | 33 |  | 3.4 |  | 47 ± 6.7 |  |
| 11-1/9-3 | 44 | 36 |  | 4.3 |  | 48 ± 6.5 | * |
| 9-2 | 44 | 33 |  | 3.1 |  | 49 ± 6.4 | * |
| 6-1 | 44 | 44 |  | 3.6 |  | 49 ± 6.5 | * |
| 7-1 | 44 | 35 |  | 3.1 |  | 50 ± 6.4 |  |
| 4-3 | 20 | 29 |  | 2.8 |  | 51 ± 9.6 |  |

TABLE 9-continued

Estimated mean phenotypic observations for LS, LG and DI. The table is sorted on DI.

| IL | N | Corrected lesion size $^a$ (mm) LS | | Lesion growth $^a$ (mm/day) LG | | Outgrowing lesions (%) DI | |
|---|---|---|---|---|---|---|---|
| 12-1 | 44 | 35 | | 4.7 | | 51 ± 6.4 | |
| 12-2 | 43 | 37 | | 4.0 | | 52 ± 6.4 | |
| 6-2/7-2 | 44 | 39 | | 3.7 | | 55 ± 6.3 | |
| 2-3 | 44 | 44 | | 3.5 | | 58 ± 6.5 | |
| 8-3 | 44 | 43 | | 3.9 | | 59 ± 6.5 | |
| 10-1 | 43 | 47 | | 4.3 | | 60 ± 6.6 | |
| 5-1 | 44 | 53 | | 4.8 | | 61 ± 6.6 | |
| 10-2 | 44 | 49 | | 4.4 | | 62 ± 6.5 | |
| 1-1 | 41 | 56 | | 5.9 | | 65 ± 6.7 | |
| 9-1 | 44 | 34 | * | 3.0 | * | 69 ± 6.5 | |
| 5-2 | 43 | 64 | | 5.4 | | 69 ± 6.6 | |
| 10-3 | 44 | 53 | | 4.7 | | 70 ± 6.4 | |
| 10-4 | 44 | 47 | | 4.8 | | 76 ± 6.6 | |
| 6-3 | 44 | 49 | | 4.6 | | 79 ± 6.5 | |
| SL | 156 | 46 | | 4.6 | | 73 ± 4.0 | |
| SH | 44 | | | | | −3 ± 6.4 | ** |
| DRS5 | 39 | 20 | * | ND$^b$ | | 15 ± 6.9 | ** |
| Durinta | 68 | 29 | ** | 2.3 | ** | 42 ± 5.5 | ** |

Means of each IL per trait were compared to the mean of *S. lycopersicum* cv. Moneymaker (SL) using a Dunnett test and significant differences are marked with * or ** (p < 0.05, p < 0.01 respectively).

Within the IL population 14 ILs were identified with reduced disease symptoms (Table 9). A total of 12 ILs showed a significant lower DI. Seven had significantly reduced LS and five a significant lower LG. IL4-1 and IL 1-3/3-3 showed a significant reduction of all three parameters (DI, LG and LS). In the ILs significant lower for DI the range in percentage of outgrowing lesions was from 24-49%. LS and LG varied for the significantly deviating ILs between 21-34 mm and 1.7-3.0 mm/day respectively. The control *S. lycopersicum* cv. Durinta, with a certain level of resistance, was also significant lower for all three parameters and the resistance in each of the seven identified ILs is more or less comparable to this level. In previous experiments a very resistant BC$_2$S$_2$ genotype was selected (DRS 5, see Tables 8 and 9). This line contains three homozygous introgressions representing in total 18% of the SH genome (FIG. 7). This line was the most resistant line in the test described above. It had a significant lower DI (15%) and the LS was also significantly reduced. Compared to *S. lycopersicum* cv. Durinta, the 2.8 fold reduced DI of this line is significantly lower showing the potential of pyramiding multiple alleles conferring resistance to *B. cinerea*.

Effect of Stacking Introgessions

When analyzing the various introgressions present in individual IL lines (FIG. 7) and comparing those with their individual effects on resistance as shown in Table 9, one may infer the effects of stacking. As can be seen in lines 9-1, 9-2, 11-2 and 12-3 the stacking of introgressions may have effect.

It is concluded fro instance that the introgression at chromosome 6 in line 9-2 has no effect, since an identical introgression in line IL6-3 provides no resistance.

Likewise, an introgression at chromosome 7 in line 11-2 has no effect (compare to line 7-1 and 8-2).

The two resistance patterns (DI and LS) as present in 11-2 are not the result of the introgression on chromosome 11 only. The reduction in lesion size (LS) in this line could be due to an introgression from chromosome 9 (compare similar introgressions in 9-1 whereas a reduction in disease incidence is never found in association with the introgression of 9-1 alone. Therefore, the reduction in disease incidence must be due to the introgression from chromosome 11. Thus, in line 11-2 the total resistance is the result of various introgressions.

Similarly, reduced % outgrowing lesions in line 12-3 compared to line 9-1 could be due to introgression at chromosome 12, whereas the reduced correct lesion size could be due to the introgression from chromosome 9. Hence, also here the combined presence of multiple introgressions results in improved resistance.

Linkage Between IL and Disease Data

Using a greenhouse bioassay we identified a set of ILs containing introgressions responsible for an increased resistance to *B. cinerea*. Three regions, located on Chromosome 2, 4 and 6 unambiguously contain a gene(s) for increased resistance. The other ILs contain multiple introgressions making it more difficult to pinpoint the resistance genes. IL9-2 contains introgressions on Chromosome 6 and 9. The introgression on Chromosome 6 in IL9-2 is similar to the Chromosome 6 introgression in IL6-3, an IL as susceptible as SL. Thus, we expect the effect of IL9-2 is caused by the introgression on Chromosome 9 and not on Chromosome 6. IL11-2 contains a chromosome 9 introgression smaller than present in IL9-1. Therefore, the reduced DI is expected to be caused by a locus on chromosome 11. The two ILs 1-4 and 12-3 contain introgressions overlapping the Chromosome 9 introgression of IL9-2. Only IL12-3 is significantly more resistant then IL9-2 suggesting a combined effect of the introgressions on Chromosome 9 and 12. Since, ILs 1-4 and 11-2 are not significantly more resistant then IL9-2 we cannot exclude that resistance within these two lines are the result of the introgression of Chromosome 9.

Summarizing; we identified introgressions located on Chromosome 1, 2, 4 (2×), 6, 9, 11 and 12 that are responsible for an increased resistance to *B. cinerea*. The effects on Chromosome 2 and one on chromosome 4 have been previously detected during analysis of F$_2$ and BC$_2$S$_1$ segregating populations of this cross (see Examples 1-3).

Segregation in the F$_2$ of Identified Loci

For all regions, in which an association is found between the introgression and an increased resistance to *B. cinerea*, the original F$_2$ dataset was checked to find a possible explanation why the QTL initially was missed. Both skewness of the marker data and results from the QTL analysis were checked. Introgressions on Chromosome 1 (1:6:6), Chromosome 2 (1:3:2) and Chromosome 9 (1:6) were significantly deviating from the expected 1:2:1 or 1:3 ratio's. For all three regions, a lack of homozygous *S. lycopersicum* alleles is observed. QTL analysis data for both interval mapping and single marker analysis using a Kruskal-Wallis procedure were checked but no evidence was found about the existence of a significant QTL in the dataset of the $F_2$ population on Chromosome 6, 9, 11 and 12.

Marker Sequences as Used Herein

The following Tables provide detailed information on the various RFLP and COS-II markers as indicated in the various linkage maps and as indicated for association with the QTLs of the present invention. The information was directly copied in from the SOL Genomic Network (SGN) database hosted at Cornell University, version of 7 Oct. 2005.

TABLE 10

TG609 RFLP Marker

RFLP Information
Name: TG609
Insert size: 1900
Vector: pGEM4Z
Cutting Site: PST1
Drug Resistance: AMP Forward sequence
GAGACAGCTTGCATGCCTGCAGAGGTGATAAATTCACCAAGGTTTCATAT
TTAGGAAACAAGAAAATTAAAAGATCATTAACACAGATGAAAGGATATGA
CTAGGAGGCAATGACTGATCTTTGACTATCAAATACTTCTCAGGGAAACA
ATGTGAATGGGCTTTTACATGCAGAGATATTGATTGTGATCATGTTGAAG
AACTTAGGAAACATGAAATTAAATGATCATTAACACTGATGCAAGGATAT
GCCAAGTAGGCAAGCAAATTAAGGTTGAACATAAATGTCTGTGATCTTTG
ACTATCAAATATCTTCTCAGAAAAAAAAATGTGAATGCTCATTTACATGC
AGAGATGGCTATTGTGATCATGTGGCTCAGCCTTGAGTCTATATTGAGGT
GCAGACAACATAGTCCCTAACCACATGTGTGATCAAGCAACTTTTTTGAT
GTCCACAGGGTTATAAGTAGGCAACATTTAAGCAAGAAAAAACACAGGAT
CACTATTGAGTCAGCTGCTGTTGCCTGT
(SEQ ID NO: 1)

Reverse sequence
GGAGACAAGCTTGCATGCCTGCAGAGGTGATAAATTCACCAAGGTTTCAT
ATTTAGGAAACAAGAAAATTAAAAGATCATTAACACAGATGAAAGGATAT
GACTAGTAGGCAATGACTGATCTTTGACTATCAAATACTTCTCAGGGAAA
CAATGTGAATGGGCTTTTACATGCAGAGATATTGATTGTGATCATGTTGA
AGAACTTAGGAAACATGAAATTAAATGATCATTAACACTGATGCAAGGAT
ATGCCAAGTAGGCAAGCAAATTAAGGTTGAACATAAATGTCTGTGATCTT
TGACTATCAAATATCTTCTCAGAAAAAAAAATGTGAATGCTCATTTACAT
GCAGAGATGGCTATTGTGATCATGTGGCTCAGCCTTGAGTCTATATTGAG
GTGCAGACAACATAGTCCCTAACCACATGTGTGATCAAGCAACTTTTTTG
ATGTCCACAGGTTTATAAGTAGGCAACATTTAAGCAAGAAAAAACACAGG
ATCACTATTGAGTCAGCTGCTGTTGCCTGTTACTGAG
(SEQ ID NO: 2)

TABLE 11

TG62 RFLP Marker

RFLP Information
Name: TG62
Insert size: 1800
Vector: pUC
Cutting Site: PST1
Drug Resistance: AMP Forward sequence
CAAAATGCTTCAGCTACTGGCTAAATGAAGTATGTTCTCAACATATTCAC
AAGCTTCTGTCTTCGAAGCTCAAGAAGTGTCGGTATTATCTGAATTAAAT
AGTAAAGCAAAGAGATGGTTTTATGTTTCTTAAGCAGCATTTCTTAGCTT
AACGGCCCTCCAGATATATGGTGGACAAAATAGAATCCATTAGATATAAC
AAATGGGATTAGTATAATGATCTTTTACTTTGTTAGATGATCATACTAAC
AGATTGCAAGTTAATCATATCCAACATATTCTGTAGATATTTCACATTGG
CTAGCATGAGGAAAGGTCATGTAGGAAATTGAATAGAGTTCAATTTTGGG
AAAAGTTGCATTGAAGAAGGTAACTTCAACAAACGTGTGAAAAAATCACA
TTTGAGTTGCCCGCTCACCATCGTGATTCCAGTACGAACTACTCAAAAAT
TTACTTTTGAGCCTTAAACATCATTTTAAGCCTTGAAAAGCTGCTTTTGA
AAAGATCTAAGCAAGAT
(SEQ ID NO: 3)

TABLE 11-continued

Reverse sequence
GGAGAATATTGTCACTCTATCAGATAGTTCAAAACTATCGGAGAATGAAA
TGGTCAATTCTTCTCACAAGATATTCATGCCTAGTTGCAGTGTCCGAATT
AACATAACATGCTCAATTTTCATATCTTGCAGCAAAATTTATCATTGAAA
CTCTCTGAGATGGAAACAGAGAACAAAGACCATATTGGAAAGCTTCAATC
AGACATGCAGAAAAAGGAAGATGAGATTCATGTTTTACGCAAGGAAATTG
ACAATTACACGGAAACAGTGGATTCACTGGAGAAGCATGTTACAGAGATT
AACAATAAATTGGAGGAGAAAGATCAGCTTGTTCAGGAACTTCAGGACAA
GGAGAAGCAGTTGGAAGCTGACAGAGAAAAGGTTTTTACTACGGATACTT
TTAGTTCTACAAATTCTATTATAACCAATACAATGTGTTCAAGTGACTAG
TGTTTTGCACCTTGTTGCAGATTCAGGCATCTTTGCTTGCTGCTGAAAGC
AAGCTCACAGAATCCAAAAAGCAGTATGATCAGATGT
(SEQ ID NO: 4)

TABLE 12

TG555 RFLP Marker

RFLP Information
Name: TG555
Insert size: 1600
Vecton pGEM4Z
Cutting Site: PST1
Drug Resistance: AMP Forward sequence
AATTCGGAGCTCACTGCTTCTAATCCTCAGTGAGACTTATTTTCTACATA
TTAAACAATAAGAAATTTACGAAGGAATATTATAGACTGAATTCCTTGGT
GACAAGTATCAAGACATCTTGACCAAGTTTAAAGTTTTGTAGTGGCAGTT
CTTTTAAGCTTTACTTGTGTGAGGTAGACATCAAGGAAGATAAGTAGCAG
CTACTCTTCACGGAGCAGCCCATAGGACACTCAAATTCACTATTGCGAGG
GTCAATCTACCAATTTATGGAACGATACCAGTAAAGTCATTTTTATGTAA
ACATCAGACAGCTTTTGACTAAGCAGAGACATGAATAAGTTCTATTTGTT
AGAAGTCGAAGAGACAAATAAGTTAATTTCACCTATGCTATAAAAGAGGA
CTCTTATAGTTATAAATACAGTACATTTTATTAAGGGTTCTAATTGTTGA
CTATGATAGCAAGCATGCCGTACTAATT
(SEQ ID NO: 5)

Reverse sequence
ACATTTTGAGGAAGACAGGAGTTATGTATCGCCATCTGGTGTGCTCCAAG
AACATGACAGATATAAAAGACCGCGGGGTGCACCAGAGAAATGTTGCATT
GGAGCATATTGAACATCATAGGCTCAATGGAATTGTTTACTTTGCAGATG
ATGATAATATCTACTCACTTGAGTTGTTTGAGAGCATTAGATCGATCAAG
TAAGTTGAGATTCATCAGTCTTGTTTACATGACTTGTCTTTGTTTTGTCC
TGCTGTGAGCATGTTCAGGATGATGTTATGTGCTTTATGTAGATGTTCAA
GTCGATAATAGTGAATAGTCTAGAGCTATTTCACATATATTACAACTTCA
CTAACAAATTCTTTTCCTGGTGTCCTCGGTTCATCACTCTTCATAGTTAT
AAGAATAACAGTTGTAGATTAGACCACTGGTCGTGTGATTTTTGGACTTA
ATTATTATCTCAATTCTTCCTCAAAATAGCAGTCCTTAGATTAGAAGCTG
AGG
(SEQ ID NO: 6)

TABLE 13

CT50 RFLP Marker

RFLP Information
Name: CT50
Insert size: 1600
Vector: pBLUESC
Cutting Site: EcoR1
Drug Resistance: AMP Forward sequence
CTTTTTTTTTTTTTTATATATTGTGGTATAGATTATTATATAATAACAA
GGTGAATTAACATGAGAAATGAATAATTGTCACATTCTTGTTCTGTCCAT
TTTCCAGTAGCGGCTAGTTGGAAAATTTGTTGTAACATGTAACACAGGCT
GTCCACATTCTACTCCAGAGAGAAGTTGGTAAGTAGTGGGGGCAAAAGA
TAGAGACCCCAATAGCTATCAATTCACTTTGTTGACAATCAAGATTTGAG
AAAAAAGATCAAAACTTTACCAACTTAGATAGCTCCATAATCAACTGTAG
GTACAATTCTTTAGTGAAATTGCGGCGTTCATCTTCTGGGGACGAAGAGT
AAGTAGACAATCAATTGTCTTGTAGAACTTGGGCTTTACCATTTTCCCTA
GGACATAAGCTCTTGATCGAAGCTTGAAGTTTAATTTTAGTGGCACTGGT
AATG
(SEQ ID NO: 7)

TABLE 13-continued

Reverse sequence
TTTTTTTTTTTTTTAGCCAAAATGCATACAAAAACTGATTCAGAAGATA
CGAGCTTGGCTCCTTCGTCGCCGGACAATAGAGGGCCGACGGCGTATTAC
GTTCAGAGTCCGTCACGTGATTCTCACGATGGCGAGAAGACAACGACGTC
GTTTCACTCTACTCCTGTTATCAGTCCCATGGGTTCTCCTCCTCACTCTC
ACTCATCCGTCGGCCGTCACTCCCGTGATTCCTCTTCCTCCAGATTCTCC
GGCTCCCTCAAGCCTGGATCTCAGAAGATTTTACCCGACGCCGCCGGAGG
CGTCGGCGGCCGTCACCACCGCAAAGGGCAGAAGCCCTGGAAGGAATGTG
ATGTTATTTGAGGAAGAAGGACTACTTGAAGATGATAGATCCAGTAAATC
TCTTCCACGTCGTTGCTATGTCCTTGCTTTTTGTTGTTGGTTTCTTCGTC
CTTTTCTCCTTCTTTGCTCTCATCCTTTGGGGTGCTAGTCGACCTC
(SEQ ID NO: 8)

TABLE 14

| C2_At1g74970 | COS-II marker |
|---|---|
| Mapping experiments | |
| Map: | Tomato-EXPEN 2000 |
| Forward primer (5'-3'): | |
| TCATCATCAACTATCGTGATGCTAAG | (SEQ ID NO: 9) |
| Reverse primer (5'-3'): | |
| ACGCTTGCGAGCCTTCTTGAGAC | (SEQ ID NO: 10) |
| Temperature: | 55° C. |
| Mg$^{+2}$ concentration: | 1.5 mM |
| PCR Product Sizes | |
| LA716: | 1000 |
| LA925: | 1000 |
| Digested band sizes (using AluI) | |
| LA716: | 550 |
| LA925: | 850 |
| Mapped locations | | | |
| Map | Chromosome | Offset | Confidence |
| Tomato-EXPEN 2000 | 4 | 109.7 | I |

TABLE 15

CT128 RFLP marker

RFLP Information
Name: CT128
Insert size: 700
Vector: pBLUESC
Cutting Site: EcoR1
Drug Resistance: AMP Forward sequence
CTTTTTTTTTTTTCAACACAAACAAAATTTCATTATATTGTCAGGTAGC
ACACTACATCTTTACACTGTCATCAAACGACCAGAGACTTGAGAACGTTT
TAAGAGATTCATTTTCCGGGGACAAAGTTTGTGGCGAAAGCCCAGGCATT
GTTGTTTACGGGGTCTGCAAGGTGGTCAGCAAGGTTCTCCAATGGACCCT
TTCCGGTGACAATAGCTTGACAAAAGAATCCAAACATAGAGACATAGCA
AGTCTACCGTTCTTGATCTCCTTTACCTTGAGCTCAGCAAATGCCTCTGG
GTCTTCAGCAAGGCCTAATGGGTCGAAGCTGCCACCAGGGTAGAGTGGGT
CGACAACCTCACCAAGAGGTCCACCAGCAATACGGTATCCCTCAACAGCT
CCCATCAACACAACTTGGCAAGCCCAGATGGCCAAGATGCTTTGTGCATG
GACCAAGCTTGGGTTGCCCAAGTAGTCAA
(SEQ ID NO: 11)

Reverse sequence
CTGGTGATTACGGGTGGGATACCGCTGGACTTTCAGCAGACCCTGAAACT
TTTGCCAAGAACCGTGAACTTGAGGTGATCCACTGCAGATGGGCTATGCT
TGGTGCTCTTGGATGTGTCTTCCCTGAGCTCTTGGCCCGTAATGGTGTCA
AGTTCGGTGAGGCTGTGTGGTTCAAGGCCGGATCCCAGATCTTCAGTGAA
GGTGGACTTGACTACTTGGGCAACCCAAGCTTGGTCCATGCACAAAGCAT

TABLE 15-continued

CTTGGCCATCTGGGCTTGCCAAGTTGTGTTGATGGGAGCTGTTGAGGGAT
ACCGTATTGCTGGTGGGACCTCTTGGTGAGGTTGTCGACCCACTCTACCC
TGGTGGCAGCTTCGACCCATTAGGCCTTGCTGAAGACCCAGAGGCATTTG
CTGAGCTCAAGGTAAAGGAGATCAAGAACGGTAGACTTGCTATGTTCTCT
ATGTTTGGATTCTTTGTTCAAGCTATTGTCACCGGAAAGGGTCCA
(SEQ ID NO: 12)

TABLE 16

| TG599 | RFLP marker |
|---|---|
| RFLP Information | |
| Name: | TG599 |
| Insert size: | 700 |
| Vector: | pGEM4Z |
| Cutting Site: | PST1 |
| Drug Resistance: | AMP |

Forward sequence
(SEQ ID NO: 13)
TGCTTTGAGACAGATGTCTCTCATTAAGTGACTGAAGCTTTCTTCTAGTT
GGCTAGCATATTCATTTTCAGCATATAATCTGTATCATGA ACAAAATTGCGACAGTATTGAATTTTTATTGTTGAATAGTCTTTTTATTA
TCCCCGAAGTTGAGGGTGGAACTTACATTTTCTGTTGATC CTTGCTTGCTGTTTTTGTAAACAAAAAAGCGTCACCCATTATTTTTCTTT
TATTCTTTCTAGGTTGGGACTAAGATTTTTTGAAATGAGA AAGGTATTCGCTACCTTGAGGGCTGTGGTTGAAGTGATGGAGTATCTGAG
CAAAGATGCAGCTCCTGATGGTGTGGGAAGGCTTATAAAG GAGGAGGGAGTATTTCCTTTCATTTCTTTGTATTTCCGTGTGTGTATAGT
CCGGAACTGGTTCCCTACTTATGAATTCTTTCATGGTTTG

GTCAATTGAGAAGGATCAAGAAATCTGATGCTACTTTATCATGGGAACTT

Reverse sequence
(SEQ ID NO: 14)
GCTTGCATGCCTGCAGAGTGGTCATACAATAAAAGGTAAAAATCAACATT
CTTACCTCTGGAAAGAAACCAATAGCATTGGTCAATGATG CTGCCTCTAGAGGAACAATATTGTATGGTGCAAGTTCCCCTGATAAAGTA
GCATCAGATTTCTTGATCCTTCTCAACTGACCAAACCATG AAAGAATTCATAAGTAGGGAACCAGTTCCGGACTATACACACGGAAAT
ACAAAGAAATGAAAGGAAATACTACCTCCTCCTTTATAAG CCTTCCCACACCATCAGGAGCTGCATCTTTGCTCAGATACTCCATCACTT
CAACCACAGCCCTCAAGGTAGCGAATACCTTTCTCATTTC AAAAAATCTTAGTCCCAACCTAGAAAGAATAAAAGAAAAATAATGGGTGA
CGCTTTTTTGTTTACAAAAACAGCAAGCAAGGATCAACAG

AAATCTAAGTTCCACCCTCAACTTCGGGGATAATAAAAAGACTATTCAA
CAATAAAAATTCAATACTGTCGCAA

TABLE 17

| TG10 | RFLP marker |
|---|---|
| RFLP Information | |
| Name: | TG10 |
| Insert size: | 900 |
| Vector: | pUC |
| Cutting Site: | EcoR1/HindIII |
| Drug Resistance: | AMP |

Forward sequence
(SEQ ID NO: 15)
AACTCTGCTCTGCCAATAGTAGTCAGGCAGATCAAGATGCTCAAAATTTC
CTATTTGAATTGGAAGCATCAAGATGGTTCTTAGCATTTA TTTTAGAAAGACTAACCATATTTATCAAATAACCAGACTGAGACGCACACA
AAAGTTTCCCTCTATTATTTTTATAATGATGTGAAGATGC

TABLE 17-continued

TACATAATGAGTACACTTTGCCTTACTTTACTGCAGATGGACCTACCAGG
CCCAAACGGACATGTAGCTATGACAGAAGAGCAACCGCTA

TGAATGTCTCAAACTGTTGGCCTAGGCGATCAGCACAGATGATGAATCTG
GAAGTACATTCCAAGAAGGAAAGCTGGAGCGTGGGAACTA

ACCAGATGCAGGGGATGAATCCACACCTTTCAGTTGATCATCTGAAGGGA
AAACTAAGAATTTTCATGAGAAAATGACTGGCTATTTTCA

ACTTTG

Reverse sequence
(SEQ ID NO: 16)
TTCAATGCATTTAAGCTCAAAAAAACAAAGCTGTAGGAAGGAGCATATTA
GTAGCCTAACTCTGCTCTGCCAATAATAGTTAAGCAGATC AAGATGCTCAAAATTTTCTAATTGAATTGTTAGCATCAAGATGCTTCTTA
GCATTTATTTTAGAAAGATTAACCATATTATCAAATAACC AGACAGAGACGCACACAAAAGTTTCAATCTATTATTTTTATAATGATGTG
AAAATGCTACATAATGAGTACACTTTCCCTTACTTTACTG CAGATGGACCTACCAGGCCCAAACGGTCATGTAGTTATGACAGAAGAACA
ACAGTATGAATTTCTCAAACTGTTGGCCAAGGTGATCAGC AAAGATTATGAATTTGGAAGTACATTCCAAGAGGAAAGCTGGAGCATCGT
AACTAACCAGATGCAGGGGATGAATCCACACCTTTCAGTT GATCATCTGAAGGCAAAACTAAGAATTTTCATGAGAAAATACTGGTTATT
TTCAACTTTGTTGGCCAGACGAGGAGTCCAATGGGATAGA

AGGACTAACTCAATGACGTATG

TABLE 18

| TM2a | TM marker |
|---|---|

TM Information
Name:         TM2A
Old COS ID:   T0899

Sequence
(SEQ ID NO: 17)
CNAGCTCGANNNACCCTCACTAAAGGGAACAAAAGCTGGAGCTCCACCGC
GGTGGCGGCCGCTCTAGAACTAGTGGATCCCCCGGGCTGCAGGCCTCC
ATTGAAAAGGGAATCAAGTTTGCCAAAGAAAACTAAAAAAACAAAATTAT
GGTCTAGTTTTCTATAGTGACAGTTTTGGATCTTTTTGGGTCAATTGTTT
TTGTATCCTTTGCAAGTTTCTTGCAGCCGGAGGCTTAGATTTAGCTCTTT
TGATATTATACCCAACATTTCTACAAAATAATGTATGGCAAACTGGGGGC
CTATCCCATTTGCCTTAGTGTGGAGGTGTTATTCTCACATGAATCGTTTT
CCAATTATGGTTAGTAGCAGACAATTGATGCAAAATGAAGAAATGTTCAT
GACCAAAAAAAAAAAAAAAAAA

| Mapped locations | | | |
|---|---|---|---|
| Map | Chromosome | Offset | Confidence |
| Tomato-EXPEN 2000 (TM2A) | 9 | 50.5 | I |

TABLE 19

| TG551 | RFLP marker |
|---|---|

RFLP Information
Name:         TG551
Insert size:   950
Vector:       pGEM4Z
Cutting Site:  PST1
Drug Resistance: AMP

TABLE 19-continued

Forward sequence
(SEQ ID NO: 18)
AATGAAGTTCAGTTGATAAGCTAAATGGTGGAAATACTAATTTTAATTGA
CAGTAACTTTGCATTTCAAGGTCCATACCAAAACATTTGC TAACACCAGTTGCTTTGTCAACGAAAACCTTGGCACTCAAAACCCTACCA
AAAGGCTGAAATGCATTTGCAAGCTCTTGATCACCAAATT CTTGAGGAATATGGTAAATAAATAGATTAGCACCAGGTGGACCTGTAAAC
AGCAAAATCGTTTTTGATAAGTACAGGTTTATTTCTACAT GTTCAACTACCACTGCCAAGTACACTAGTTCAAGTGACATCTCCACCACT
TAATTGCATAAAGCTTTACCAACGACAAATATAACAAACT TGTGCAAGTAATTTGAGTTCCTGTCTATACAGTCCAGAATCTCCATATGC
TGCTCATCTCACAATGTTGGTTAAGGAAATTTGTCAAGTA

AAGTTCAA

Reverse sequence
(SEQ ID NO: 19)
CATCTTCAAGTGTCAGCTCAAGTACAGGGGGTCAGGTTGAAGGTTGTTGA
ACATTTATTTTGTGACCTTTTTAGCTCTAGAATTTCTGTA GCTAATCAAGTACAGTCCCATAACCTAGGGGCTGTTAGGGTTTTCTGCTG
AATGAGGCTGCTTGTCTTTATTTTGGTTAATTATTTTCTG GAAATTGTTCCTCGTCATAGAGAATAGAAGTAGAAGAAGAAGAAGATAGT
ATAATCTATTATATTTGTTTTTTACTTAATTTATAAAGAT TCCATAAATGCATGTGATCTTTGATCAATGATATCTTATACAAGTGTATC
ACTAGAATCTATTATATTTGGATTTACTTATTTTATATAG

GATTTCATAAACGCATGTGATC

TABLE 20

| T1405 COS Marker |
|---|

COS Information

Name: T1405
MIPS Category: 1.05.01
EST Information

T1405 was developed from the EST trace TPTAR86TH.
*Arabidopsis* orthology

At match: T1405 best matches against the *Arabidopsis* BAC AC009243.3.
At position: 1.1490000
At identities: 0.677
Genbank protein hits Best GenBank protein hit: AAF17692.1
Evalue: 1.5e−67
Identities: 0.677
Description "similar to beta-1,4-xylosidase dbj | BAA24107[*Arabidopsis thaliana*]"

| Mapped locations | | |
|---|---|---|
| Map | Chromosome | Offset |
| Tomato-EXPEN 2000 | 4 | 77.00 |

TABLE 21

| CT173 | RFLP marker |
|---|---|

RFLP Information
Name:         CT173
Insert size:   400
Vector:       pBLUESC

TABLE 21-continued

Cutting Site: EcoR1
Drug Resistance: AMP

Forward sequence
(SEQ ID NO: 20)
TTTTTTTTTTTAAAAATTCAAACTCCAATTATTTGCAGTATAAAACTACA
GATACAAATCCCAGTACATGGTTTGAGGCACGATAATAAG GTGCTGATGAAATCCAAGACATGAGTTCACAATACATTACTGACCAATAT
ATTTACAAAGATTAGGGTAATGGCAGTAAAATCGCTGATT ACAGACAACATTCTTGGGATATATTTCATCTTAAAGATTAGGATTAGTAG
TATGTGTGGCAGTCACAGTAGAGACCATGGCATCAACTCC

GCAGATATTGTGACCCCTGCAGATCTTGTAATATCCGTGTTCTCCCCAAG
TCTTTCCCCAA

Reverse sequence
(SEQ ID NO: 21)
TTGGGGAAAGACTTGGGGAGAACACGGATATTACAAGATCTGCAGGGGTC
ACAATATCTGCGGAGTTGATGCCATGGTCTCTACTGTGAC TGCCACACATACTACTAATCCTAATCTTTAAGATGAAATATATCCCAAGA
ATGTTGTCTGTAATCAGCGATTTTACTGCCATTACCCTAA TCTTTGTAAATATATTGGTCAGTAATGTATTGTGAACTCATGTCTTGGAT
TTCATCAGCACCTTATTATCGTGCCTCAAACCATGTACTG

GGATTTGTATCTGTAGTTTTATACTGCAAATAATTGGAGTTTGAATTTTT
AAAAAAAAAA

Tomato-EXPEN 2000 (*S. lycopersicum* LA925×*S. pennellii* LA716 type F2.2000)

TABLE 22

TG254                RFLP marker

RFLP Information
Name:                TG254
Insert size:         2200
Vector:              pGEM4Z
Cutting Site:        PST1
Drug Resistance:     AMP Forward sequence
(SEQ ID NO: 22)
CTAGTTGGATTGAAACAATTGGGAATATAGTGTAGGAAGACTTCGGGCA
ATTATCTGCTTTCTTCTATATCAAACTGGGTCTATTGAAG AATTACAAACTGGACCTTAAATCTTTTGCCAGTTTTTGTAAAATTGATAA
ACTTTTGATATTTTATTATGGAAATTCAAAATATATCTTA ATAGTAGCTTGTTAATTTATTTCAAGAGACCCTTTTCATTGTTCATAGTT
CATTATCATCCCCTTATCAGTAGTGCACCAAGGGTGTGAC CTAGTGGTCAATTAAGTATGAATCATGAGTCTTAGACAGAAACACTAGGT
GATTTTCTTCCATGTGTCCTAGCCTCTTAGGCTTGGTGGA TAGAGGAGGTATCCTGTCTTTCCCCTTTCCAGAAATTCATAGCATTATTT
TCTGTTCTTTATTGATAAATTATTCATTAGAACAGTTATT

AGAAATGTGAACTGGTTGAGGTAGGCG

Reverse sequence
(SEQ ID NO: 23)
CAGAACAGAGAACATGTAAAGTTGTTCAACTAATGAGCATATTTAGAAAA
ACTTAGTGGCTATCAATAGTTGGCAATATGAAAACTAAGA TAGTGTGGTCACCTGTTGATCAATTTCTTCTTCAATAGGCATCTTGTCAG
CTTCCTCTTGTAACAAGGCTTTCATTTGTGACTTGAGAAT ATATCCAGGAGGAAGTGCATGCCTGTAATGGCATTCTTTACCATTTGGAC
AGGCCCAGAACCAACCGTACTGCTTTTTCTCCACAGCATC CAAAAAGAATTTACATACCTGCATATAAACCAAATCATAAGCTTGATTTA
TGAAACGAGCACTGCATTCATGTTTGGCAATATTTGACTG

TABLE 22-continued

GAGGAGGAGTTTTAAAGGGGGAAATTAAGACTATAGACACATACACTAAA
TATGCATAAAACGCCAAAAGTACCCTGGTTTCCTATCCAG

TTAAGGCAACAGTAGCAGAAAATGAGTGTTGTAATGAGTCAAT

Tomato-EXHIR 1997 (*S. lycopersicum* TA209×*S. habrochaites* LA1777 type BC1, 1997)

TABLE 23

TG223                RFLP marker

RFLP Information
Name:                TG223
Insert size:         790
Vector:              pGEM4Z
Cutting Site:        PST1
Drug Resistance:     AMP Forward sequence
(SEQ ID NO: 24)
TATTCAAGAAAATATTGTGTAGTGTTCTCCAATATTCAACTATTTAAGTT
CAATGGATCTAGACACACAATATTATTAATTCTCGTCGCC GATGGGATGGTTGAGTGATTGAAGCATAGGAATAACATCCTGGAGATTCT
AGGTTTGGACTCCAGTTTGAACATAAGTGTGAGCCCATCT GCTTTATCTTACAAGTTCAATTCAAACTTGTGTGAGTGGGCCATAGTAGA
TCCATGCAAAATAGTGGTTATGACGCTATGGTGAGTTCAT GAGAAGAATTATTGTTCCTTAGGAACAGTGACAGGAAATTCAATGGTCAA
ATAACATCAAGAAGACTTTTTGGATTAGTTACTGAGTGAT GTTCAGAAGAGGGACTAAATATCTAACATGCCCCCTCAAGCTCCAGATGG
TAAAGCAACTTGAGTTTGAGTTACTAGAATTTAGTAACAT

AAAAAGGTTTTCCAT

Reverse sequence
(SEQ ID NO: 25)
TTTCCACACACACAAAAAAAACATCTTGAACACACTGTAATCCCCCTCTT
CATCAAATTCTCCTGTGTCAACAACTTCCTTAGCCAGT AACCACACAACTTCCCTCTTCTGAACATTACAAAGTCGCTGATCCAGAAA
GTCTTGTTCTTGATGCTATTTGACCATTGAATTTCCTGTC ACTATCCAACATGAATAGTGTTTGTAGGGAATAAATTGAAATCAGATTAC
AAGGATCCAAATATCCATCCCCAACAATGTACTGTTTATG CCCGAAGGTGAGGATAAAAAGATGGAAAACCTTTTTATGTTACTAAATTC
TAGTAACTCAAACTCAAGTTGCTTTACCATCTGGAGCTTG

AGGGGGCATGTTAGATATTTAGTCCCTCTTCTG

Tomato-EXHIR 1997 (*S. lycopersicum* TA209×*S. habrochaites* LA1777 type BC1, 1997)

TABLE 24

TG47                 RFLP marker

RFLP Information
Name:                TG47
Insert size:         1900
Vector:              pUG
Cutting Site:        EcoR1/BamH1
Drug Resistance:     AMP Forward sequence
(SEQ ID NO: 26)
TGCAGTTGAATTCGTCTTCTTAACACTATTCTCTTATGCTGTGCATCAAG
ACAACCACCCTCATTGGGCGGTCATTGCTTCTTCAGGCAT GACCCTACAGTTAGTACATTTGGTTTTACCAAATCTTCTTCTAAGGATAA
ATCTATTTGACTATGGTTCACTCTCTAAATCATAAGCTGA

TABLE 24-continued

```
AACAACATCAACATACCCCGTGTAAATCATAAGCTAAAACAAACTCTAGA
ATAGCCTTACCTCATCATTCCTAGGACCATAATTTATATCT

ATACTTAGTCAAAATCATCATAAAATTTACCTACAAGACCATTTAGATCT
CACCTGATTAAGATTTGTTGGTTACTCGTAATCCCTTGAA

CTAAGGTGTAACATCTTAACCCCTCCTTTTGAGTATTTATACCATCATAT
TTTGAAACTTCTCGTAGGTTCATATGTTTCTTTTGGTACT

TGTTAGTATAGCTTGGAGTGGGACCCAAGGGGCTCCAGTGAGTTCTAGAC
AAGAAAAACGAGATTTGAACATTGCAGATTTTATGTTTTC

TGGT

Reverse sequence
                                        (SEQ ID NO: 27)
CTTTGTTTGCTTGCAAGACAGAGATTTATACACGCTAATGCTATCTTTTT
GTGTCATTAACAGCTAGTTTGATTTGCTTGGTTAATACAG TTATGGTAGATAGAGAAGATAGTTTCAAAATAGAAAGAATGATGTAGACA
GCATTAATGAATCTTTCTCCTTACAATTGTACCTTTGACA AGGAATCCACCTTTTATAGGTAGTTTGGTGAGTTTGATGGAAGATTGTGG
TTGAATCTGGTTGAGTCATAGACACTACTTGTACATTCTT TTATGACACTGACTTGATGTTGTAAGAGTGAAATGTATAGACTTATCAAC
AAATAACAGAGTAGAAATAAAAGTAGGTTGAAGATAGCTT CTTGTTTGGTTCTAACTTGCTCCTTTGTTGACTGATATGATAACATTGTG
TCAATATAAGATGATTCAAAATGTTGCCTGAATTTTTATG

AAATTGATATTCATCGTCCAGTTTAGAGAGTTCT
```

Tomato-EXPEN 2000 (*S. lycopersicum* LA925×*S. pennellii* LA716 type F2.2000)

TABLE 25

```
TG393                        RFLP Marker

RFLP Information
Name:                        TG393
Insert size:                 1200
Vector:                      pGEM4Z
Cutting Site:                PST1
Drug Resistance:             AMP Forward sequence
                                        (SEQ ID NO: 28)
ACTGACTAAGCTGCTGGATTTGATTAGCCGAAGGAATTTACTTTTGGTTA
CATCTTGCTCCATCACCTTTGTCTTTATCTAGGTCAATCT TGTACCATAGATGCAAATAACACTATGAACAGATTAACAATGTCTTGAGG
AGGATTAGGCTGTCAACAGCCTGCATAATAACAGGAACAA CATTGGCGTTTGTTTGCATCAGTTACTGTGACTCTGATTAAAGGAGAAA
TGTGGCATCCTCTGCTTATACTGTCAGTGTGTATACTTGT CAGGTTAAGTTGGTTGCTATAATCTTTAATAATTCTTGATTTTGTGGTTG
TTTCTGAAGTAAATTGATATGTGGGCCTTTGAGCTGGAGG AGATGGTACTTTAGCTATTCACTAACAATCGTTTACCTTAAAAATGTTAT
TCTGTAAGTATCTAACCAAATTCTGATCAC Reverse sequence
                                        (SEQ ID NO: 29)
TGCAGACACCAAAGAAACAATTGGTTATATAAAAACAATCCACAATCAT
TCTCTATAGAAGTCACGCAAAGACACTACATAACCTCCAA GTGCAATGAAGAGGATGCAGAATAAGAAGCTCAGAACTTCCAAAAGAAA
GGTGACTGAAAATAAGTTTGCTGAAAAGGTACAAGGCAAG TTCTAATTCTCAACTAGCTTTAGGTATACACTAAAGAAAAGGAAAATAAA
TTCCAAACAGAAGTTTCCATCCTACCTAGTACATAAAAGA AAAAGGTAAAAAGGAACATATGGAAGTGTTCCCCTGTTACCTAAACTTTT
GGTGATAAACAGTAATCATGATTACCCCCACCTCACACAC
```

TABLE 25-continued

```
CACCACTACAGCACAAAAATTAGAAATGTTGTATGGACCATGATCAACCA
GCCAAGAATCCCAGAAGGAGAATAAAGGAGTTCTCTTAAT

CACAAGAGGAGAATATCATCTACT
```

Tomato-EXPEN 2000 (*S. lycopersicum* LA925×*S. pennellii* LA716 type F2.2000)

TABLE 26

```
CT19                         RFLP marker

RFLP Information
Name:                        CT19
Insert size:                 300
Vector:                      pCR1000
Cutting Site:                HindIII/EcoR1
Drug Resistance:             KN Forward sequence Reverse sequence
                                        (SEQ ID NO: 30)
GCCCCAAAACTCCTGCTGGATTTTACTGGATCTCCACTTGCTGCGGACAT
TGCTTGCCTCCGACAATCATCTTCCCAACTTCTTCCTTTT TGTCTTGAAATTAATCCCTTGTACCCATTGCTGCTTCTAAATGACCTCCT
GCATCCCGGCGGATCCACTAGGTCTAAAGCTGCCGCCCCC

GC
```

Tomato-EXPEN 2000 (*S. lycopersicum* LA925×*S. pennellii* LA716 type F2.2000)

TABLE 27

```
TG68                         RFLP marker

RFLP Information
Name:                        TG68
Insert size:                 1900
Vector:                      pUC
Cutting Site:                EcoR1
Drug Resistance:             AMP Forward sequence
                                        (SEQ ID NO: 31)
GGATTTTGATGAACTTGTATCTGTGCTTCTAGCTCCACCTAGGATGAGTT
TGGATTTGTACGATTAACAAATGTTTGAGCTGAAAGAATT AAATTTGATTACACCTGCCTTTACATATTTTTGTTGCGTAAGGATTTTCT
ATGAAGAATATATATGTATGTATGTGTAAAGGATGCACTA AGCATCTCGCATTTTGATAAAGAAATGAACTTTGGGCTTAACTCAACTCC
AAAAGTTAGCTCATGAAGTGAGGATATCGCGTAAGACCGT ATAAGGAGACCTAGAACCCATCCCACAACAATGTGTGACTCCAACACATT
CACGCAAGTTCTGGGGAAGGGTTGCACTCGTAAGGGTTGT GATGTAGGCAGCCATAATTGTGTGTACCCATTCGTTAGAAAACTACACTG
TGCAAGTGGAGTTAAATTGTATCTTTTTTGGTTTTGTGTG

AGTTGTTCAATCCCCTTGACATGAAAAAAAAOAAGCAAAATTCAAGTATAA
TGGTAAAAGGGGATTCAAAAT

Reverse sequence
                                        (SEQ ID NO: 32)
TTGGGTCAGCCATAGTACTTCGTGATATATCTCTGACAGAAGATATCTGC
TCAAGACCATGAACAATACGGAGACATAAGAAGGAAAGAA GTTCAGTGCAGCACAAAATTTTAATAAGTTAACTTAAAGGGGGATAAGAG
GCAAAACCAATATAAAAGTTTGGACAGACAAATTTTAATT
```

TABLE 27-continued

```
AGTATCAAAGAGTGAATGATGCTAAAGAAGAGATGCTTAAATATCTGATA
CTATAAAGTAAGCCATGACTAATTGGTAATTATGAATGG

CATATGATACGACTATCAGTTTTGACTGTTGTCTACAATAATGATTTCAG
AAACATATGATATATTTCAAATAGAATTGAATAACAACAC

TTGTTCAAATACCTAGCTCTCGGAGGCAGATCCAGAATTTTAGAAAGTGG
GTGCAGTAAATCACAAGAGTACACCTCTGCTAGAATGGGT

GTGTACTGTAACAAAACCTGTTTTGATATGCATAT
```

Tomato-EXPEN 2000 (*S. lycopersicum* LA925×*S. pennellii* LA716 type F2.2000)

TABLE 28

| TG565 | RFLP marker |
|---|---|
| RFLP Information | |
| Name: | TG565 |
| Insert size: | 1700 |
| Vector: | pGEM4Z |
| Cutting Site: | PST1 |
| Drug Resistance: | AMP |

Forward sequence
(SEQ ID NO: 33)
```
ACTAGCATCTCTTGGAGGATGCTGAGGTGTCAAGTGGTGTTGACCACTCG
TTACCACTGATTCACAGCTGGTGTCTTTCGAAGCAAGCTT CGTCTGCAAAACAAGAATCACACTTTAATCCTCTGTTACCTAAAAACAAT
AGTTGTTTGATGTAATGAAAGAAGAATTTTCACTTCAATG ATGGAAAGAAAATCTTACAGTTTGAGTTTGCTTGCGAAAGTAGCCATTTT
CATACACCAGTTGAGAAACTTGCTTCTGCAATCTATCATT CTCTTCCATTAATAGCTTGTTCATTGCTGACAGCTTCCTATTCACACCCT
GAAGCCTTGATGACTCTTTCCTCTGTTTTTCCCTACATCT ATACAACTCAAAGAAACAATCAATTATACTTCAAATTAATTGGGGTCGCT
AAAAATGAATCCTTTAGACTAACAACATCCCACAAGTCCT

TACCCCTACCTCGCAGAGGTAGAGA
```

Reverse sequence
(SEQ ID NO: 34)
```
TCAGCAAAATGTCACACAGAGAGTACAGTAGTAGAGCACAGTAGAGTAGG
GAGAAGTTGCCTCAAAAGAGGAAAAGAAAAGGTAACGAAC CACACATTTGACAGCTCAAAACCACTTTACCAATCCAAACAAAAAATCAT
CACATTATCCCTCCCTTCTCTCCTTTCTCTATTACTCTCA TTTTCCCCAAGTTTCAGGTACCTTTTTCCTAACATAATCCGCCCATAGTG
TTCATCATTCAAGATCTGTCCTTTTGAGGAGACTTCATTC CTTACTATGGTCTTCTTTTTTTGATGATTTCTTATGTGAGATGTTGAAAA
CTGGAAAGAAGTGATAAAGATAGGAGGTTTGGTTTCTGGG

GTTTGTTTATTTTGCTTTACAAGGGTTAAAGATTGGATCTTTTTTAGTTT
```

```
TGGTAGATACCCATGTCTAATCTTGTTTCAGAATTCAAAA

GGTTGGTACTTTACTGTTTTGCAAGTGGATGACAGAGGAG
```

Tomato-EXPEN 2000 (*S. lycopersicum* LA925×*S. pennellii* LA716 type F2.2000)

TABLE 29

| TG296 | RFLP marker |
|---|---|
| RFLP Information | |
| Name: | TG296 |
| Insert size: | 1100 |
| Vector: | pGEM4Z |
| Cutting Site: | PST1 |
| Drug Resistance: | AMP |

Forward sequence
(SEQ ID NO: 35)
```
TTAGGTTTTTGTGTGGTTCAACGTTTTTGGTTTTGATTTTTATGTGTTTT
CTTAGTTCCTTGCTTCACCATTTTGATGGTATTTTGAGTT TTTGATGTTCTGTCGGCATAAAGTAGTGATTTTTCAGACAGTTTGGTATT
ATGGAGTATGTTTCTTTGCTCTTCTCTAATTTGGATTGGT TCTGATTTGTATATGCTTGTTTTAGTTTCGATGGTTTTTGAGTTTTTGAT
GATTCATTGGCACAAAGTAGTGATTTTTCAGACTGTTGGG TTTTGTGGGGTTCCCGTGCTTGCTCTTCACTAATTTGGATTGGTTCTGAT
TTGTATATGTTTTAGTTTTGATGGTTTTTGAGTTTTTGAT GATTCATCGGCACAAAGTAGTGATCTTTCAGACAGTTGGGTTTTGTGGGG
TTCACGTGCTTATTCTTCACTATTCTCGGTTGGTTTGATT

TGTAGGTCCGTTTTAGCAT
```

Reverse sequence
(SEQ ID NO: 36)
```
AGAATATAACAAAAAAGCAGATAAATCAGTTAATTATGCCTCAATCTCAA
CAAGTGAATAACAAATCCTATCAGAAGATATAGTAGACGA TAAACAGTGAAGGTAGAAGCCTAACTCTATGACATTATCTTGAGACCCAA
AACACTTCATCAAAGACTCAAAAGAAATAATTTGTTCACC AAGTACTATTAACTAATTATCAAAACTAGAATTCTCAAAATAAAAAATAA
CAAATCTTATCAGTCACATGGACATTCATTAAACATCATG AAGAAGACAACAAGGGAAGGTCAAAACTGGACTCCATGGCACATAAGATA
ATAACAAAAGGTAGTTTAAGGCCTAAAACACTTCAAAAAT AAAATTTATTCACCAGATATCAATAATATTATCTGTTCTTCCTTCATTCA
TGAGGGGCATGCACAAGAGACAATATACATCATTTCTCCT

TTTACTTTTTCTTTCCTGAGGAAGTAAAAGGAGCAGAAAGCAGATAGAAA
GA
```

Tomato-EXPEN 2000 (*S. lycopersicum* LA925×*S. pennellii* LA716 type F2.2000)

TABLE 30

Primer sequences, lengths of PCR products and enzymes revealing a polymorphism for CAPS/SCAR markers.

| Marker name | Chromosome | Primer sequence (5'-3') | Observed PRC product length (bp) | Annealing Tm (° C.) | Marker Type | Enzyme |
|---|---|---|---|---|---|---|
| TG224 | 1 | GTATACTCAACAGAGCTTCAGAC GTGTAGATACCTGCACTCTCAG (SEQ ID NO: 37) | 500 | 55 | CAPS | HaeIII |

TABLE 30-continued

Primer sequences, lengths of PCR products and enzymes revealing a polymorphism for CAPS/SCAR markers.

| Marker name | Chromosome | Primer sequence (5'-3') | Observed PRC product length (bp) | Annealing Tm (° C.) | Marker Type | Enzyme |
|---|---|---|---|---|---|---|
| TG59 | 1 | AACTCTACGCTGCACTGCTG CTGAAGCTCACCTTGAGGTG (SEQ ID NO: 38) | 300 | 55 | CAPS | HpaII |
| TG460 | 1 | CGAAATGTGACTATTCCAGAG GTAATTTGCACTTCTTGCCT (SEQ ID NO: 39) | 400 | 55 | CAPS | AluI |
| TG145 | 2 | TTCATTTGCTGGACAGGCAGTC TGTCATCAAACGACCAGAGAC (SEQ ID NO: 40) | 850 | 55 | CAPS | HpyCH4IV |
| C2_At4g30930 | 2 | ATCATACCTTCTCTCTCCAAACCC TCGCCATTGCTCACTTTAAACTG (SEQ ID NO: 41) | 700 | 55 | CAPS | BseDI |
| C2_At5g64670 | 2 | TGATAAATGCTGGGAAGATTGACTC ATCAACCTGGCTCCATCTTCTATTTG (SEQ ID NO: 42) | 200 | 55 | SCAR | |
| TG337 | 2 | TCCACAGTTATTGCTTCTTGTTTC GGGTGTGTCTGTTTGACAGC (SEQ ID NO: 43) | 450 | 57 | CAPS | Mn1I |
| TG91 | 2 | TGCAGAGCTGTAATATTTAGAC CGGTCTCAGTTGCAACTCAA (SEQ ID NO: 44) | 400 | 55 | CAPS | ApoI |
| TG40 | 3 | GCGAGCTCGAATTCAATTCCAAC CGGGATTTTAGTTTTTCCGATCC (SEQ ID NO: 45) | 450 | 55 | CAPS | HpyCH4IV |
| TG56 | 3 | TTTGTACCATGATTGTCCGATC GGCATTCATCATTCAACATGC (SEQ ID NO: 46) | 380 | 55 | CAPS | HpaIII |
| TG585 | 3 | TGGAAAGCCAGACACACAGA CAGGGGTATCAGTAGGCAGTG (SEQ ID NO: 47) | 580 | 55 | CAPS | HinfI |
| T1388 | 3 | GCGATTTGGCTATCTGGGTA AACCGAAAGGCTTTTCCAAG (SEQ ID NO: 48) | 1000 | 55 | CAPS | Hin1II |
| T0753 | 3 | TGGTGCAACAAATCCCGAGC | 1500 | 55 | SCAR | |

TABLE 30-continued

Primer sequences, lengths of PCR products and enzymes revealing a polymorphism for CAPS/SCAR markers.

| Marker name | Chromosome | Primer sequence (5'-3') | Observed PRC product length (bp) | Annealing Tm (° C.) | Marker Type | Enzyme |
|---|---|---|---|---|---|---|
| | | AGTTATCATAATGGCT AGCTTG (SEQ ID NO: 49) | | | | |
| C2_At5 g60160 | 3 | ACACAATGCTAATCAA CGTTATGC TCATCCACCGCCCACA TTTC (SEQ ID NO: 50) | 500 | 55 | CAPS | Hin1II |
| TG599 | 3 | GCATGCCTGCAGAGTG GTC ATTCGCTACCTTGAGG GCTG (SEQ ID NO: 51) | 350 | 65 | CAPS | DdeI |
| C2_At5 g49970 | 3 | AATTGGCAGGCTTGAG TGTTGC TCCCACCATTGTTACC AGGACCAC (SEQ ID NO: 52) | 850 | 55 | CAPS | HpyCH4IV |
| TG42 | 3 | TTCCTCACTGCTTGGA CCAGC TAGAACTTGGCATCCC TTGAAG (SEQ ID NO: 53) | 560 | 55 | CAPS | Mn1I |
| TG134 | 3 | CTACACAATTGTCACA GAAGTG GAGATCATTGGTATAC AGCTG (SEQ ID NO: 54) | 500 | 55 | SCAR | |
| C2_At1 g61620 | 3 | ATGCATTCTAGAATGC CTTTTGTC TCCCTGGCTTTCTGCA GCATC (SEQ ID NO: 55) | 1350 | 5 | CAPS | HaeIII |
| TG549 | 3 | ATGGAGAGAAGCTGGA ACAC TTCTTAGAGCCCACCA GCAC (SEQ ID NO: 56) | 400 | 55 | SCAR | MseI |
| CT229 | 4 | ATGGGCTGGGATCGTA GTAAA AAGCTTGCGATTCCCA TAACA (SEQ ID NO: 57) | 336 | 55 | CAPS | MwoI |
| T1068 | 4 | CAAAGCAATGGGCAAT GGT ACACAGCAGTTTCAGT AGGAC (SEQ ID NO: 58) | 304 | 55 | CAPS | HincII |
| TG272 | 4 | GATTTGCCCCCTCTA CCA ACATCTTTTCCTTCCC TCTGC (SEQ ID NO: 59) | 352 | 55 | CAPS | Mn1I |
| TG264 | 4 | GGAACAGGTCAGGACA GCAT TGGCTAACTGACGAAG ACGA (SEQ ID NO: 60) | 520 | 55 | CAPS | HaeII |

TABLE 30-continued

Primer sequences, lengths of PCR products and enzymes revealing a polymorphism for CAPS/SCAR markers.

| Marker name | Chromosome | Primer sequence (5'-3') | Observed PRC product length (bp) | Annealing Tm (° C.) | Marker Type | Enzyme |
|---|---|---|---|---|---|---|
| TG62 | 4 | CATGCCTAGTTGCAGT GTCC TTCAGCAGCAAGCAAA GATG (SEQ ID NO: 61) | 410 | 63 | CAPS | DdeI |
| T1405 | 4 | CACCAACAACTAGCCC TTGA AAGCAATTCCTCCAGC TTCA (SEQ ID NO: 62) | 535 | 55 | CAPS | BsaJI |
| CT50 | 4 | GACGGCGTATTACGTT CAGA CTAGCACCCCAAAGGA TGAG (SEQ ID NO: 63) | 390 | 55 | CAPS | DdeI |
| TG441 | 5 | TGTCAGCATAGGCTTT TCCA CGGTCGGGAAAAATGA CA (SEQ ID NO: 64) | 550 | 55 | CAPS | RsaI |
| CD31 | 5 | ATCTCGGGATCATGGT TGAC ATNNCCANAGAAATTC CAAA (SEQ ID NO: 65) | 501 | 55 | CAPS | HinfI |
| TG318 | 5 | CAAGCCATAGAAATTG CCGTA TGCTCTCTCTGTGATG GAAGC (SEQ ID NO: 66) | 450 | 55 | SCAR | |
| TG358 | 5 | CAACTTTTCCAGGTTC ATTTTCTC ACACCTACATGCTACT AAGGGGTC (SEQ ID NO: 67) | 700 | 55 | CAPS | DdeI |
| TG60 | 5 | TTGGCTGAAGTGAAGA AAAGTA AAGGGCATTGTAATAT CTGTCC (SEQ ID NO: 68) | 400 | 55 | CAPS | HpyCH4IV |
| CT138 | 5 | ACCAGCCCCGGAAGAT TTTA GCGGTCAACTTCAGCA ACTAT (SEQ ID NO: 69) | 364 | 55 | CAPS | RsaI |
| TG183 | 7 | CTACTTGTCTGCCAAG GATTAC CGTGCCGTTCAAGAAG AGTG (SEQ ID NO: 70) | 1200 | 55 | SCAR | |
| CT114 | 7 | ATTGAAGAATGGCGGT GAAG ATGCCAACTTCTTGGC AAAC (SEQ ID NO: 71) | 1125 | 55 | CAPS | DdeI |
| TG254 | 9 | TTGGGAATATAGTGTA GGAAG | 380 | 55 | CAPS | FokI |

TABLE 30-continued

Primer sequences, lengths of PCR products and enzymes revealing a polymorphism for CAPS/SCAR markers.

| Marker name | Chromosome | Primer sequence (5'-3') | Observed PRC product length (bp) | Annealing Tm (° C.) | Marker Type | Enzyme |
|---|---|---|---|---|---|---|
| | | CTGGAAAGGGGAAAGAC (SEQ ID NO: 72) | | | | |
| TG223 | 9 | CAAGAAAATATTGTGTAGTGTTCTCCA TCCCCCTCTTCATCAAATTC (SEQ ID NO: 73) | 700 | 55 | CAPS | MnlI |
| TG10 | 9 | ATGATATCCACACCCCTGGA ATGCCTCGAAATTCAAATGC (SEQ ID NO: 74) | 587 | 55 | CAPS | AluI |
| Tm2a | 9 | AGCGTCACTCCATACTTGGAATAA AGCGTCACTCAAAATGTACCCAAA (SEQ ID NO: 75) | 1600 | 53 | CAPS | ACCI |
| U38666 | 9 | AGCTGCCGTGTCCTGTATCA ACTCATGTTCACGCCACTTTCTTA (SEQ ID NO: 76) | 400 | 55 | CAPS | HinfI |
| CT203 | 10 | TAGAATATGGGAAGCGAAATG GAGAGGAAGCGTAATAGG (SEQ ID NO: 77) | 400 | 55 | CAPS | HaeIII |
| CT240 | 10 | ATCCCAAGTACCCTCGCATTAGT AGCCTTCTTTGTCCCATCAG (SEQ ID NO: 78) | 850 | 55 | CAPS | HaeIII |
| TG296 | 12 | TGTTCTGTCGGCATAAAGT TGCTAAAACGGACCTACAA (SEQ ID NO: 79) | 373 | 55 | CAPS | HpyCH4IV |

TABLE 31

Size table of alleles found at polymorphisms of Table 30., when cut with the indicated enzyme(s).

| Marker name | Chrom. | Observed PCR product length | Alleles with discriminating capacity (estimated size digested [bp]) | |
|---|---|---|---|---|
| | | | homozygous SL* | homozygous SH* |
| CT229 | 4 | 400 | 300 + 100 | 400 |
| T1068 | 4 | | 130 + 670 | 900 |
| TG272 | 4 | | 200 | 250 |
| TG264 | 4 | | 450 | 160 + 280 |
| TG62 | 4 | | 90 + 350 | 90 + 130 + 210 |
| T1405 | 4 | | 180 + 370 | 100 + 180 + 310 |
| CT50 | 4 | | 190 + 210 | 400 + 410 |
| TG254 | 9 | | 350 | 300 |
| TG223 | 9 | | 200 + 360 | 250 + 260 |
| TG10 | 9 | | 220 + 367 | 520 |
| TM2a | 9 | 1050 | 425 + 625 | 1050 |
| U38666 | 9 | | 180 + 400 | 200 + 250 |
| TG296 | 12 | | 340 | 290 |

*SL = *Solanum lycopersicum*, SH = *Solanum habrochaites*. In heterozygous plants digested products of both SL and SH are found. Both in Table 30 and Table 31 the observed PCR product length is estimated from agarose gel bands.

REFERENCES

Ausubel FM, Brent R, Kingston RE, Moore DD, Seidman JG, Smith JA, Struhl K. (1995). "Current Protocols in Molecular Biology", 4th edition, John Wiley and Sons Inc., New York, N.Y.

Bai YL, Huang CC, van der Hulst R, Meijer Dekens F, Bonnema G, Lindhout P (2003) QTLs for tomato powdery mildew resistance (*Oidium lycopersici*) in *Lycopersicon parviflorum* G1.1601 co-localize with two qualitative powdery mildew resistance genes. *Mol. plant microbe interactions* 16:169-176.

Benito EP, ten Have A, van't Klooster JW, van Kan JAL (1998) Fungal and plant gene expression during synchronized infection of tomato leaves by *Botrytis cinerea*. *Eur. J. Plant Pathol.* 104:207-220.

Bernacchi D, Tanksley SD (1997) An interspecific backcross of *Lycopersicon lycopersicum×L. hirsutum*: Linkage analysis and a QTL study of sexual compatibility factors and floral traits. *Genetics* 147:861-877.

Brugmans B, van der Hulst RGM, Visser RGF, Lindhout P, van Eck HJ (2003) A new and versatile method for the successful conversion of AFLP (TM) markers into simple single locus markers. *Nucleic acids research* 31: Nil_9-Nil_17

Canady MA, Meglic V, Chetelat RT (2005) A library of *Solanum lycopersicoides* introgression lines in cultivated tomato. *Genome* 48: 685-697

Christou P, Murphy JE, and Swain WF (1987) Stable transformation of soybean by electroporation and root formation from transformed callus. *Proc. Natl. Acad. Sci. USA* 84:3962-3966.

Churchill GA, Doerge RW (1994) Empirical threshold values for Quantitative trait mapping. *Genetics* 138: 963-971.

Deshayes A, Herrera-Estrella L, Caboche M (1985) Liposome-mediated transformation of tobacco mesophyll protoplasts by an *Escherichia coli* plasmid. *EMBO J.* 4:2731-2737.

D'Halluin K, Bonne E, Bossut M, De Beuckeleer M, Leemans J (1992) *Plant. Cell* 4:1495-1505.

Dik AJ, Koning G, Kohl J (1999) Evaluation of microbial antagonists for biological control of *Botrytis cinerea* stem infection in cucumber and tomato. *Eur. J. Plant Pathol.* 105:115-122.

Doganlar S, Frary A, Ku HM and Tanksley SD (2002) Mapping Quantitative Trait Loci in Inbred Backcross Lines of *Lycopersicon pimpinellifolium* (LA1589). *Genome* 45:1189-1202.

Draper J, Davey MR, Freeman JP, Cocking EC and Cox BJ (1982) Ti plasmid homologous sequences present in tissues from *Agrobacterium* plasmid-transformed *Petunia* protoplasts. *Plant and Cell Physiol.* 23:451-458.

Dunnett CW (1955) A multiple comparison procedure for comparing several treatments with a control. *Journal of the American Statistical Association* 50: 1096-1121.

Eckstein F (ed) (1991) *Oligonucleotides and Analogues, A Practical Approach.* Oxford Univ. Press, NY 1991.

Eduardo I, Arus P, Monforte AJ (2005) Development of a genomic library of near isogenic lines (NILs) in melon (*Cucumis melo* L.) from the exotic accession P1161375. *Theor Appl Genet* 112: 139-148

Egashira H, Kuwashima A, Ishiguro H, Fukushima K, Kaya T, Imanishi S (2000) Screening of wild accessions resistant to gray mold (*Botrytis cinerea* Pers.) in *Lycopersicon*. *Acta physiologiae plantarum* 22:324-326.

Eshed Y, Zamir D (1994) A genomic library of *Lycopersicon pennellii* in *S. lycopersicum*: a tool for fine mapping of genes. Euphytica. Dordrecht: Kluwer Academic Publishers. 1994 79: 175-179

Eshed Y, Zamir D (1995) An introgression line population of *Lycopersicon pennellii* in the cultivated tomato enables the identification and fine mapping of yield-associated QTL. Genetics. Bethesda, Md.: Genetics Society of America. November 1995 141: 1147-1162

Foolad MR, Zhang LP, Khan AA, Nino Liu D, Liln GY (2002) Identification of QTLs for early blight (*Alternaria solani*) resistance in tomato using backcross populations of a *Lycopersicon lycopersicum×L. hirsutum* cross. *Theor. Appl. Genetics* 104:945-958.

Frary A, Doganlar S, Frampton A, Fulton T, Uhlig J, Yates H, Tanksley S (2003) Fine mapping of quantitative trait loci for improved fruit characteristics from *Lycopersicon chmielewskii* chromosome 1. *Genome* 46: 235-243

Frary A, Nesbitt TC, Grandillo S, Knaap Evd, Cong B, Liu J, Meller J, Elber R, Alpert KB, Tanksley SD (2000) fw2.2: a quantitative trait locus key to the evolution of tomato fruit size. *Science Washington.* 2000; 289: 85-88.

Fridman E, Carrari F, Liu YS, Fernie AR, Zamir D (2004) Zooming in on a quantitative trait for tomato yield using interspecific introgressions. *Science* 305: 1786-1789.

Fridman E, Pleban T, Zamir D (2000) A recombination hotspot delimits a wild-species quantitative trait locus for tomato sugar content to 484 bp within an invertase gene. *Proc Natl Acad Sci USA.* Washington, D.C.: National Academy of Sciences. Apr. 25, 2000 97: 4718-4723.

Fulton T, van der Hoeven R, Eannetta N, Tanksley S (2002). Identification, Analysis and Utilization of a Conserved Ortholog Set (COS) Markers for Comparative Genomics in Higher Plants. *The Plant Cell* 14(7): 1457-1467.

Godoy G, Steadman JR, Dickman MB, Dam R (1990) Use of mutants to demonstrate the role of oxalic acid in pathogenicity of *Sclerotinia sclerotiorum* on *Phaseolus vulgaris*. *Physiological Molecular Plant Pathology* 37, 179-191.

Grandillo S, Tanksley SD (1996) QTL analysis of horticultural traits differentiating the cultivated tomato from the closely related species *Lycopersicon pimpinellifolium*. *Theor Appl Genet* 92: 935-951.

Gruber MY, Crosby WL (1993) Vectors for Plant Transformation. In: Glick BR and Thompson JE (Eds.) *Methods in Plant Molecular Biology & Biotechnology*, CRC Press, pp. 89-119.

Haanstra JPW, Wye C, Verbakel H, Meijer Dekens F, van den Berg P, Odinot P, van Heusden AW, Tanksley S, Lindhout P, Peleman J (1999) An integrated high density RFLP-AFLP map of tomato based on two *Lycopersicon lycopersicum× L. pennellii* $F_2$ populations. *Theor. Appl. Genetics* 99: 254-271.

Hain R, Stabel P, Czernilofsky AP, Steinbliss HH, Herrera-Estrella L, Schell J (1985) Uptake, integration, expression and genetic transmission of a selectable chimaeric gene to plant protoplasts. *Mol. Gen. Genet.* 199:161-168.

Horsch RB, Fry JE, Hoffman NL, Eichholts D, Rogers SG, Fraley RT (1985) A simple method for transferring genes into plants. *Science* 227:1229-1231.

Jansen RC (1993) Interval Mapping of Multiple Quantitative Trait Loci. *Genetics* 135:205-211.

Jansen RC (1994) Controlling the Type I and Type II Errors in Mapping Quantitative Trait Loci. *Genetics* 138:871-881.

Jeuken MJW, Lindhout P (2004) The development of lettuce backcross inbred lines (BILs) for exploitation of the *Lactuca saligna* (wild lettuce) germplasm. *Theor Appl Genet* 109: 394-401

Kado CI (1991) Molecular mechanisms of crown gall tumorigenesis. *Crit. Rev. Plant Sci.* 10:1-32.

Klein TM, Gradziel T, Fromm ME, Sanford JC (1988). Factors influencing gene delivery into *zea mays* cells by high velocity microprojectiles. *Biotechnology* 6:559-563.

Klein TM, Arentzen R, Lewis PA, and Fitzpatrick-McElligott S (1992) Transformation of microbes, plants and animals by particle bombardment. *Bio/Technology* 10:286-291.

Kosambi DD (1944) The estimation of map distances from recombination values. *Ann. Eugen.* 12:172-175.

Ku HM, Liu J, Doganlar S, Tanksley SD (2001) Exploitation of *Arabidopsis*-tomato synteny to construct a high-resolution map of the ovate-containing region in tomato chromosome 2. Genome. Ottawa, Ontario, Canada: National Research Council of Canada. June 2001 44: 470-475

Laursen CM, Krzyzek RA, Flick CE, Anderson PC, Spencer TM (1994) Production of fertile transgenic maize by electroporation of suspension culture cells. *Plant Mol Biol.* 24(1):51-61.

Lin SY, Sasaki T, Yano M (1998) Mapping quantitative trait loci controlling seed dormancy and heading date in rice, *Oryza sativa* L., using backcross inbred lines. *Theor Appl Genet* 96: 997-1003.

Miki B L, Fobert P F, Charest P J, Iyer V N (1993) Procedures for Introducing Foreign DNA into Plants. In: Glick B R and Thompson J E (Eds.) *Methods in Plant Molecular Biology & Biotechnology*, CRC Press, pp. 67-88.

Moloney M M, Walker J M, Sharma K K (1989) High efficiency transformation of *Brassica napus* using *Agrobacterium* vectors. *Plant Cell Reports* 8:238-242.

Monforte A J, Friedman E, Zamir D, Tanksley S D (2001) Comparison of a set of allelic QTL-NILs for chromosome 4 of tomato: deductions about natural variation and implications for germplasm utilization. *Theor appl genet.* Berlin; Springer Verlag. March 2001 102: 572-590

Monforte A J, Tanksley S D (2000a) Development of a set of near isogenic and backcross recombinant inbred lines containing most of the *Lycopersicon hirsutum* genome in a *L. esculentum* genetic background: A tool for gene mapping and gene discovery. *Genome* 43: 803-813

Monforte A J, Tanksley S D (2000b) Fine mapping of a quantitative trait locus (QTL) from *Lycopersicon hirsutum* chromosome 1 affecting fruit characteristics and agronomic traits: breaking linkage among QTLs affecting different traits and dissection of heterosis for yield. *Theor appl genet.* Berlin; Springer Verlag. February 2000 100: 471-479

Myburg A A, Remington D L, O'Malley D M, Sederoff R R, Whetten R W (2001) High-throughput AFLP analysis using infrared dye-labeled primers and an automated DNA sequencer. *Biotechniques* 30: 348-357.

Nesbitt T C, Tanksley S D (2001) fw2.2 directly affects the size of developing tomato fruit, with secondary effects on fruit number and photosynthate distribution. *Plant Physiol.* 127: 575-583.

Nicot P C, Moretti A, Romiti C, Bardin M, Caranta C, Ferriere H (2002) Differences in susceptibility of pruning wounds and leaves to infection by *Botrytis cinerea* among wild tomato accessions. *TGC Report* 52: 24-26.

Paterson A H (ed.) (1996) Genome Mapping in Plants, Academic Press Inc San Diego, Calif., USA.

Pestsova E G, Borner A, Roder M S (2001) Development of a set of *Triticum aestivum*-Aegilops tauschii introgression lines. *Hereditas* 135: 139-143.

Phillips R L, Somers D A, Hibberd K A. 1988. Cell/tissue culture and in vitro manipulation. In: G. F. Sprague & J. W. Dudley, eds. *Corn and corn improvement*, 3rd ed., p. 345-387. Madison, Wis., USA, American Society of Agronomy.

Pierik R L M (1999) In vitro Culture of Higher Plants, 4th edition, 360 pages, ISBN: 0-7923-5267-X.

Prins T W, Tudzynski P, von Tiedemann A, Tudzynski B, ten Have A, Hansen M E, Tenberge K, van Kan J A L (2000) Infection strategies of *Botrytis cinerea* and related necrotrophic pathogens. In "Fungal Pathology" (J. Kronstad, editor). Kluwer Academic Publishers, pp. 33-64.

Ramsay L D, Jennings D E, Bohuon E J R, Arthur A E, Lydiate D J, Kearsey M J, Marshall D F (1996) The construction of a substitution library of recombinant backcross lines in *Brassica oleracea* for the precision mapping of quantitative trait loci. *Genome* 39: 558-567

Roupe van der Voort J N A M, van Zandvoort P, van Eck H J, Folkertsma R T, Hutten R C B, Draaistra J, Gommers F J, Jacobsen E, Helder J, Bakker J (1997) Use of allele specificity of comigrating AFLP markers to align genetic maps from different potato genotypes. *Mol. Gen Genetics* 255: 438-447.

Rousseaux M C, Jones C M, Adams D, Chetelat R, Bennett A, Powell A (2005) QTL analysis of fruit antioxidants in tomato using *Lycopersicon pennellii* introgression lines. *Theor Appl Genet* 111: 1396-1408

Sambrook J, and Russell D W (2001). Molecular Cloning: A Laboratory Manual. New York, N.Y., USA., Cold Spring Harbor Laboratory Press.

Sanford J C, Klein T M, Wolf E D, Allen N (1987). Delivery of substances into cells and tissues using a particle bombardment process. *J. Particulate Sci. Technol.* 5:27-37.

Sanford J C (1988) The biolistic process. *Trends in Biotechnology* 6:299-302.

Sanford J C (1990) Biolistic plant transformation. *Physiologica Plantarum* 79: 206-209.

Sanford J C, Smith F D, and Russell J A (1993) Optimizing the biolistic process for different biological applications. *Methods in Enzymology* 217:483-509.

Sobir O T, Murata M, and Motoyoshi F (2000) Molecular characterization of the SCAR markers tightly linked to the TM-2 locus of the genus *Lycopersicon*. *Theor. Appl. Genet.* 101: 64-69.

Steward C N, Via L E (1993) A rapid CTAB DNA isolation technique useful for RAPD fingerprinting and other PCR applications. *Biotechniques* 14: 748-750.

Tanksley S D (1993) Mapping polygenes. *Annu Rev Genet* 27: 205-233

Tanksley S D, Ganal M W, Prince J P, de Vicente M C, Bonierbale M W, Broun P, Fulton T M, Giovannoni J J, Grandillo S, Martin G B (1992) High density molecular linkage maps of the tomato and potato genomes. *Genetics* 132: 1141-1160.

Tanksley S D, Grandillo S, Fulton T M, Zamir D, Eshed Y, Petiard V, Lopez J and Beck-Bunn T (1996) Advanced backcross QTL analysis in a cross between an elite processing line of tomato and its wild relative *L. pimpinellifolium*. *Theor Appl Genet* 92: 213-224.

Tanksley S D, Young N D, Paterson A H, Bonierbale M W (1998) RFLP mapping in plant breeding: New tools for an old science. *Bio/technology* 7: 257-263.

Tijssen P (1993) Hybridization With Nucleic Acid Probes. Part I. Theory and Nucleic Acid Preparation. In: Laboratory Techniques in Biochemistry and Molecular Biology. Elsevier.

Urbasch I (1986) Resistenz verschiedener Kultur-und Wild-tomatenpflanzen (*Lycopersicon* spp.) gegenüber *Botrytis cinerea* Pers. *J Phytopathol* 116: 344-351

Utkhede R, Bogdanoff C, McNevin J (2001) Effects of biological and chemical treatments on *Botrytis* stem canker and fruit yield of tomato under greenhouse conditions. *Can. J. Plant Pathol* 23: 253-259

Utkhede R S, Mathur S (2002) Biological control of stem canker of greenhouse tomatoes caused by *Botrytis cinerea*. *Can. J. Microbiol.* 48: 550-554

Van Berloo R (1999) GGT: Software for the display of graphical genotypes. *J. Heredity* 90: 328-329

Van Berloo R, Aalbers H, Werkman A, Niks R E (2001) Resistance QTL confirmed through development of QTL-NILs for barley leaf rust resistance. *Mol. Breeding* 8: 187-195

Van Heusden A W, Koornneef M, Voorrips R E, Bruggemann W, Pet G, Vrielink van Ginkel R, Chen X, Lindhout P (1999) Three QTLs from *Lycopersicon peruvianum* confer a high level of resistance to *Clavibacter michiganensis* ssp *michiganensis*. *Theor. Appl. Genetics* 99: 1068-1074.

von Korff M, Wang H, Leon J, Pillen K (2004) Development of candidate introgression lines using an exotic barley accession (*Hordeum vulgare* ssp *spontaneum*) as donor. *Theor Appl Genet* 109: 1736-1745

Voorrips R E (2002) MapChart: software for the graphical presentation of linkage maps and QTLs. *J. Heredity* 93: 77-78.

Vos P, Hogers R, Bleeker M, Reijans M, van de Lee T, Hornes M, Frijters A, Pot J, Peleman J, Kuiper M (1995) AFLP: a new technique for DNA fingerprinting. *Nucl. Acids Res.* 23: 4407-4414.

Wehrhahn C, Allard R W (1965) The detection and measurement of the effects of individual genes involved in inheritance of a quantitative character in wheat. Genetics 51: 109-119.

Zamir D (2001) Improving plant breeding with exotic genetic libraries. Nature reviews genetics 2: 983-989.

Zhang L, Cheng L, Xu N, Zhao M, Li C, Yuan J, and Jia S (1991) Efficient transformation of tobacco by ultrasonication. *Biotechnology* 9:996-997.

The invention claimed is:

1. A method of producing a *Botrytis*-resistant tomato plant, said method comprising the steps of:
   a) providing a *Botrytis*-resistant donor tomato plant;
   b) transferring a nucleic acid from said donor plant to one or more *Botrytis*-susceptible recipient tomato plants, wherein said transfer results in the introduction of genomic material from the donor plant in the corresponding region of the genome of said one or more recipient plants; and
   c) selecting from amongst said recipient tomato plants a plant that comprises within its genome at least one quantitative trait loci (QTL) for *Botrytis*-resistance derived from said *Botrytis*-resistant donor tomato plant, wherein said selection comprises detecting on chromosome 4, 6, 9, 11 and/or 12 of said recipient tomato plant at least one genetic marker linked to said at least one QTL for *Botrytis*-resistance,
   wherein the location of said QTL on chromosome 4 of said plant is indicated by a genomic region comprising the genetic markers CT50, C2At1g74970, P14M49-283e, P14M48-74e, P14M50-67e, CT1739 and P14M50-85h on chromosome 4 of *S. habrochaites* or on chromosome 4 of *S. lycopersicum*.

2. The method according to claim 1, wherein the location of said QTL on chromosome 6 of said plant is indicated by a genomic region comprising the genetic markers P22M50-188h, P14M48-521e, P15M48-386h, P18M51-199h, P18M51-103h, P22M50-103e, P18M51-388e, P15M48-395e, P22M50-124e, P14M48-160e and P22M50-513h on chromosome 6 of *S. habrochaites* or on chromosome 6 of *S. lycopersicum*,
   wherein the location of said QTL on chromosome 9 of said plant is indicated by a genomic region comprising the genetic markers P18M50-141, P14M49-240, TG254, TG223, TG10, P18M50-134h, P14M49-243h, P18M50-599, P14M60-222h, P22M51-417h, P14M50-174h, P14M60-157h, P14M60-107h, P15M48-138h, P14M48-113h, Tm2a, P18M51-146h, P14M48-282h and P14M50-276h on chromosome 9 of *S. habrochaites* or on chromosome 9 of *S. lycopersicum*,
wherein the location of said QTL on chromosome 11 of said plant is indicated by a genomic region comprising the genetic markers P14M60-215e, P14M61-173h, P14M50-307h, TG47, P14M50-29xCD, P18M51-358h, P18M50-27xCD, P18M51-136h, P22M50-488h, TG393, P14M61-396h, P22M51-235h and P22M51-174e on chromosome 11 of *S. habrochaites* or on chromosome 11 of *S. lycopersicum*, and
wherein the location of said QTL on chromosome 12 of said plant is indicated by a genomic region comprising the genetic markers CT19, TG68, P14M48-411e, P18M50-244h, P18M50-273h, P14M61-420h, P14M61-406h, P14M61-223h, P14M60-193h, P22M51-314h, TG565, P14M48-172h, P22M50-321e, P14M60-219e, P14M48-153h, P22M50-97h, TG296, P22M50-131h and P22M51-135h on chromosome 12 of *S. habrochaites* or on chromosome 12 of *S. lycopersicum*.

3. The method according to claim 1, wherein said transfer of nucleic acid comprising at least one QTL for *Botrytis*-resistance is performed by crossing said *Botrytis*-resistant donor tomato plant with a *Botrytis*-susceptible recipient tomato plant to produce offspring plants comprising said QTL as an introgression, and wherein step c) is performed on one or more offspring plants.

4. The method according to claim 1, wherein said transfer of nucleic acid comprising at least one QTL for *Botrytis*-resistance is performed by a transgenic method, by crossing, by protoplast fusion, by a doubled haploid technique or by embryo rescue.

5. The method according to claim 1, wherein step c) is performed by detecting said genetic marker in DNA isolated from said recipient tomato plants.

6. The method according to claim 1, wherein said step c) further comprises subjecting said plants to a bioassay for measuring *Botrytis* resistance in said plants.

7. The method according to claim 1, wherein step c) further comprises selecting a plant that comprises within its genome at least one QTL for *Botrytis*-resistance selected from the QTLs located on chromosome 1, 2 and 4 of *S. habrochaites* LYC 4/78,
wherein the location of said QTL on chromosome 1 of said plant is indicated by a genomic region comprising the genetic markers P22M50-412h, P14M50-349h, P14M60-69h, P14M49-192h, P14M49-232h, P14M49-260e, P14M50-503h, P18M50-124h and P14M49-114h on chromosome 1 of *S. habrochaites* or on chromosome 1 of *S. lycopersicum*,
wherein the location of said QTL on chromosome 2 of said plant is indicated by a genomic region comprising the genetic markers P14M60-537h, P15M48-257e, P14M49-327h, P14M49-325h, P14M61-286e, P14M61-125h, P18M51-134h and CT128 on chromosome 2 of *S. habrochaites* or on chromosome 2 of *S. lycopersicum*, and
wherein the location of said QTL on chromosome 4 of said plant is indicated by a genomic region comprising the genetic markers P18M51-169.5e, P18M51-305.4h, P14M60-262.9e, and P14M61-292.7h on chromosome 2 of *S. habrochaites* or on chromosome 2 of *S. lycopersicum*.

8. The method according to claim 1, wherein step c) further comprises selecting
a plant that comprises within its genome at least 4 QTLs for *Botrytis*-resistance selected from the group consisting of the QTLs on chromosome 1, 2, 4, 6, 9, 11 and 12, or
a plant that comprises within its genome at least 2 QTLs for *Botrytis*-resistance selected from the group consisting of the QTLs on chromosome 4, 6, 9, 11, and 12.

9. The method according to claim 1, wherein said method further comprises step d) of crossing said plant selected in step c) with a plant of a cultivated tomato line to produce offspring plants.

10. A *Botrytis*-resistant tomato plant, or part thereof, produced by the method according to claim 1, wherein the plant or part thereof comprises said QTL, and wherein said QTL is not in its natural genetic background.

11. A *Botrytis*-resistant plant of the species *S. lycopersicum*, or part thereof, comprising within its genome at least one QTL wherein said QTL is selected from the group consisting of the QTLs on chromosome 4, 6, 9, 11 and 12 of *Solanum habrochaites*, associated with *Botrytis* resistance, wherein said QTL is not in its natural genetic background,
wherein the location of said QTL on chromosome 4 of said plant or part thereof is indicated by a genomic region comprising the genetic markers CT50, C2At1g74970, P14M49-283e, P14M48-74e, P14M50-67e, CT1739 and P14M50-85h on chromosome 4 of *S. habrochaites* or on chromosome 4 of *S. lycopersicum*, and
wherein said plant optionally further comprises one or more additional QTLs associated with *Botrytis* resistance selected from the group consisting of the QTLs on chromosome 1, 2 or 4 of *Solanum habrochaites*, wherein the location of said additional QTL on chromosome 4 of said plant or part thereof is indicated by a genomic region comprising the genetic markers P18M51-169.5e, P18M51-305.4h, P14M60-262.9e, P14M61-292.7h, TG609, P14M48-345e, P14M48-177e and P18M50-147e on chromosome 4 of *S. habrochaites* on chromosome 4 of *S. lycopersicum*.

12. The *Botrytis*-resistant plant of the species *S. lycopersicum*, or part thereof according to claim 11, wherein the location of said QTL on chromosome 6 of said plant or part thereof is indicated by a genomic region comprising the genetic markers P22M50-188h, P14M48-521e, P15M48-386h, P18M51-199h, P18M51-103h, P22M50-103e, P18M51-388e, P15M48-395e, P22M50-124e, P14M48-160e and P22M50-513h on chromosome 6 of *S. habrochaites* or on chromosome 6 of *S. lycopersicum*,
wherein the location of said QTL on chromosome 9 of said plant or part thereof is indicated by a genomic region comprising the genetic markers P18M50-141, P14M49-240, TG254, TG223, TG10, P18M50-134h, P14M49-243h, P18M50-599, P14M60-222h, P22M51-417h, P14M50-174h, P14M60-157h, P14M60-107h, P15M48-138h, P14M48-113h, Tm2a, P18M51-146h, P14M48-282h and P14M50-276h on chromosome 9 of *S. habrochaites* or on chromosome 9 of *S. lycopersicum*,
wherein the location of said QTL on chromosome 11 of said plant or part thereof is indicated by a genomic region comprising the genetic markers P14M60-215e, P14M61-173h, P14M50-307h, TG47, P14M50-29xCD, P18M51-358h, P18M50-27xCD, P18M51-136h, P22M50-488h, TG393, P14M61-396h, P22M51-235h and P22M51-174e on chromosome 11 of *S. habrochaites* or on chromosome 11 of *S. lycopersicum*,
wherein the location of said QTL on chromosome 12 of said plant or part thereof is indicated by a genomic region comprising the genetic markers CT19, TG68, P14M48-411e, P18M50-244h, P18M50-273h, P14M61-420h, P14M61-406h, P14M61-223h, P14M60-193h, P22M51-314h, TG565, P14M48-172h, P22M50-321e, P14M60-219e, P14M48-153h, P22M50-97h, TG296, P22M50-131h and P22M51-135h, on chromosome 12 of *S. habrochaites* or on chromosome 12 of *S. lycopersicum*, wherein the location of said QTL on chromosome 1 of said plant or part thereof is indicated by a genomic region comprising the genetic markers selected from P22M50-412h, P14M50-349h, P14M60-69h, P14M49-192h, P14M49-232h, P14M49-260e, P14M50-503h, P18M50-124h and P14M49-114h on chromosome 1 of *S. habrochaites* or on chromosome 1 of *S. lycopersicum*, wherein the location of said QTL on chromosome 2 of said plant or part thereof is indicated by a genomic region comprising a genetic marker selected from P14M60-537h, P15M48-257e, P14M49-327h, P14M49-325h, P14M61-286e, P14M61-125h, P18M51-134h and CT128 on chromosome 2 of *S. habrochaites* or on chromosome 2 of *S. lycopersicum*.

13. A method of producing a *Botrytis*-resistant inbred, tomato plant, comprising
 a) producing a *Botrytis*-resistant tomato plant according to the method of claim 1;
 b) crossing said *Botrytis*-resistant tomato plant with itself or another tomato plant to yield progeny tomato seed;
 c) growing said progeny tomato seed of step to yield additional *Botrytis*-resistant tomato plants; and
 d) repeating the crossing and growing steps from 0 to 7 times to generate a *Botrytis*-resistant inbred tomato plant.

14. The method according to claim 13, wherein step c) further comprises the step of identifying plants that exhibit *Botrytis* resistance.

15. The method according to claim 13, wherein said method further comprises the step of selecting homozygote inbred tomato plants.

16. The *Botrytis*-resistant tomato plant, or part thereof, according to claim 11 which is an inbred or a hybrid tomato plant.

17. The *Botrytis*-resistant tomato plant, or part thereof according to claim 12 which is an inbred or a hybrid tomato plant.

18. A tissue culture of regenerable cells of the tomato plant of claim 10.

19. The method of claim 1, wherein said *Botrytis*-resistant donor tomato plant is a plant of the species *S. habrochaites*.

20. The method of claim 1, wherein said *Botrytis*-resistant donor tomato plant is a plant of the line *S. habrochaites* LYC 4/78.

21. The method of claim 1, wherein said *Botrytis*-susceptible recipient tomato plant is a plant of the species *S. lycopersicum*.

22. The tissue culture of claim 18, wherein said regenerable cells comprise cells or protoplasts isolated from a tissue selected from the group consisting of leaves, pollen, embryos, roots, root tips, anthers, flowers, fruits, and stems and seeds.

23. The method according to claim 4, wherein said transgenic method is transformation.

24. The *Botrytis* resistant plant of claim 11 wherein *S. habrochaites* is *S. habrochaites* LYC 4/78.

25. The *Botrytis* resistant plant of claim 11 wherein *S. lycopersicum* is *S. lycopersicu* cv. Moneymaker.

* * * * *